(12) United States Patent
Haesslein

(10) Patent No.: US 7,122,669 B1
(45) Date of Patent: Oct. 17, 2006

(54) PURINE DERIVATIVES, PREPARATION METHOD AND PHARMACEUTICAL COMPOSITIONS CONTAINING SAME

(75) Inventor: Jean-Luc Haesslein, Courtry (FR)

(73) Assignee: Hoechst Marion Roussel, (FR)

( * ) Notice: Subject to any disclaimer, the term of this patent is extended or adjusted under 35 U.S.C. 154(b) by 0 days.

(21) Appl. No.: 09/979,389

(22) PCT Filed: May 18, 2000

(86) PCT No.: PCT/FR00/01335

§ 371 (c)(1),
(2), (4) Date: Dec. 21, 2001

(87) PCT Pub. No.: WO00/71543

PCT Pub. Date: Nov. 30, 2000

(30) Foreign Application Priority Data

May 21, 1999 (FR) .................................. 99 06456

(51) Int. Cl.
*C07D 473/16* (2006.01)
*C07D 473/18* (2006.01)
*C07D 473/40* (2006.01)
*A61K 31/52* (2006.01)
*A61K 31/522* (2006.01)

(52) U.S. Cl. ....................................... 544/277; 544/276

(58) Field of Classification Search ................ 544/244, 544/277; 514/263.4, 263.2, 263.22, 263.23, 514/81

See application file for complete search history.

(56) References Cited

U.S. PATENT DOCUMENTS

| 5,866,702 | A * | 2/1999 | Mackman et al. .......... 544/277 |
| 6,316,456 | B1 * | 11/2001 | Meijer et al. ................ 514/277 |
| 6,413,974 | B1 * | 7/2002 | Dumont et al. ............. 544/277 |
| 6,479,487 | B1 * | 11/2002 | Dumont et al. ............. 544/277 |
| 6,767,906 | B1 * | 7/2004 | Imbach et al. .............. 544/277 |
| 6,790,958 | B1 * | 9/2004 | Lum et al. ................... 544/277 |
| 2002/0016329 | A1 * | 2/2002 | Imbach ........................ 544/277 |
| 2004/0063732 | A1 * | 4/2004 | Bordon-Pallier et al. 514/263.4 |

FOREIGN PATENT DOCUMENTS

WO WO 9716452 A * 5/1997
WO WO 9943675 A1 * 9/1999

OTHER PUBLICATIONS

Hackh's chemical Dictionary Third Edition p. 279.*

* cited by examiner

*Primary Examiner*—Mark L. Berch
(74) *Attorney, Agent, or Firm*—Charles A. Muserlian

(57) ABSTRACT

Derivatives of purine having anti-proliferative properties and in particular, derivatives of purine endowed with an inhibitory effect vis-a-vis cycline-dependent kinase proteins i.e. abbreviated to "cdk".

3 Claims, No Drawings

PURINE DERIVATIVES, PREPARATION METHOD AND PHARMACEUTICAL COMPOSITIONS CONTAINING SAME

This application is a 371 of PCT/FR00/01335 filed May 18, 2000

The present invention relates to new derivatives of purine, their preparation process, the new intermediates obtained, their use as medicaments, the pharmaceutical compositions containing them and the new use of such derivatives of purine.

Therefore a subject of the invention is new derivatives of purine having anti-proliferative properties and in particular derivatives of purine endowed with an inhibitory effect vis-a-vis cycline-dependent kinase proteins i.e. abbreviated to 'cdk' which will be used in the rest of the text.

Study of the molecular mechanisms which control the cell cycle has allowed the regulatory role of the cdk thus defined to be demonstrated. The cdk's are proteins constituted by at least two sub-units, a catalytic sub-unit (of which cdc2 is the prototype) and a regulatory sub-unit (cycline). A certain number of cdk's are thus known. The cdk's therefore fors proteinic complexes each of which is involved in a phase of the cell cycle.

Numerous documents in the literature describe the existence and the role of cdk's and as an example there can be mentioned in particular document WO 97/20842.

Several kinase inhibitors have been described such as butyrolactone, flavopiridol and 2(2-hydroxyethylamino)-6-benzylamino-9-methylpurine called olomoucine.

A subject of the present invention is therefore the products of formula (I):

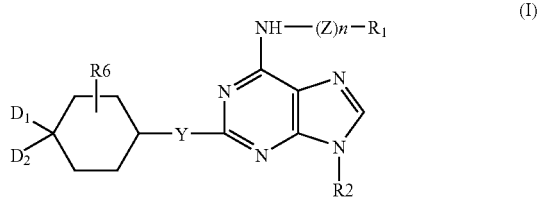

in which:

Z represents the divalent —$CH_2$—, —$SO_2$—, —CO—, —COO—, —CONH— or —$(CH_2)_2$—$NR_3$— radical, n represents the integer 0 or 1, $R_1$ is chosen from the hydrogen atom, the aryl, —$CH_2$-aryl, —$SO_2$-aryl, —CO-aryl, heterocyclic, —$CH_2$-heterocyclic, alkyl and —$SO_2$-alkyl radicals, $R_2$ represents an optionally substituted, linear or branched alkyl radical containing at most 10 carbon atoms, a cycloalkyl radical or a saturated or unsaturated heterocyclic radical constituted by at most 6 members such that one or more of the members represents an oxygen atom, a sulphur atom or the $NR_3$ radical, Y represents an oxygen atom, a sulphur atom or the $NR_3$ radical, $D_1$ and $D_2$ either, identical or different, are chosen from the hydrogen atom, the hydroxyl radical, the linear or branched alkyl, alkoxy radicals containing at most 6 carbon atoms and the $NHR_5$ radicals, or together form the =O or =N—$OR_4$ radical, $R_3$ represents the hydrogen atom, an alkyl or cycloalkyl radical, $R_4$ represents the hydrogen atom, an alkyl, cycloalkyl or aryl radical, $R_5$ represents the hydrogen atom, an alkyl, cycloalkyl radical or the —COOtBu (Boc) radical, $R_6$ represents the hydrogen atom, a halogen atom, the hydroxyl radical, a linear or branched alkyl, alkoxy radical containing at most 6 carbon atoms or an $NHR_3$ radical, all the cycloalkyl radicals defined above containing at most 6 carbon atoms, all the alkyl radicals defined above being linear or branched containing at most 6 carbon atoms (unless specified), all the cycloalkyl, alkyl, aryl and heterocyclic radicals defined above being optionally substituted by one or more radicals chosen from the halogen atoms, the hydroxyl, cyano, nitro, aryl, trifluoromethyl, trifluoromethoxy radicals, the alkoxy radical containing at most 6 carbon atoms, the —$NHR_4$, —$COR_4$, —$COOR_4$ and —$CONHR_4$ radicals in which $R_4$ has the meaning indicated above and the radicals with an acid function and acid isosters, all the aryl and heterocyclic radicals defined above also being optionally substituted by one or more alkyl radicals containing at most 6 carbon atoms optionally substituted by a CN radical or by a $COOR_4$ radical in which $R_4$ has the meaning indicated above, all the aryl radicals defined above also being optionally substituted by a dioxol radical, by an —S-alkyl radical containing at most 6 carbon atoms or by an aryl or cycloalkyl radical containing at most 6 carbon atoms optionally interrupted by one or more heteroatoms chosen from the oxygen, nitrogen or sulphur atoms, said products of formula (I) being in all possible racemic, enantiomeric and diastereoisomeric forms, as well as the addition salts with mineral and organic acids or with mineral and organic bases of said products of formula (I).

In the products of formula (I) and in what follows:

the term linear or branched alkyl radical designates the methyl, ethyl, propyl, isopropyl, butyl, isobutyl, sec-butyl, tert-butyl, pentyl, isopentyl, hexyl, isohexyl and also heptyl, octyl, nonyl and decyl radicals as well as their linear or branched position isomers, the term linear or branched alkoxy designates the methoxy, ethoxy, propoxy, isopropoxy, linear, secondary or tertiary butoxy, pentoxy or hexoxy radicals as well as their linear or branched position isomers, the term halogen atom preferably designates the chlorine atom, but can also represent a fluorine, bromine or iodine atom atom, the term cycloalkyl radical designates the cyclopropyl, cyclobutyl radicals and quite particularly the cyclopentyl and cyclohexyl radicals, the term aryl radical designates unsaturated, monocyclic radicals or radicals constituted by condensed, carbocyclic rings. As examples of such an aryl radical, there can be mentioned the phenyl or naphthyl radicals, the term heterocyclic radical designates a saturated or unsaturated carbocylic radical constituted by at most 6 members interrupted by one or more heteroatoms, identical or different, chosen from the oxygen, nitrogen or sulphur atoms. There can be mentioned in particular the dioxolane, dioxane, dithiolane, thiooxolane, thiooxane, piperazinyl radical, piperazinyl substituted by a linear or branched alkyl radical, containing at most 4 carbon atoms, thienyl such as 2-thienyl and 3-thienyl, furyl such as 2-furyl, pyridyl such as 2-pyridyl, 3-pyridyl and 4-pyridyl, pyrimidyl, pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl; there can also be mentioned condensed heterocyclic groups containing at least one heteroatom chosen from sulphur, nitrogen and oxygen, for example benzothienyl such as 3-benzothienyl, benzofuryl, benzopyrrolyl, benzimidazolyl, benzoxazolyl, thionaphthyl, indolyl or purinyl. There can quite particularly be mentioned the following radicals: thienyl such as 2-thienyl and 3-thienyl, furyl such as 2-furyl, tetrahydrofuryl, thienyl, tetrahydrothienyl, pyrrolyl, pyrrolinyl and pyrrolidinyl.

Among the saturated or unsaturated heterocyclic radicals, unsaturated heterocyclic radicals are preferred.

the term acid function or acid isoster designates the free, salified or esterified carboxy radical, the free or salified tetrazolyl radical, or the following radicals:

—SO$_3$H, —PO(OH)$_2$, NH—SO$_2$—CF$_3$, —NH—SO$_2$—NH—V, NH—SO$_2$—NH—CO—V, —NH—CO—V, —NH—CO—NH—V, —NH—CO—NH—SO$_2$—V, —SO$_2$—NH—V, —SO$_2$—NH—CO—V, —SO$_2$—NH—CO—NH—V, —CO—NH—V, —CO—NH—OH, —CO—NH—SO$_2$—V in which V represents a hydrogen atom, a linear or branched alkyl or alkenyl radical containing at most 6 carbon atoms, a phenyl radical or a thiazolyl radical, the alkyl, alkenyl and phenyl radicals represented by V being optionally substituted by the substituents indicated above for the alkyl and aryl radicals of the products of formula (I).

The carboxy radical(s) of the products of formula (I) can be salified or esterified by the various groups known to a person skilled in the art, among which there can be mentioned, for example:

among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine, among the esterification compounds, the alkyl radicals in order to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from the halogen atoms, the hydroxyl, alkoxy, acyl, acyloxy, alkylthio, amino or aryl radicals such as, for example, in the chloromethyl, hydroxypropyl, methoxymethyl, propionyloxymethyl, methylthiomethyl, dimethylaminoethyl, benzyl or phenethyl groups.

The addition salts with the mineral or organic acids of the products of formula (I) can be, for example, the salts formed with the following acids: hydrochloric, hydrobromic, hydroiodic, nitric, sulphuric, phosphoric, propionic, acetic, trifluoroacetic, formic, benzoic, maleic, fumaric, succinic, tartaric, citric, oxalic, glyoxylic, aspartic, ascorbic, alkylmonosulphonic acids such as for example methanesulphonic acid, ethanesulphonic acid, propanesulphonic acid, alkyldisulphonic acids such as for example methanedisulphonic acid, alpha,beta-ethanedisulphonic acid, arylmonosulphonic acids such as benzenesulphonic acid and aryldisulphonic acids.

It should be remembered that stereoisomerism can be defined in its broadest sense as the isomerism of compounds having the same structural formulae, but the different groups of which are arranged differently in space, such as in particular in monosubstituted cyclohexanes the substituent of which can be in the axial or equatorial position, and the different possible rotational configurations of ethane derivatives. However, another type of stereoisomerism exists, due to the different spatial arrangements of fixed substituents, either on the double bonds, or on the rings, which is often called geometric isomerism or cis-trans isomerism. The term stereoisomers is used in the present Application in its widest sense and therefore-relates to all of the compounds indicated above.

A subject of the present invention is therefore the products of formula (I) as defined above corresponding to formula (Ia):

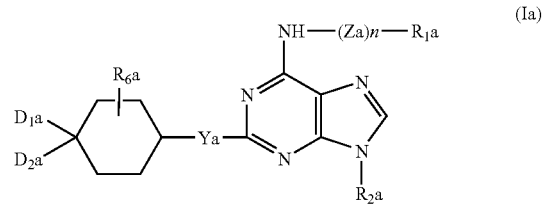

in which:

Za represents the divalent —CH$_2$—, —SO$_2$—, —CO— or —(CH$_2$)$_2$—NR$_3$a-radical, n represents the integer 0 or 1, R$_1$a is chosen from the hydrogen atom and the phenyl, —CH$_2$-phenyl, —SO$_2$-phenyl, —CO-phenyl, pyridyl, —CH$_2$-pyridyl, alkyl and —SO$_2$-alkyl radicals, R$_2$a represents an alkyl, cycloalkyl radical or a saturated or unsaturated heterocyclic radical constituted by 5 members such that one of the members represents an oxygen atom, a sulphur atom or the NR$_3$ radical, Ya represents an oxygen atom, a sulphur atom or the NR$_3$a radical, D$_1$a and D$_2$a either, identical or different, are chosen from the hydrogen atom, the hydroxyl radical, the linear or branched alkyl, alkoxy radicals containing at most 6 carbon atoms and the NHR$_5$a radicals, or together form the =O or =N—OR$_4$a radical, R$_3$a represents the hydrogen atom, an alkyl or cycloalkyl radical, R$_4$a represents the hydrogen atom, an alkyl, cycloalkyl or phenyl radical, R$_5$a represents the hydrogen atom, an alkyl, cycloalkyl radical or the —COOtBu, (Boc) radical, R$_6$a represents the hydrogen atom, a halogen atom, the hydroxyl radical, a linear or branched alkyl, alkoxy radical containing at most 6 carbon atoms or an NHR$_3$a radical, all the cycloalkyl radicals defined above containing at most 6 carbon atoms, all the alkyl radicals defined above being linear or branched containing at most 6 carbon atoms, all the cycloalkyl, alkyl and phenyl radicals defined above being optionally substituted by one or more radicals chosen from the halogen atoms and the following radicals: hydroxyl, cyano, nitro, aryl, trifluoromethyl, trifluoro-methoxy, alkoxy containing at most 6 carbon atoms, —NHR$_4$a, —COR$_4$a, —COOR$_4$a and —CONHR$_4$a in which R$_4$a has the meaning indicated above, and the SO$_3$H, PO(OH)$_2$, NH—SO$_2$—CF$_3$, NH—SO$_2$—NH—V, SO$_2$—NH—V and NH—SO$_2$—NH—CO—V radicals in which V represents a hydrogen atom, a phenyl, thiazolyl, alkyl or alkenyl radical, the alkyl and alkenyl radicals being linear or branched containing at most 6 carbon atoms, all the phenyl radicals defined above also being optionally substituted by one or more radicals chosen from the alkyl radicals containing at most 6 carbon atoms, optionally substituted by a CN or COOR$_4$a radical in which R$_4$a has the meaning indicated above, the —S-alkyl radical containing at most 6 carbon atoms, the aryl or cycloalkyl radical containing at most 6 carbon atoms optionally interrupted by one or more atoms chosen from the oxygen, nitrogen or sulphur atoms and the dioxol radical, said products of formula (Ia) being in all possible racemic, enantiomeric and diastereoisomeric isomer forms, as well as the addition salts with mineral and organic acids or with mineral and organic bases of said products of formula (Ia).

A more particular subject of the present invention is the products of formula (I) as defined above corresponding to formula (Ib):

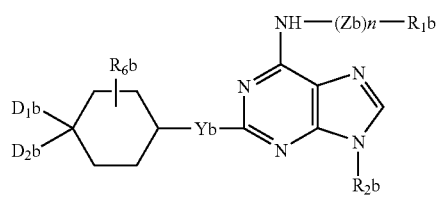

in which:

Zb represents the divalent —CH$_2$—, —SO$_2$—, —CO— or —(CH$_2$)$_2$—NR$_3$b-radical, n represents the integer 0 or 1, R$_1$b is chosen from the hydrogen atom and the phenyl, —CH$_2$-phenyl, —CO-phenyl, —SO$_2$-phenyl, pyridyl, —CH$_2$-pyridyl, alkyl, and —SO$_2$-alkyl radicals, in which the alkyl radical contains at most 4 carbon atoms and the alkyl and phenyl radicals are optionally substituted as indicated hereafter, R$_2$b represents a linear or branched alkyl radical containing at most 6 carbon atoms, a cycloalkyl radical containing at most 6 carbon atoms, a tetrahydrofuryl, tetrahydrothienyl, pyrrolinyl or pyrrolidinyl radical, Yb represents the oxygen atom or the NR$_3$b radical, D$_1$b and D$_2$b either, identical or different, are chosen from the hydrogen atom, the hydroxyl radical, the linear or branched alkyl and alkoxy radicals containing at most 4 carbon atoms and the NHR$_5$b radicals, or together form the =O or =N—OR$_4$b radical, R$_3$b represents the hydrogen atom, an alkyl containing at most 4 carbon atoms, cycloalkyl containing at most 6 carbon atoms or —CH$_2$-phenyl radical, R$_4$b represents the hydrogen atom, an alkyl containing at most 4 carbon atoms, phenyl, —CH$_2$-phenyl radical or the cycloalkyl radical containing at most 6 carbon atoms optionally substituted by the —NHR$_3$b radical, R$_5$b represents the hydrogen atom, an alkyl, cycloalkyl radical containing at most 6 carbon atoms or the —COOtBu (Boc) radical, all the cycloalkyl, alkyl and phenyl radicals defined above being optionally substituted by one or more radicals chosen from the halogen atoms and the following radicals: hydroxyl, cyano, nitro, phenyl, trifluoromethyl, trifluoromethoxy, alkoxy containing at most 4 carbon atoms, free, salified or esterified carboxy, —NHR$_4$b, —COR$_4$b and —CONHR$_4$b in which R$_4$b has the meaning indicated above, and the SO$_3$H, PO(OH)$_2$, NH—SO$_2$—CF$_3$, SO$_2$NH$_2$ and SO$_2$—NH-thiazolyl radicals, all the phenyl radicals defined above also being optionally substituted by one or more radicals chosen from the alkyl radicals containing at most 4 carbon atoms, optionally substituted by a CN or COOR$_4$b radical in which R$_4$b has the meaning indicated above, the —S-alkyl radical containing at most 4 carbon atoms, the tetrazolyl radical, the cycloalkyl radical optionally interrupted by one or more atoms chosen from the oxygen or nitrogen atoms and the dioxol radical, said products of formula (Ib) being in all possible racemic, enantiomeric and diastereoisomeric isomer forms, as well as the addition salts with mineral and organic acids or with mineral and organic bases of said products of formula (Ib).

A more particular subject of the present invention is the products of formula (I) as defined above corresponding to formula (Ic):

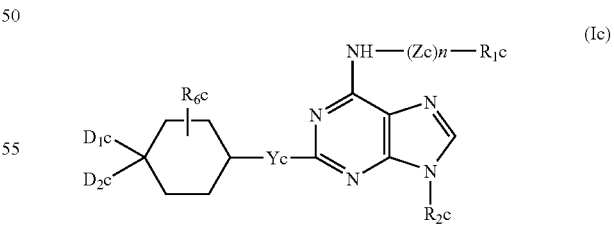

in which:

Zc represents the divalent —CH$_2$—, —SO$_2$—, —CO—, —(CH$_2$)$_2$—NH—, —(CH$_2$)$_2$-Nalkyl, —(CH$_2$)$_2$—N—CH$_2$-phenyl radical in which the phenyl radicals are optionally substituted by a halogen atom, a hydroxyl, trifluoromethyl, alkoxy radical containing at most 4 carbon atoms or free, salified or esterified carboxy, n represents the integer 0 or 1, $R_1c$ is chosen from the hydrogen atom and the phenyl, —$CH_2$-phenyl, —$SO_2$-phenyl, —CO-phenyl, pyridyl, alkyl and —$SO_2$-alkyl radicals, in which the alkyl radicals contain at most 4 carbon atoms and are optionally substituted by a free, salified or esterified carboxy radical, and all the phenyl radicals are optionally substituted by one or more radicals chosen from the halogen atoms and the following radicals: hydroxyl, cyano, nitro, trifluoromethyl, trifluoromethoxy, thioalkyl and alkoxy containing at most 4 carbon atoms, alkyl containing at most 4 carbon atoms optionally substituted by a cyano, —COOH or COOalk radical, the phenyl, tetrazolyl, cycloalkyl radicals interrupted by one or more oxygen or nitrogen atoms, the —$SO_2NH_2$ and $SO_2$—NH-thiazolyl radicals, the dioxol, free, esterified or salified carboxy radicals and the —$NHR_4c$ and —$CONHR_4c$ radicals in which $R_4c$ represents a hydrogen atom, an alkyl radical containing at most 4 carbon atoms or a cyclohexyl radical optionally substituted by an $NH_2$ radical, $R_2c$ represents a linear or branched alkyl radical containing at most 6 carbon atoms, the cyclopentyl, tetrahydrofuryl radicals or the tetrahydrothienyl radical, Yc represents the oxygen atom or the —NH or -Nalkyl radical in which the linear or branched alkyl radical contains at most 4 carbon atoms, $D_1c$ and $D_2c$ either, identical or different, are chosen from the hydrogen atom, the hydroxyl radical, the linear or branched alkyl and alkoxy radicals containing at most 4 carbon atoms and the —$NH_2$, —NH—COOtBu or —NHalkyl radicals in which the linear or branched alkyl radical contains at most 4 carbon atoms, or together form the =O or =N—Oalkyl radical, in which the linear or branched alkyl radical contains at most 4 carbon atoms, $R_6c$ represents the hydrogen atom, a halogen atom or the hydroxyl radical, said products of formula (Ic) being in all possible racemic, enantiomeric and diastereoisomeric isomer forms, as well as the addition salts with mineral and organic acids or with mineral and organic bases of said products of formula (Ic).

A more particular subject of the present invention is also the products of formula (I) as defined above corresponding to formula (Id):

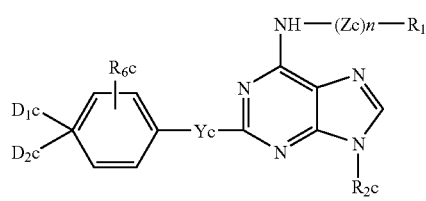

in which:

Zc represents the divalent —$CH_2$—, —$SO_2$—, —CO—, —$(CH_2)_2$—NH—, —$(CH_2)_2$-Nalkyl, —$(CH_2)_2$—N—$CH_2$-phenyl radical in which the phenyl radicals are optionally substituted by a halogen atom, a hydroxyl, trifluoromethyl, alkoxy containing at most 4 carbon atoms or free, salified or esterified carboxy radical, n represents the integer 0 or 1, $R_1d$ is chosen from the hydrogen atom and the phenyl, —$CH_2$-phenyl, —$SO_2$-phenyl, —CO-phenyl, alkyl and —$SO_2$-alkyl radicals, in which the alkyl radicals contain at most 4 carbon atoms and are optionally substituted by a free, salified or esterified carboxy radical, and all the phenyl radicals are optionally substituted by one or more radicals chosen from the halogen atoms and the hydroxyl, cyano, nitro, trifluoromethyl, trifluoromethoxy, thioalkyl and alkoxy containing at most 4 carbon atoms, alkyl containing at most 4 carbon atoms optionally substituted by a free or esterified cyano or carboxy radical, the morpholinyl, phenyl, tetrazolyl, —$SO_2NH_2$, $SO_2$—NH-thiazolyl, dioxol, free, esterified or salified carboxy, —$NHR_4c$ and —$CONHR_4c$ radicals in which $R_4c$ represents a hydrogen atom, an alkyl radical containing at most 4 carbon atoms or a cyclohexyl radical optionally substituted by an $NH_2$ radical, $R_2c$ represents a linear or branched alkyl radical containing at most 6 carbon atoms, the cyclopentyl, tetrahydrofuryl radicals or the tetrahydrothienyl radical, Yc represents the oxygen atom or the —NH or —N-alkyl radical in which the linear or branched alkyl radical contains at most 4 carbon atoms, $D_1c$ and $D_2c$ either, identical or different, are chosen from the hydrogen atom, the hydroxyl radical, the linear or branched alkyl and alkoxy radicals containing at most 4 carbon atoms and the —$NH_2$, —NH—COOtBu or —NH-alkyl radicals in which the linear or branched alkyl radical contains at most 4 carbon atoms, or together form the =O or =N-Oalkyl radical, in which the linear or branched alkyl radical contains at most 4 carbon atoms, $R_6c$ represents the hydrogen atom, a halogen atom or the hydroxyl radical, said products of formula (Id) being in all possible racemic, enantiomeric and diastereoisomeric isomer forms, as well as the addition salts with mineral and organic acids or with mineral and organic bases of said products of formula (Id).

The products in which $R_2$ represents cyclopentyl are quite particularly preferred.

A quite particular subject of the present invention is the products of formula (I) as defined above, corresponding to the following formulae:

Dihydrochloride of butyl trans-4-[[[2-[(4-aminocyclohexyl)-amino]-9-cyclopentyl-9H-purin-6-y]-amino]-methyl]-benzoate, Dihydrochloride of ethyl trans-4-[[2-[(4-aminocyclohexyl)-amino]-9-cyclopentyl-9H-purin-6-yl]-amino]-benzoate, trans-N2-(4-aminocyclohexyl)-9-cyclo-pentyl-N6-[2-[(phenylmethyl)-amino]-ethyl]-9H-purin-2,6-diamine trihydrochloride, trans-N2-(4-aminocyclohexyl)-N6-(2-aminoethyl)-9-cyclopentyl-9H-purin-2,6-diamine trihydrochloride, trans-N2-(4-aminocyclohexyl)-9-cyclo-pentyl-N6-[2-[[(4-methoxyphenyl)-methyl]-amino]-ethyl]-9H-purin-2,6-diamine trihydrochloride, trans-N2-(4-aminocyclohexyl)-N6-[2-[[[4-chloro-3-(trifluoromethyl)-phenyl]-methyl]-amino]-ethyl]-9-cyclopentyl-9H-purin-2,6-diamine trihydrochloride, trans-N2-(4-aminocyclohexyl)-9-cyclo-pentyl-N6-[(diphenylmethyl)-amino]-ethyl]-9H-purin-2,6-diamine trihydrochloride, trans-N2-(4-aminocyclohexyl)-N6-[2-[[(4-chlorophenyl)-methyl]-amino]-ethyl]-9-cyclopentyl-9H-purin-2,6-diamine trihydrochloride,
Dihydrochloride of ethyl trans(.+-.)-4-[[2-[(4-aminocyclohexyl)-amino]-9-(tetrahydro-3-thienyl)-9H-purin-6-yl]-amino]-benzoate,
trans(.+-.)-N2-(4-aminocyclohexyl)-9-(tetrahydro-3-thienyl)-N6-[4-(trifluoromethoxy)-phenyl]-9H-purin-2,6-diamine dihydrochloride,
trans(.+-.)-N2-(4-aminocyclohexyl)-9-(tetrahydro-3-furanyl)-N6-[(4-trifluoromethoxy)-phenyl]-9H-purin-2,6-diamine dihydrochloride,
trans-N2-(4-aminocyclohexyl)-9-(1-ethyl-propyl)-N6-[4-(trifluoromethoxy)-phenyl]-9H-purin-2,6-diamine dihydrochloride,
Dihydrochloride of ethyl trans-4-[[2-[(4-aminocyclohexyl)-amino]-9-(1-ethylpropyl)-9H-purine-6-yl]-amino]-benzoate.

A quite particular subject of the present invention is also the products of formula (I) as defined above, corresponding to the following formulae:
Dihydrochloride of ethyl trans-3-[[2-[(4-aminocyclohexyl)-amino]-9-cyclopentyl-9H-purin-6-yl]-amino]-benzoate,
trans-N2-(4-aminocyclohexyl)-9-cyclopentyl-N6-[2-[[(3,4-dichlorophenyl)-amino]-methyl]-ethyl]-9H-purine-2,6-diamine trihydrochloride,
trans-N2-(4-aminocyclohexyl)-9-cyclopentyl-N6-[2-[[(3,5-dichlorophenyl)-methyl]-amino]-ethyl]-9H-purine-2,6-diamine trihydrochloride,
trans-4-[[2-[(4-aminocyclohexyl)-amino]-9-cyclopentyl-9H-purin-6-yl]amino]benzeneacetonitrile dihydrochloride,
trans-N2-(4-aminocyclohexyl)-9-cyclopentyl-N6-[4-(4-morpholinyl)-phenyl]-9H-purine-2,6-diamine dihydrochloride,
trans-4-[[2-[(4-aminocyclohexyl)-amino]-9-cyclopentyl-9H-purin-6-yl]amino]-benzonitrile dihydrochloride,
trans-N2-(4-aminocyclohexyl)-9-cyclopentyl-N6-(4-nitrophenyl)-9H-purine-2,6-diamine dihydrochloride,
trans-N2-(4-aminocyclohexyl)-N6-(4-aminophenyl)-9-cyclopentyl-9H-purine-2,6-diamine dihydrochloride,
trans-N2-(4-aminocyclohexyl)-9-cyclopentyl-N6-(4-methoxyphenyl)-9H-purine-2,6-diamine dihydrochloride,
Dihydrochloride of diethyl trans-5-[[2-[(4-aminocyclohexyl)-amino]-9-cyclopentyl-9H-purin-6-yl]-amino]-1,3-benzenedicarboxylate.

It should be noted that in the preferred products of the present invention the substituents of the cyclohexyl radical are in trans position with respect to each other.

A subject of the present invention is also the process for the preparation of the products of formula (I), as defined above, characterized in that the compound of formula (II):

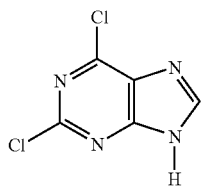

(II)

is subjected to a reaction with a compound of formula (III):

$R_2'$—OH (III)

in which $R_2'$ has the meaning indicated above for $R_2$, in which the optional reactive functions are optionally protected by protective groups, in order to obtain the product of formula (IV):

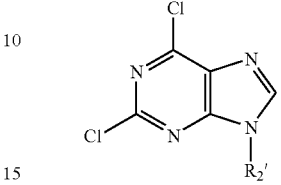

(IV)

in which $R_2'$ has the meaning indicated above, which product of formula (IV) is subjected to the reactions of any one of the following routes 1 to 6:

either, according to route 1, the product of formula (IV) is subjected to a reaction with a compound of formula (V):

$NH_2$—$(Z_1')n$—$R_1'$ (V)

in which $R_1'$ is selected from the group consisting of hydrogen, phenyl, —$CH_2$-phenyl and alkyl and n is 0 or 1 and protective groups, and n represents the integer 0 or 1 and when n represents 1, then $Z_1'$ represents —$CH_2$ in order to obtain a product of formula (VIII):

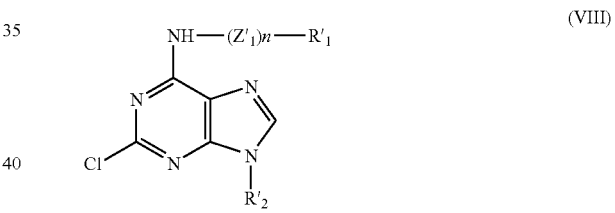

(VIII)

in which $R_1'$, $R_2'$ and $Z_1'$ have the meanings indicated above,
or, according to route 2, the product of formula (IV) is subjected to a reaction with a compound of formula (VI):

$NH_2$—$SO_2$—$R_1'$ (VI)

in which $R_1'$ has the meaning indicated above, in which the optional reactive functions are optionally protected by protective groups, in order to obtain a product of formula (IX):

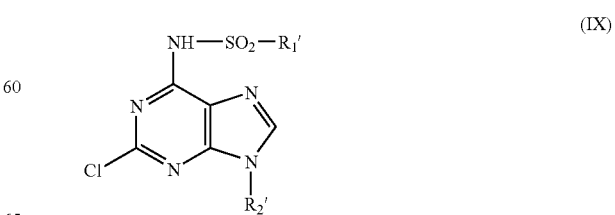

(IX)

in which $R_1'$ and $R_2'$ have the meanings indicated above, or, according to route 3, the product of formula (IV) is subjected to a reaction with the compound of formula (VII):

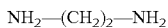  (VII)

in order to obtain a product of formula (X):

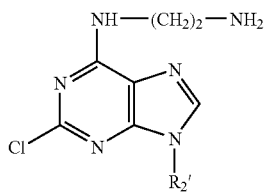  (X)

in which $R_2'$ has the meaning indicated above, which product of formula (X) is subjected:

either to a reaction with a compound of formula (XI):

  (XI)

in which $R_1'$ has the meaning indicated above, in order to obtain a compound of formula (XII):

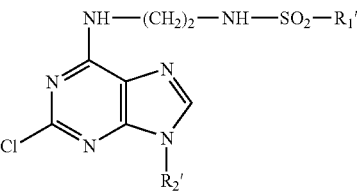  (XII)

in which $R_1'$ and $R_2'$ have the meanings indicated above, or to a reaction with a product of formula $(XI)_A$:

Cl—CO—$R_1'$  $(XI)_A$ in which $R_1'$ has the meaning indicated above, in order to obtain a product of formula $(XII)_A$:

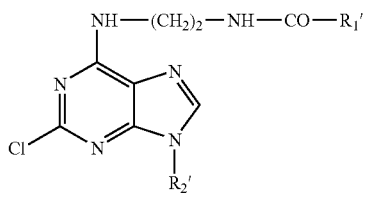  $(XII)_A$ in which $R_1'$ and $R_2'$ have the meanings indicated above, or to a reaction in the presence of a reducing agent with a product of formula (XVII):

  (XVII)

in which $R_7$ represents an aryl, heterocyclic or alkyl radical, these radicals being as defined above for the $R_1$ radical in which the optional reactive functions are optionally protected, in order to obtain a product of formula (XIII):

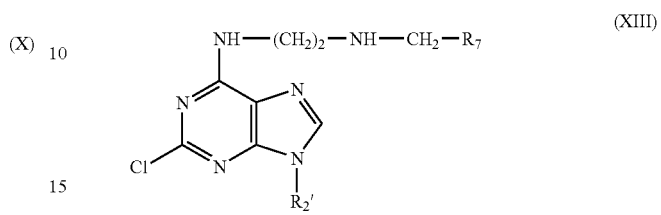  (XIII)

in which $R_2'$ and $R_7$ have the meanings indicated above, or, according to route 4, the product of formula (IV) is subjected to a reaction with a compound of formula (XVIII):

$R_1'$—CO—$NH_2$  (XVIII)

in which $R_1'$ has the meaning indicated above, in order to obtain a product of formula $(M_1)$:

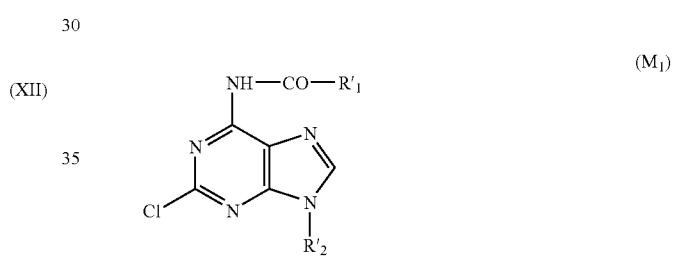  $(M_1)$ in which $R_1'$ and $R_2'$ have the meanings indicated above, or, according to route 5 or 6, the product of formula (IV) is subjected to a reaction with ammonia in order to obtain a product of formula (XIX):

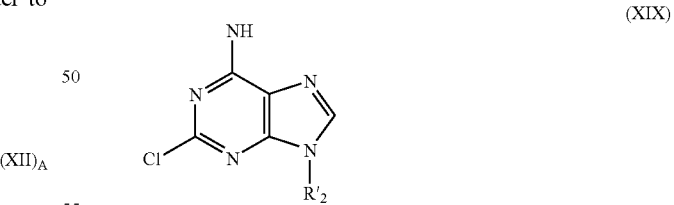  (XIX)

in which $R_2'$ has the meaning indicated above, which product of formula (XIX) is subjected:

either, according to route 5, to a reaction with a product of formula (XX):

ClCOO$R_1'$  (XX)

in which $R_1'$ has the meaning indicated above, in order to obtain a product of formula $(M_2)$:

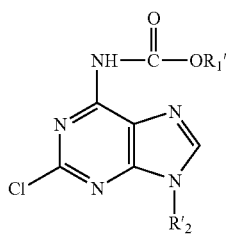

(M₂)

in which $R_1'$ and $R_2'$ have the meanings indicated above, or, according to route 6, to a reaction with an isocyanate of formula (XXI):

(XXI)

in which $R_1'$ has the meaning indicated above, in order to obtain a product of formula (M₃):

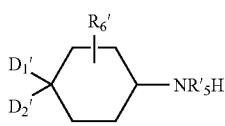

(M₃)

in which $R_1'$ and $R_2'$ have the meanings indicated above, which products of formulae (VIII), (IX), (XII), (XIII), (M₁), (M₂) and (M₃) can be subjected to the reactions of any one of the following routes a), b) or c):

a) either to a reaction with a compound of formula (XIV):

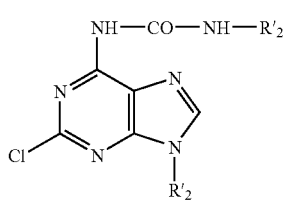

(XIV)

in which $D_1'$, $D_2'$, $R_5'$ and $R_6'$ have the meanings indicated previously for $D_1$, $D_2$, $R_5$ and $R_6$ respectively in which the optional reactive functions are optionally protected by protective groups, in order to obtain a product of formula (Ix):

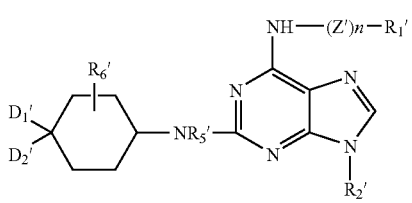

(Ix)

in which $R_1'$, $R_2'$, $R_5'$, $R_6'$, $D_1'$ and $D_2'$ have the meanings indicated above and Z' has the meaning indicated above for Z in which the optional reactive functions are optionally protected by protective groups, which product of formula (Ix) therefore corresponds to a product of formula (I') in which Y represents —NR₅— the products of formula (I') having the meaning indicated above for the products of formula (I) in which the optional reactive functions are optionally protected by protective groups, b) or to a reaction with a compound of formula (XV):

(XV)

in which $D_1'$ and $D_2'$ have the meanings indicated above, in order to obtain a product of formula (Iy):

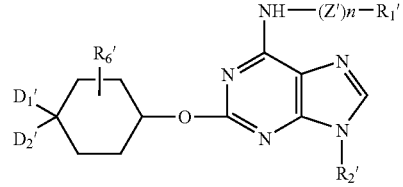

(Iy)

in which $R_1'$, $R_2'$, $R_5'$, $R_6'$, $D_1'$, $D_2'$ and Z' have the meanings indicated above, which product of formula (Iy) therefore corresponds to a product of formula (I') as defined above in which Y represents —O— c) or to a reaction with a compound of formula (XVI):

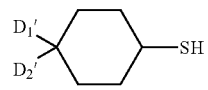

(XVI)

in which $D_1'$ and $D_2'$ have the meanings indicated above, in order to obtain a product of formula (Iz):

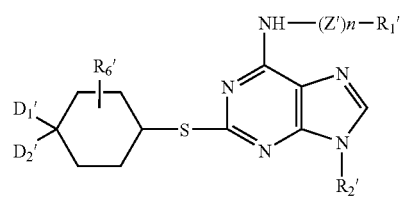

(Iz)

in which $R_1'$, $R_2'$, $R_5'$, $R_6'$, $D_1'$, $D_2'$ and Z' have the meanings indicated above, which product of formula (Iz) therefore corresponds to a product of formula (I') as defined above in which Y represents —S—, which products of formulae (Ix), (Iy) and (Iz) can be products of formula (I) and which, in order to obtain some or other products of formula (I), can be subjected, if desired and if necessary, to one or more of the following conversion reactions, in any order:

a) an esterification reaction of the acid function, b) a saponification reaction of the ester function to an acid function, c) an oxidation reaction of the alkylthio group to a corresponding sulphoxide or sulphone, d) a conversion reaction of the ketone function to an oxime function, e) a reduction reaction of the free or esterified carboxy function to an alcohol function, f) a conversion reaction of the alkoxy function to a hydroxyl function, or also of the hydroxyl function to an alkoxy function, g) an oxidation reaction of the alcohol function to an aldehyde, acid or ketone function, h) a conversion reaction of the nitrile radical to tetrazolyl, i) a reduction reaction of the nitrated compounds to aminated compounds, j) an elimination reaction of the protective groups which can be carried by the protected reactive functions, k) a salification reaction by a mineral or organic acid or by a base in order to obtain the corresponding salt, l) a resolution reaction of the racemic forms to resolved products, said products of formula (I) thus obtained being in all possible racemic, enantiomeric and diastereoisomeric isomer forms.

It should be noted that such conversion reactions of substituents to other substituents can also be carried out on the starting products as well as on the intermediates defined above before continuing the synthesis according to the reactions indicated in the process described above.

Under preferential conditions for the implementation of the invention, the process described above can be carried out as follows:

The reaction of the product of formula (II) with a product of formula (III) in order to produce a product of formula (IV) can be carried out in particular in the presence of DEAD, DIAD (diisopropyl azodicarboxylate) or also of triphenylphosphine P(phenyl)$_3$ in a solvent such as THF or $CH_2$—$Cl_2$ or also DMF.

In the product of formula (III), the $R_2$ radical represents in particular an alkyl, cycloalkyl, tetrahydrofuryl or tetrahydrothienyl radical.

There can be mentioned in particular the following products of formula (III): cyclopentanol, 3-hydroxytetrahydrofuran, 3-hydroxytetrahydrothiophene, 2-hydroxybutanol and 3-hydroxypentanol.

The products of formula (IV) thus obtained are subjected according to route 1) as defined above to the action of the product of formula (V) as defined above in which n represents the integer 0 and Z represents the —$CH_2$— radical when n is equal to 1, in particular in an alcohol such as butanol at a temperature of approximately 80° C. or in DMF in order to produce a product of formula (VIII) as defined above.

The products of formula (IV) are subjected according to route 2) to the action of the product of formula (VI) as defined above in which Z represents —$SO_2$, in particular in THF, DME, $Cs_2CO_3$, $K_2CO_3$ or also $Na_2CO_3$ in order to produce a product of formula (IX) as defined above.

The products of formula (IV) are subjected according to route 3 to the action of the product of formula (VII) as defined above in which Z represents the —$(CH_2)_2NHR_3$— radical, in particular in butanol at a temperature of approximately 75° C. for approximately 2 or 3 hours in order to produce a product of formula (X) as defined above.

The product of formula (X) thus obtained can be subjected to the action of a product of formula (XI) or $(XI)_A$ as defined above in DME, $Cs_2CO_3$ or also $CH_2Cl_2$ and $N(Et)_3$ for approximately one hour at ambient temperature in order to produce respectively a product of formula (XII) or $(XII)_A$ as defined above.

The product of formula (X) can also be subjected to the action of an aldehyde of formula (XVII) in particular in an alcohol such as methanol or ethanol, in the presence of $NaBH_4$ or $NaBH_3CN$ in order to produce a product of formula (XIII) as defined above.

For the other values of Z, the corresponding products are prepared according to routes 4, 5 and 6 of the process as follows: the products of formula (IV) are subjected according to route 4 to the action of the product of formula (XVIII) in which Z represents CO in order to produce a product of formula $(M_1)$ as defined above.

The reaction of the product of formula (IV) with the product of formula (XVIII) can be carried out under the same conditions as those for the reaction of the product of formula (IV) with the product of formula VI in order to produce the product of formula (IX) in which Z represents $SO_2$.

The products of formula (IV) are subjected to the action of ammonia in order to produce a product of formula (XIX). The product of formula (XIX) can then be subjected either according to route 5 to the action of the product of formula (XX) in which Z represents COO in order to produce a product of formula $(M_2)$ as defined above, or according to route 6 to the action of the product of formula (XXI) in which Z represents CONH in order to produce a product of formula $(M_3)$ as defined above.

The reactions of the product of formula (XIX) with the products of formulae (XX) or (XXI) can be carried out in DME or THF, in the presence of $Cs_2CO_3$ or $K_2CO_3$.

The products thus obtained of formulae (VIII), (IX), (XII), $(XII)_A$, (XIII), $(M_1)$, $(M_2)$ and $(M_3)$, as defined above are subjected according to route a) to the action of a compound of formula (XIV) as defined above in which Y represents —$NR_5$, for a condensation reaction which if appropriate can be carried out at a temperature of approximately 140° C.: such a condensation reaction can be followed by a salification reaction in the presence of hydrochloric acid for example or also of tartaric, citric or methane sulphonic acid, in an alcohol such as for example ethanol or methanol in order to produce products of formula (Ix) as defined above.

The products of formula (Ix) are therefore products of formula (I) in which the optionally reactive functions are optionally protected and in which Y represents —$NR_5$— as defined above.

The products of formulae (VIII), (IX), (XII), (XII)$_A$, (XIII), (M$_1$), (M$_2$) and (M$_3$), as defined above can also be subjected according to route b) to the action of a compound of formula (XV) as defined above in which Y represents the oxygen atom, for a condensation reaction for example in the presence of NaH in THF or DMF at ambient temperature or while heating: such a condensation reaction can be followed by a salification reaction in the presence of hydrochloric acid for example or also of tartaric, citric or methane sulphonic acid, in an alcohol such as for example ethanol or methanol in order to produce products of formula (Iy) as defined above.

The products of formula (Iy) are therefore products of formula (I) in which the optionally reactive functions are optionally protected and in which Y represents —O— as defined above.

The products of formulae (VIII), (IX), (XII), (XII)$_A$, (XIII), (M$_1$), (M$_2$) and (M$_3$), as defined above can also be subjected according to route c) to the action of a compound of formula (XVI) as defined above in which Y represents the sulphur atom, for a condensation reaction in the presence of a base such as Na$_2$CO$_3$ or NaH in THF or DMF at ambient temperature or while heating: such a condensation reaction can be followed by a salification reaction in the presence of hydrochloric acid for example or also of tartaric, citric or methane sulphonic acid, in an alcohol such as for example ethanol or methanol in order to produce products of formula (Iz) as defined above.

The products of formula (Iz) are therefore products of formula (I) in which the optionally reactive functions are optionally protected and in which Y represents —S— as defined above.

The amine function of the compounds of formulae (Ix), (Iy) and (Iz) as defined above, protected by a group such as Boc or CH$_2$-phenyl can be released under the usual conditions known to a person skilled in the art.

The saponification reaction can be carried out according to the usual methods known to a person skilled in the art, such as for example in a solvent such as methanol or ethanol, dioxane or dimethoxyethane, in the presence of soda or potash.

The reduction or oxidation reactions of the product of formula (Ix) to a product of formula (I) can be carried out according to the usual methods known to a person skilled in the art.

According to the values of R$_1$', R$_2$', R$_5$', R$_6$', R$_3$', Z', D$_1$' and D$_2$', the products of formulae (Ix), (Iy) and (I$_z$) do or do not constitute products of formula (I) and can lead to products of formula (I), or be converted to other products of formula (I) by being subjected to one or more of the reactions a) to k) indicated above.

Thus the various reactive functions which can be carried by certain compounds of the reactions defined above can, if necessary, be protected: these can be for example hydroxyl, acyl, free carboxy or also amino and monoalkylamino radicals which can be protected by the appropriate protective groups.

The following non-exhaustive list of examples of protection of reactive functions can be mentioned:

the hydroxyl groups can be protected for example by alkyl radicals such as tert-butyl, trimethylsilyl, tert-butyldimethylsilyl, methoxymethyl, tetrahydropyrannyl, benzyl or acetyl, the amino groups can be protected for example by acetyl, trityl, benzyl, tert-butoxycarbonyl, benzyloxycarbonyl, phthalimido radicals or other radicals known in peptide chemistry, the acyl groups such as the formyl group can be protected for example in the form of cyclic or non-cyclic ketals or thioketals such as dimethyl or diethylketal or ethylene dioxyketal, or diethylthioketal or ethylenedithioketal, the acid functions of the products described above can be, if desired, amidified by a primary or secondary amine for example in methylene chloride in the presence, for example, of 1-ethyl-3-(dimethylaminopropyl) carbodiimide hydrochloride at ambient temperature:

the acid functions can be protected for example in the form of esters formed with easily cleavable esters such as the benzyl or terbutyl esters or esters known in peptide chemistry.

The reactions to which the products of formulae (Ix), (Iy) and (Iz) as defined above can be subjected, if desired or if necessary, can be carried out, for example, such as indicated hereafter.

a) The products described above can, if desired, be the subject, on the optional carboxy functions, of esterification reactions which can be carried out according to the usual methods known to a person skilled in the art.

b) The optional conversion of ester functions to acid functions of the products described above can, if desired, be carried out under the usual conditions known to a person skilled in the art in particular by acid or alkaline hydrolysis for example by soda or potash in an alcoholic medium such as, for example, in methanol or also by hydrochloric or sulphuric acid.

c) The optional alkylthio groups of the products described above can, if desired, be converted into the corresponding sulphoxide or sulphone functions under the usual conditions known to a person skilled in the art such as for example by peracids such as for example peracetic acid or metachloroperbenzoic acid or also by ozone, oxone, sodium periodate in a solvent such as for example methylene chloride or dioxane at ambient temperature.

Obtaining the sulphoxide function can be encouraged by an equimolar mixture of the product containing an alkylthio group and the reagent such as in particular a peracid.

Obtaining the sulphone function can be encouraged by a mixture of the product containing an alkylthio group with an excess of the reagent such as in particular a peracid.

d) The conversion reaction of a ketone function to an oxime can be carried out under the usual conditions known to a person skilled in the art, such as in particular an action in the presence of an optionally O-substituted hydroxylamine in an alcohol such as for example ethanol, at ambient temperature or while heating.

e) The optional free or esterified carboxy functions of the products described above can be, if desired, reduced to an alcohol function by the methods known to a person skilled in the art: the optional esterified carboxy functions can be, if desired, reduced to an alcohol function by the methods known to a person skilled in the art and in particular by lithium and aluminium hydride in a solvent such as for example tetrahydrofuran or also dioxane or ethyl ether.

The optional free carboxy functions of the products described above can be, if desired, reduced to an alcohol function in particular by boron hydride.

f) The optional alkoxy functions such as in particular methoxy of the products described above can, if desired, be converted to a hydroxyl function under the usual conditions known to a person skilled in the art for example by boron tribromide in a solvent such as for example methylene chloride, by pyridine hydrobromide or hydrochloride or also by hydrobromic or hydrochloric acid in water or trifluoroacetic acid under reflux.

g) The optional alcohol functions of the products described above can, if desired, be converted to aldehyde or acid functions by oxidation under the usual conditions known to a person skilled in the art such as for example by the action of manganese oxide in order to obtain aldehydes or Jones reagent in order to access acids.

h) The optional nitrile functions of the products described above can, if desired, be converted to tetrazolyl under the usual conditions known to a person skilled in the art such as for example by cycloaddition of a metallic azide such as for example sodium azide or trialkyltin azide on the nitrile function as is indicated in the method described in the following reference article:

J. Organometallic Chemistry, 33, 337 (1971) KOZIMA S.& coll.

It should be noted that the conversion reaction of a carbamate to urea and in particular of a sulphonylcarbamate to sulphonylurea, can be carried out for example under reflux of a solvent such as for example toluene in the presence of the appropriate amine.

It is understood that the reactions described above can be carried out as indicated or also, if appropriate, according to other usual methods known to a person skilled in the art.

i) The elimination of protective groups such as for example those indicated above can be carried out under the usual conditions known to a person skilled in the art in particular by acid hydrolysis carried out with an acid such as hydrochloric, benzene sulphonic or paratoluene sulphonic, formic or trifluoroacetic acid or also by catalytic hydrogenation.

The phthalimido group can be eliminated by hydrazine.

A list of different protective groups which can be used will be found for example in Patent BF 2 499 995.

j) The products described above can, if desired, be the subject of salification reactions for example by a mineral or organic acid or by a mineral or organic base according to the usual methods known to a person skilled in the art.

k) The optional optically active forms of the products described above can be prepared by resolution of the racemics according to the usual methods known to a person skilled in the art.

Illustrations of such reactions defined above are given in the preparation of the examples described hereafter.

The products of formula (I) as defined above as well as their addition salts with acids have useful pharmacological properties.

The products of the present invention as defined above, have kinase inhibitory properties of great selectivity.

The cdk's play a central role in the initiation, the development and the completion of the events of the cell cycle and thus, the inhibitory molecules of cdk are capable of limiting undesirable cell proliferations such as those observed in cancers, psoriasis, fungal growth, parasites (animals, protists): such inhibitory molecules of cdk are thus also capable of intervening in the regulation of neurodegenerative diseases such as Alzheimer's disease.

Kinases which are particularly sensitive to the inhibitory effects of the derivatives of the present invention are in particular cdk1, cdk2, cdk4, cdk5 and cdk7.

The products of the present invention are therefore endowed with antimitotic properties.

The products of the present invention have in addition to their specific inhibitory properties of kinases, useful cellular effects such as antiproliferative properties and in particular effects on apoptosis.

It is known from the work described in the literature such as in WO 97/20842, that relationships exist between the cell cycle and apoptosis. Among the routes leading to apoptosis, certain are dependent on kinases.

The products of the present invention are in particular useful for tumour therapy.

The products of the invention can also therefore increase the therapeutic effects of the anti-tumor agents which are currently used.

The products of formula (I) of the present invention therefore have quite particularly antimitotic and anti-neurodegenerative properties.

These properties justify their use in therapeutics and a particular subject the invention is as medicaments, the products of formula (I) as defined above, said products of formula (I) being in all possible racemic, enantiomeric and diastereoisomeric isomer forms, as well as the addition salts with pharmaceutically acceptable mineral and organic acids or with mineral and organic bases of said products of formula A more particular subject of the invention is, as medicaments, the products as defined by formula (Ic):

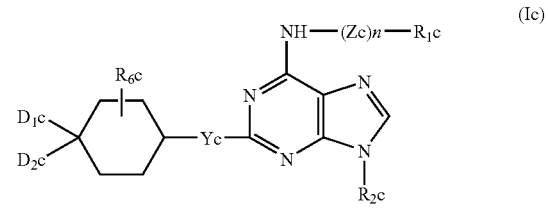

in which:

Zc represents the divalent —$CH_2$—, —$SO_2$—, —CO—, —$(CH_2)_2$—NH—, —$(CH_2)_2$-Nalkyl, —$(CH_2)_2$—N—$CH_2$-phenyl radical in which the phenyl radicals are optionally substituted by a halogen atom, a hydroxyl, trifluoromethyl, alkoxy containing at most 4 carbon atoms or free, salified or esterified carboxy radical, n represents the integer 0 or 1, $R_1c$ is chosen from the hydrogen atom and the phenyl, —$CH_2$-phenyl, —$SO_2$-phenyl, —CO-phenyl, pyridyl, alkyl and —$SO_2$-alkyl radicals, in which the alkyl radicals contain at most 4 carbon atoms and are optionally substituted by a free, salified or esterified carboxy radical, and all the phenyl radicals are optionally substituted by one or more radicals chosen from the halogen atoms and the following radicals: hydroxyl, cyano, nitro, trifluoromethyl, trifluoromethoxy, thioalkyl and alkoxy containing at most 4 carbon atoms, alkyl containing at most 4 carbon atoms optionally substituted by a cyano, —COOH or COOalk radical, the phenyl, tetrazolyl, cycloalkyl radicals interrupted by one or more oxygen or nitrogen atoms, the —SO$_2$NH$_2$ and SO$_2$—NH-thiazolyl radicals, the dioxol, free, esterified or salified carboxy radicals and the —NHR$_4$c and —CONHR$_4$c radicals in which R$_4$c represents a hydrogen atom, an alkyl radical containing at most 4 carbon atoms or a cyclohexyl radical-optionally-substituted by an NH$_2$ radical, R$_2$c represents a linear or branched alkyl radical containing at most 6 carbon atoms, the cyclopentyl, tetrahydrofuryl radicals or the tetrahydrothienyl radical, Yc represents the oxygen atom or the —NH or -Nalkyl radical in which the linear or branched alkyl radical contains at most 4 carbon atoms, D$_1$c and D$_2$c either, identical or different, are chosen from the hydrogen atom, the hydroxyl radical, the linear or branched alkyl and alkoxy radicals containing at most 4 carbon atoms and the —NH$_2$, —NH—COOtBu or —NHalkyl radicals in which the linear or branched alkyl radical contains at most 4 carbon atoms, or together form the =O or =N-Oalkyl radical, in which the linear or branched alkyl radical contains at most 4 carbon atoms, R$_6$c represents the hydrogen atom, a halogen atom or the hydroxyl radical, said products of formula (Ic) being in all possible racemic, enantiomeric and diastereoisomeric isomer forms, as well as the addition salts with mineral and organic acids or with mineral and organic bases of said products of formula (Ic).

A more particular subject of the invention is also as medicaments, the products of formula (I) as defined above by formula (Id):

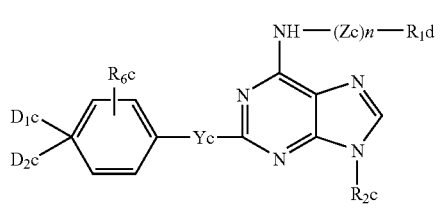

in which:

Zc represents the divalent —CH$_2$—, —SO$_2$—, —CO—, —(CH$_2$)$_2$—NH—, —(CH$_2$)$_2$-Nalkyl, —(CH$_2$)$_2$—N—CH$_2$-phenyl radical in which the phenyl radicals are optionally substituted by a halogen atom, a hydroxyl, trifluoromethyl, alkoxy containing at most 4 carbon atoms or free, salified or esterified carboxy radical, n represents the integer 0 or 1, R$_1$d is chosen from the hydrogen atom and the phenyl, —CH$_2$-phenyl, —SO$_2$-phenyl, —CO-phenyl, alkyl and —SO$_2$-alkyl radicals, in which the alkyl radicals contain at most 4 carbon atoms and are optionally substituted by a free, salified or esterified carboxy radical, and all the phenyl radicals are optionally substituted by one or more radicals chosen from the halogen atoms and the hydroxyl, cyano, nitro, trifluoromethyl, trifluoromethoxy, thioalkyl and alkoxy radicals containing at most 4 carbon atoms, alkyl containing at most 4 carbon atoms optionally substituted by a cyano or free or esterified carboxy radical, the morpholinyl, phenyl, tetrazolyl, —SO$_2$NH$_2$, salified SO$_2$—NH-thiazolyl, dioxol, free, esterified or salified carboxy, —NHR$_4$c and —CONHR$_4$c radicals in which R$_4$c represents a hydrogen atom, an alkyl radical containing at most 4 carbon atoms or a cyclohexyl radical optionally substituted by an NH$_2$ radical, R$_2$c represents a linear or branched alkyl radical containing at most 6 carbon atoms, the cyclopentyl, tetrahydrofuryl radicals or the tetrahydrothienyl radical, Yc represents the oxygen atom or the —NH or —N-alkyl radical in which the linear or branched alkyl radical contains at most 4 carbon atoms, D$_1$c and D$_2$c either, identical or different, are chosen from the hydrogen atom, the hydroxyl radical, the linear or branched alkyl and alkoxy radicals containing at most 4 carbon atoms and the —NH$_2$, —NH—COOtBu or —NH-alkyl radicals in which the linear or branched alkyl radical contains at most 4 carbon atoms, or together form the =O or =N-Oalkyl radical, in which the linear or branched alkyl radical contains at most 4 carbon atoms, R$_6$c represents the hydrogen atom, a halogen atom or the hydroxyl radical, said products of formula (Id) being in all possible racemic, enantiomeric and diastereoisomeric isomer forms, as well as the addition salts with mineral and organic acids or with mineral and organic bases of said products of formula (Id).

A quite particular subject of the invention is, as medicaments, the products described hereafter in the examples and in particular the products of formula (I) as defined above, corresponding to the following formulae:

Dihydrochloride of butyl trans-4-[[[2-[(4-aminocyclohexyl)-amino]-9-cyclopentyl-9H-purin-6-y]-amino]-methyl]-benzoate, Dihydrochloride of ethyl trans-4-[[2-[(4-aminocyclohexyl)-amino]-9-cyclopentyl-9H-purin-6-yl]-amino]-benzoate, trans-N2-(4-aminocyclohexyl)-9-cyclo-pentyl-N6-[2-[(phenylmethyl)-amino]-ethyl]-9H-purin-2,6-diamine trihydrochloride, trans-N2-(4-aminocyclohexyl)-N6-(2-aminoethyl)-9-cyclopentyl-9H-purin-2,6-diamine trihydrochloride, trans-N2-(4-aminocyclohexyl)-9-cyclo-pentyl-N6-[2-[[(4-methoxyphenyl)-methyl]-amino]-ethyl]-9H-purin-2,6-diamine trihydrochloride, trans-N2-(4-aminocyclohexyl)-N6-[2-[[[4-chloro-3-(trifluoromethyl)-phenyl]-methyl]-amino]-ethyl]-9-cyclopentyl-9H-purin-2,6-diamine trihydrochloride, trans-N2-(4-aminocyclohexyl)-9-cyclo-pentyl-N6-[(diphenylmethyl)-amino]-ethyl]-9H-purin-2,6-diamine trihydrochloride, trans-N2-(4-aminocyclohexyl)-N6-[2-[[(4-chlorophenyl)-methyl]-amino]-ethyl]-9-cyclopentyl-9H-purin-2,6-diamine trihydrochloride, Dihydrochloride of ethyl trans(.+−.)-4-[[2-[(4-aminocyclohexyl)-amino]-9-(tetrahydro-3-thienyl)-9H-purin-6-yl]-amino]-benzoate, trans(.+−.)-N2-(4-aminocyclohexyl)-9-(tetrahydro-3-thienyl)-N6-[4-(trifluoromethoxy)-phenyl]-9H-purin-2,6-diamine dihydrochloride, trans(.+−.)-N2-(4-aminocyclohexyl)-9-(tetrahydro-3-furanyl)-N6-[(4-trifluoromethoxy)-phenyl]-9H-purin-2,6-diamine dihydrochloride, trans-N2-(4-aminocyclohexyl)-9-(1-ethyl-propyl)-N6-[4-(trifluoromethoxy)-phenyl]-9H-purin-2,6-diamine dihydrochloride, Dihydrochloride of ethyl trans-4-[[2-[(4-aminocyclohexyl)-amino]-9-(1-ethylpropyl)-9H-purine-6-yl]-amino]-benzoate.

A quite particular subject of the present invention is also, as medicaments, the products of formula (I) as defined above, corresponding to the following formulae:

Dihydrochloride of ethyl trans-3-[[2-[(4-aminocyclohexyl)-amino]-9-cyclopentyl-9H-purin-6-yl]-amino]-benzoate, trans-N2-(4-aminocyclohexyl)-9-cyclopentyl-N6-[2-[[(3,4-dichlorophenyl)-methyl]-amino]-ethyl]-9H-purine-2,6-diamine trichlorhydrate, trans-N2-(4-aminocyclohexyl)-9-cyclopentyl-N6-[2-[[(3,5-dichlorophenyl)-methyl]-amino]-ethyl]-9H-purine-2,6-diamine trichlorhydrate, trans-4-[[2-[(4-aminocyclohexyl)-amino]-9-cyclopentyl-9H-purin-6-yl]amino]benzeneacetonitrile dihydrochloride, trans-N2-(4-aminocyclohexyl)-9-cyclopentyl-N6-[4-(4-morpholinyl)-phenyl]-9H-purine-2,6-diamine dihydrochloride, trans-4-[[2-[(4-aminocyclohexyl)-amino]-9-cyclopentyl-9H-purin-6-yl]amino]-benzonitrile dihydrochloride, Dihydrochloride of trans-N2-(4-aminocyclohexyl)-9-cyclopentyl-N6-(4-nitrophenyl)-9H-purine-2,6-diamine, trans-N2-(4-aminocyclohexyl)-N6-(4-aminophenyl)-9-cyclopentyl-9H-purine-2,6-diamine dihydrochloride, trans-N2-(4-aminocyclohexyl)-9-cyclopentyl-N6-(4-methoxyphenyl)-9H-purine-2,6-diamine dihydrochloride, Dihydrochloride of diethyl trans-5-[[2-[(4-amino-cyclohexyl)-amino]-9-cyclopentyl-9H-purin-6-yl]-amino]-1,3-benzenedicarboxylate.

The medicaments, which are a subject of the invention, are of use, for example, as antimitotics, in the chemotherapy of cancers, or also in the treatment of psoriasis, of parasitosis such as those caused by protists or fungi or also in the treatment of Alzheimer's disease or in the treatment of neuronal apoptosis.

The invention extends to the pharmaceutical compositions containing at least one of the medicaments defined above as active ingredient.

Such pharmaceutical compositions according to the present invention can also, if appropriate, contain the active ingredients of other antimitotic medicaments such as in particular those based on taxol, cisplatin, DNA intercalating agents and others.

These pharmaceutical compositions can be administered by buccal route, by parenteral route or by local route as a topical application on the skin and mucous membranes or by injection by intravenous or intramuscular route.

These compositions can be solids or liquids and be presented in all the pharmaceutical forms commonly used in human medicine, such as for example, plain or sugar-coated tablets, pills, lozenges, gelatin capsules, drops, granules, injectable preparations, ointments, creams, gels; they are prepared according to the usual methods. The active ingredient can be incorporated with the excipients usually used in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The dose administered is variable according to the product used, the patient treated and the illness in question and can be, for example, from 0.05 to 5 g per day in an adult, or preferably from 0.1 to 2 g per day.

The starting product of formula (II) i.e. dichloro-2,6-purine is known and commercially available.

Among the starting products of formulae (III), (V), (VI), (VII), (XI), (XI)$_A$, (XIV), (XV) and (XVI), some are known and can be obtained commercially or can be prepared according to the usual methods known to a person skilled in the art.

Among the commercial starting products of formulae (III), (V), (VI), (VII), (XI), (XI)$_A$, (XIV), (XV) and (XVI), there can be mentioned for example, the following products of formula (III): cyclopentanol, 3-hydroxytetrahydrofuran, 3-propanol, 3-hydroxythiophene or also 2-butanol.

Among the commercial products of formula (V), there can be mentioned the hydrochloride product of methyl 4-(aminomethyl)-benzoate, ethyl-4-aminobenzoate, 4-aminobenzamide, methyl-3-aminobenzoate or also 3-aminobenzamide.

As commercial products of formula (XIV), there can be mentioned trans-1,4-diaminocyclohexane or also trans-4-aminocyclohexanol.

In particular certain starting products can also be prepared from commercial products for example by subjecting them to one or more of the reactions described above in a) to 1), carried out under the conditions also described above.

There can also be mentioned by way of example:

as product of formula (VI), phenylsulphonamide, 3-bromophenylsulphonamide, 4-terbutylphenylsulphonamide, as product of formula (VII), ethylenediamine, as product of formula (XI) isopropylsulphonyl chloride, paramethoxyphenylsulphonyl chloride or also trifluoromethanesulphonyl chloride, as product of formula (XI)$_A$, 4-trifluoromethylbenzoyl chloride, 4-anisoyl chloride, 4-chlorobenzoyl chloride, 2-chloro-4-nitro-benzoyl chloride, as product of formula (XVII), benzaldehyde, paramethoxybenzaldehyde or also paracyanobenzaldehyde.

The experimental part hereafter gives examples of such starting products.

Finally a subject of the present invention is as new industrial products, the compounds of formulae (VIII), (IX), (X), (XII), (XII)$_A$, (XIII), ($M_1$), ($M_2$) and ($M_3$)

Therefore a particular subject of the invention is the pharmaceutical compositions containing at least one of the medicaments as defined above as active ingredient.

A quite particular subject of the invention is the pharmaceutical compositions as defined above characterized in that they are used as antimitotic medicaments, in particular for the chemotherapy of cancers, or also for the treatment of psoriasis, parasitosis such as those caused by fungi or protists or also Alzheimer's disease A quite particular subject of the invention is also the pharmaceutical compositions as defined above characterized in that they are used as antineurodegenerative medicaments in particular neuronal anti-apoptosis.

In particular a subject of the invention is the use of the products of formula (I) as defined above for the preparation of medicaments intended for the chemotherapy of cancers, for the treatment of psoriasis, parasitosis such as those caused by fungi or protists or for the treatment of Alzheimer's disease or for the treatment of neurodegenerative diseases in particular neuronal apoptosis.

The following examples illustrate the invention without however limiting it.

EXAMPLE 1

Dihydrochloride of butyl trans-4-[[[2-[(4-aminocyclohexyl)-amino]-9-cyclopentyl-9H-purin-6-yl]-amino]-methyl]-benzoate Stage 1: 9-cyclopentyl-2,6-dichloro-9H-purine 378 mg of dichloro-2,6-purine, 5 ml of tetrahydrofuran, 0.27 ml of cyclopentanol, 787 mg of triphenylphosphine (P(phenyl)3) and 0.46 ml of DEAD (diethylazodicarboxylate) are mixed together and the reaction medium is agitated overnight at ambient temperature then evaporated to dryness. The crude product is purified by chromatography on a silica column eluting with CH2Cl2 50, AcOEt 25, Cyclohexane 25. In this way 400 mg of expected product is obtained.

| NNR in CDCl$_3$ | | |
| --- | --- | --- |
| 1.80 to 2.10 (m) | } 6H | the CH$_2$'s of the cyclopentyl |
| 2.35 (m) | } 2H | |
| 4.98 (m) | =C—N—C$\underline{H}$—CH$_2$ | |
| 8.15 (s) 8.16 (s) | —C$\underline{H}$=N | |
| IR spectrum CHCl$_3$ | | |
| 1591; 1557; 1491 cm−1 | heterocycle | |
| 1747 cm−1 | C=O | |

Stage 2: methyl 4-[[(2-chloro-9-cyclopentyl-9H-purin-6-yl)-amino]-methyl]-benzoate 450 mg of the product obtained in Stage 1 above, 10 ml of butanol, 347 mg of methyl 4-(aminomethyl)-benzoate hydrochloride and 290 mg of potassium carbonate are mixed together, and the reaction medium is agitated at a temperature of approximately 100° C. for approximately 18 hours then left to return to ambient temperature.

Then 15 ml of H$_2$O is added, followed by extracting with 2×50 ml of CH$_2$Cl$_2$ (methylene chloride), drying, filtering, evaporating, then impasting in the isopropyl ether and drying under vacuum at approximately 50° C. In this way 526 mg of expected product is obtained in the form of colourless crystals.

IR spectrum CHCl$_3$
NH 3424 cm−1
>=O 1720 cm−1
heterocycle and aromatic 1619; 1575; 1528; 1499 cm−1

Stage 3: Dihydrochloride of butyl trans-4-[[[2-[(4-aminocyclohexyl)-amino]-9-cyclopentyl-9H-purin-6-yl]-amino]-methyl]-benzoate 50 mg of the product obtained in Stage 2 above, 4 ml of butanol, 150 mg of trans-1,4-diaminocyclohexane are mixed together, the reaction medium is heated to approximately 150° C. for approximately 24 hours, left to return to ambient temperature. Then 4 ml of ether is added, followed by separating and rinsing with ether, then drying at ambient temperature.

After taking up in 4 ml of ethanol, 2 ml of HCl (hydrochloric acid) at 1.4N in ethanol is added followed by evaporating. In this way 25 mg of expected product is obtained.

| NMR in DMSO | |
| --- | --- |
| 0.92 (t) | |
| 1.40 (m) | |
| 1.67 (m) | |
| 4.23 (t) | O—C= |
| 1.20 to 3.10 | the C—C$\underline{H_2}$ |
| 3.60 (masked) | =C—N—CH + NH$_3$—C$\underline{H}$ |
| 4.75 (m) | phenyl-N—C$\underline{H}$ |
| 4.85 (bs) | phenyl-C$\underline{H_2}$—N—C= |
| 7.55 to 7.90 AA'BB' | =C-phenyl-O |
| 8.32 (bs) | N=C—C$\underline{H}$—N |

EXAMPLE 2 trans(.+−.)-N2-(4-amino-cyclohexyl)-N6-(phenylmethyl)-9-(tetrahydro-3-furanyl)-9H-purine-2,6-diamine dihydrochloride Stage 1: (.+−.)-2,6-dichloro-9-(tetrahydro-3-furanyl)-9H-purine 945 mg of dichloro-2,6-purine, 660 mg of 3-hydroxytetrahydrofuran, 7.96 g of triphenylphosphine (P(phenyl)3), 20 ml of tetrahydrofuran are mixed together then 1.16 g of DEAD (diethylazodicarboxylate) is added over 10 minutes and the reaction medium is agitated overnight at ambient temperature and poured into an 1M aqueous solution of NaH$_2$PO$_3$. Then extraction is carried out 3 times with 20 ml of ethyl acetate, followed by washing with 20 ml of water, then with 10 ml of a saturated aqueous solution of NaCl, drying and evaporating to dryness.

After chromatography on silica eluting with methylene chloride/ethyl acetate/CH$_3$CN in a proportion of 70/15/15 then a second chromatography on silica eluting with methylene chloride/ethyl acetate in a proportion of 50/50, in this way 878 mg of expected product is obtained in the form of white crystals.

| NMR in DMSO | |
|---|---|
| 2.21(m) 1H ⎫ 2.67(m) 1H ⎭ | central CH$_2$'s |
| 4.02(m) ⎫ 4.16(m) 1H ⎭ | O—C$\underline{H}_2$—CH— |
| 4.02(m) ⎫ 4.24(m) 1H ⎭ | O—C$\underline{H}_2$—CH$_2$ |
| 5.38(m) 1H | CH$_2$—C$\underline{H}$—N |
| 8.26 1H | H$_2$ |

Stage 2: (.+−.)-2-chloro-N-(phenylmethyl)-9-(tetrahydro-3-furanyl)-9H-purin-6-amine 139 mg of the product obtained in Stage 1 above, 2 ml of butanol and 0.06 ml of benzylamine are mixed together and the reaction medium is heated to a temperature of approximately 95° C. for 5 hours 30. The reaction medium is then left to return to ambient temperature and to crystallize, followed by separating, washing with 10 ml of isopropanol and drying under vacuum at approximately 50° C. In this way 157 mg of expected product is obtained in the form of white crystals.

| NMR in DMSO | |
|---|---|
| 2.15(m) 1H ⎫ 2.60(m) 1H ⎭ | CH$_2$ in 4' |
| 3.97(m) ⎫ 4.08(bd) ⎭ | CH$_2$ in 2' |
| 3.97(m) ⎫ 4.17(m) ⎭ | CH$_2$ in 5' |
| 4.83(broad s) | NH—C$\underline{H}_2$-phenyl |
| 6.50(broad) | N$\underline{H}$—CH$_2$-phenyl |
| 5.30(m) | H$_3$' |
| 7.25 to 7.40(m) | aromatic 5H |
| 7.84(s) | H$_2$ |

Stage 3: trans(.+−.)-N2-(4-aminocyclo-hexyl)-N6-(phenyl-methyl)-9-(tetrahydro-3-furanyl)-9H-purine-2,6-diamine dihydrochloride 656 mg of trans-1,4-diaminocyclohexane and 133 mg of the product obtained in Stage 2 above are mixed together and the reaction medium is taken to a temperature of 130 to 150° C. for approximately 5 hours then left overnight at ambient temperature. Then the reaction medium is taken up in 10 ml of water and 20 ml of ethyl acetate and left to settle, followed by re-extracting with 2×5 ml of ethyl acetate, washing with 10 ml of water and 10 ml of saturated aqueous solution of sodium chloride, drying and evaporating to dryness. After purification on silica eluting with methanol/ammonium hydroxide (NH$_4$OH) in a proportion of 98/2, 1.5 ml of hydrochloric acid at 1.4 N in ethanol is added and the reaction medium is left to crystallize. After diluting with 2 ml of ethyl acetate and leaving for one hour at ambient temperature, separation is carried out, followed by washing with 5 ml of ethyl acetate and drying at a temperature of approximately 50° C. In this way 98 mg of expected product is obtained in the form of white/cream crystals.

| NMR in DMSO | |
|---|---|
| 1.40(m) 4H | the axial H of the cyclohexyl |
| 2.04(d) 4H | the equatorial H of the cyclohexyl |
| 2.30(m) 1H ⎫ 2.50 (masked) ⎭ | CH—C$\underline{H}_2$—CH$_2$—O |
| 3.02(broad m,) 1H | axial H$_4$ |
| 3.72(broad t,) 1H | axial H$_1$ |
| 3.87(m) 1H ⎫ 4.10(q) 1H ⎭ | CH$_2$—C$\underline{H}_2$—O—CH$_2$ |
| 3.99(d) 2H | CH$_2$—CH$_2$—O—C$\underline{H}_2$ |
| 4.90(broad s) | NH—C$\underline{H}_2$-phenyl |
| 5.08(m) 1H | NH—C$\underline{H}_2$— CH$_2$—O |
| 7.26(m) 1H | |
| 7.34(m) 2H | aromatic |
| 7.43(m) 2H H | |
| 8.08(bs) >2H | NH$_2$ (salified) |
| 8.23(s) 1H | N=C$\underline{H}$—N |
| 9.39 1H | mobile |

EXAMPLE 3 trans-N2-(4-aminocyclohexyl)-9-(1-ethylpropyl)-N6-(phenylmethyl)-9H-purine-2,6-diamine (2R,3S)-2,3-dihydroxybutanedioate STADE 1: 2,6-dichoro-9-(1-ethylpropyl)-9H-purine.

1.32 mg of dichloro-2,6-purine, 2.75 g of triphenylphosphine (P(phenyl)3), 35 ml of tetrahydrofuran, 1.13 ml of 3-pentanol (10.5 mmoles) are mixed together, the reaction medium is agitated at ambient temperature and 1.63 ml of DEAD (diethylazodicarboxylate) (10.5 mM) is added over 15 minutes and agitation is carried out for approximately 20 hours at ambient temperature, followed by pouring into a 1M aqueous solution of NaH$_2$PO$_4$, extracting 3 times with 10 ml of ethyl acetate, washing with 10 ml of water then with 10 ml of a saturated aqueous solution of sodium chloride, drying and evaporating to dryness. After chromatography on silica eluting with methylene chloride/ethyl acetate in a proportion of 90/10, then a second chromatography on silica with the same eluent, 1.12 g of expected product is obtained thus in the form of white crystals.

Stage 2: 2-chloro-9-(1-ethylpropyl)-N-(phenylmethyl)-9H-purin-6-amine 191 mg of the product obtained in Stage 1 above, 2.5 ml of butanol and 0.115 ml of benzylamine are mixed together and the reaction medium is heated to a temperature of approximately 90 to 110° C. for 5 hours. The reaction medium is then left to return to ambient temperature and left to crystallize, followed by separating, washing with 10 ml of isopropanol and drying under vacuum at approximately 50° C. In this way 148 mg of expected product is obtained in the form of white crystals.

Stage 3: trans-N2-(4-aminocyclohexyl)-9-(1-ethyl-propyl)-N6-(phenylmethyl)-9H-purine-2,6-diamine (2R,3S)-2,3-dihydroxybutanedioate 456 mg of trans-1,4-diaminocyclohexane and 131 mg of the product obtained in Stage 2 above are mixed together and the reaction medium is taken to a temperature of 140 to 150° C. for 4 hours then left to return to ambient temperature. After diluting with 5 ml of water and 5 ml of ethyl acetate, the reaction medium is left to settle, followed by re-extracting with 2×10 ml of ethyl acetate, washing with 10 ml of water and 5 ml of an aqueous solution of sodium chloride, drying and evaporating to dryness. After purification on silica eluting with methanol/ammonium hydroxide ($NH_4OH$) in a proportion of 98/2, followed by salifying with a 1M solution of mesotartaric acid in ethanol, leaving to crystallize overnight at ambient temperature, separating, washing with 10 ml of ethyl acetate and drying at a temperature of approximately 50° C. In this way 97 mg of expected product is obtained in the form of beige pink crystals.

| NMR in DMSO | |
| --- | --- |
| 0.70(t) 6H | ($C\underline{H}_3$—$CH_2$)$_2$—CH |
| 1.81(m) 4H | ($CH_3$—$C\underline{H}_2$)$_2$—CH |
| 1.22(m) | |
| 1.37(m) 4H | the axial H of the cyclohexyl |
| 1.92(d) | the equatorial H of the cyclohexyl |
| 2.95(t) | axial $H_4$ |
| 3.57(broad m,) | axial $H_1$ |
| 3.87(s) 2H | NH—$C\underline{H}_2$-phenyl |
| 4.04(m) 1H | =C—N—C$\underline{H}$ |
| 7.20 } | |
| 7.29 } | aromatic H |
| 7.36 } | |
| 7.85(s) 1H | N—C$\underline{H}$—N= |
| 6.16(d) 1H | N$\underline{H}$—CH |
| 7.85(bs) } | mobile H's |
| 4.59(bs) } | |

EXAMPLE 4 trans-9-cyclopentyl-N2-(4-hydroxycyclohexyl)-N6-(phenylmethyl)-9H-purine-2,6-diamine hydrochloride

Stage 1: 2-chloro-9-cyclopentyl-N-(phenylmethyl)-9H-purin-6-amine.

1.03 g of the product obtained in Stage 1 of Example 1 above, 15 ml of butanol and 0,54 ml of benzylamine are mixed together and the reaction medium is heated to a temperature of approximately 90 to 100° C. for 4 hours. The reaction medium is then left to return to ambient temperature and left overnight. After diluting with 10 ml of isopropanol, the reaction medium is left for one hour at ambient temperature, followed by separating, washing with 20 ml of isopropanol and drying under vacuum at approximately 50° C. After purification on silica eluting with methylene chloride/ethyl acetate in a proportion of 90/10, then recrystallization from a minimum amount of isopropanol and drying under vacuum at approximately 50° C., 114 mg of expected product is obtained in the form of white crystals.

Stage 2: trans-9-cyclopentyl-N2-(4-hydroxy-cyclohexyl)-N6-(phenylmethyl)-9H-purine-2,6-diamine hydrochloride 1 g of trans-1,4-aminocyclohexanol is mixed which is then taken to a temperature of 50 to 60° C. and 212 mg of the product obtained in Stage 1 above is added and taken to a temperature of 140 to 150° C. for approximately 4 hours. The reaction medium is then left to return to a temperature of 100° C., 10 ml of water is added, the reaction medium is left to settle, 10 ml of water, 20 ml of ethyl acetate are added and the medium is taken to a temperature of approximately 70° C. Then 10 ml of water is added and the reaction medium is left overnight at ambient temperature, then left to settle, followed by re-extracting with 2×20 ml of methylene chloride with 20% of methanol, combining the organic phases, washing with 10 ml of water and 10 ml of an aqueous solution of sodium chloride, drying and evaporating to dryness. The residue is then dissolved in the minimum amount of ethanol, 1.4N hydrochloric acid in ethanol is added and the reaction medium is left to crystallize, followed by diluting in 5 ml of ethanol then leaving for one hour at ambient temperature, separating, washing with 10 ml of ethanol and drying at a temperature of approximately 50° C. In this way 215 mg of expected product is obtained in the form of white crystals.

| NMR in DMSO | |
| --- | --- |
| 1.30(m) 4H | the central axial H of the cyclohexyl |
| 1.70(m) 2H | |
| 1.80 to 2.10 | |
| 2.18(m) 2H | the $CH_2$'s of the cyclopentyl |
| 1.80 to 2.10 | the central equatorial H of the cyclohexyl |
| 3.45(broad m,) 1H | axial $H_4$ |
| 3.71(broad m,) 1H | axial $H_1$ |
| 4.75(m) 1H | —CH cyclopentyl |
| 4.89(s, broad) 2H | N—$C\underline{H}_2$-phenyl |
| 7.26(m) 1H | |
| 7.33(m) 2H } | aromatic H |
| 7.43(d) 2H | |
| 8.28 | =N—C$\underline{H}$=N |
| 9.41 to 5.94 1H | mobile |

EXAMPLE 5 trans(.+−.)-N2-(4-amino-cyclohexyl)-N6-(phenylmethyl)-9-(tetrahydro-3-thienyl)-9H-purine-2,6-diamine dihydrochloride

Stage 1: 2,6-dichloro-9-(tetrahydro-3-thienyl)-9H-purine.

312 mg of 3-hydroxythiophene, 380 mg of 2,6-dichloro-purine, 6 ml of tetrahydrofuran, 786 mg of triphenylphosphine (P(phenyl)3) are mixed together at ambient temperature then 0.47 ml of DEAD (diethyl-azodicarboxylate) is added over 10 minutes and agitation is carried out overnight at ambient temperature. Then 10 ml of $NaH2PO4$ in aqueous solution 1M is added, followed by extracting 3 times with 10 ml of methylene chloride, washing with 10 ml of water with 5 of an aqueous solution of sodium chloride, drying and evaporating to dryness. After purification on silica eluting with methylene chloride/ethyl acetate in a proportion of 75/25 then 90/10, impasting is carried out at ambient temperature in 5 ml of isopropyl ether, followed by separating, washing with 5 ml of isopropyl ether and drying at ambient temperature. In this way 137 mg of expected product is obtained in the form of white crystals.

Stage 2: 2-chloro-N-(phenylmethyl)-9-(tetrahydro-3-thienyl)-9H-purin-6-amine 120 mg of the product obtained in Stage 1 above, 2 ml of butanol and 0,105 ml of benzylamine are mixed together and the reaction medium is heated to a temperature of approximately 95 to 100° C. for 10 hours. It is then left to return to ambient temperature and diluted with 5 ml of isopropanol, followed by separating, washing with 5 ml of isopropanol and drying under vacuum at approximately 30° C. In this way 132 mg of expected product is obtained in the form of white crystals.

Stage 3: trans(.+−.)-N2-(4-amino-cyclohexyl)-N6-(phenylmethyl)-9-(tetrahydro-3-thienyl)-9H-purine-2,6-diamine dihydrochloride 400 mg of trans-1,4-diaminocyclohexane is taken to a temperature of 60 to 70° C., then 119 mg of the product obtained in Stage 2 above is added and the reaction medium is taken to a temperature of 130 to 140° C. for 3 hours, then left to return to ambient temperature, 5 ml of water is added followed by extracting with 3×10 ml of ethyl acetate, washing with 10 ml of water and 5 ml of an aqueous solution of sodium chloride, drying and evaporating to dryness. After purification on silica eluting with methanol/ammonium hydroxide (NH4OH) in a proportion of 98/2, followed by salification with 1.4N hydrochloric acid in ethanol, leaving to crystallize for 2 days at ambient temperature, separating, washing with 10 ml of ethanol and drying at a temperature of approximately 50° C. In this way 112 mg of expected product is obtained in the form of crystals white/cream.

| NMR in DMSO | |
|---|---|
| 1.37(m) 1.53(m) | 4H the axial H's of the cyclohexyl |
| 2.04(d) 4H | the equatorial H's of the cyclohexyl |
| 2.45 2.55(masked) | —S—$CH_2$—$CH_2$—CH |
| 2.97(m) 3.02(masked) | —S—$CH_2$—$CH_2$—CH assumed axial $H_4$ |
| 3.32(m) 3.24(m) 2H | —S—$CH_2$—CH |
| 3.73(t) 1H | axial $H_1$ |
| 4.90(s,l) | NH—$CH_2$-phenyl |
| 5.07(m) 1H | N=$CH_2$—N—CH— |
| 7.27(m) 1H 7.35(m) 2H 7.43(m) 2H | aromatic H |
| 8.33(s) 1H | N=CH—N |
| 8.11(bs) 9.49(bs) | mobile H's |

EXAMPLE 6

Dihydrochloride of ethyl trans-4-[[2-[(4-aminocyclohexyl)-amino]-9-cyclopentyl-9H-purin-6-yl]amino]-benzoate

Stage 1: ethyl 4-[(2-chloro-9-cyclopentyl-9H-purin-6-yl)amino]-benzoate 86 mg of the product obtained in Stage 1 of Example 1, 2 ml of nbutanol and 66 mg of ethyl-4-aminobenzoate are introduced at ambient temperature and the reaction medium is immersed in a bath at a temperature of approximately 100° C. for 7 hours under agitation then left to return to ambient temperature, followed by separating and rinsing with ether then drying under vacuum. In this way 74 mg of expected product is obtained in the form of a beige powder.

| NMR in DMSO | |
|---|---|
| 1.33(t) 3H | —CO—$CH_2$—$CH_3$ |
| 4.30(a) 2H | —CO—$CH_2$—$CH_3$ |
| 1.72(m) 2H | |
| 1.89(m) 2H | |
| 2.01(m) 2H | |
| 2.18(m) 2H | $CH_2$ of the cyclopentyl |
| 4.88(q) 1H | $CH_2$—CH—N |
| 7.95 2H 8.05 2H | AA' BB' N-phenyl-CO |
| 8.53(s) 1H | CH of the purine ring |
| 10.69 | NH |

Stage 2: Dihydrochloride of ethyl trans-4-[[2-[(4-aminocyclohexyl)-amino]-9-cyclopentyl-9H-purin-6-yl]amino]-benzoate 1.14 g of trans-1,4-diaminocyclohexane is taken to approximately 150° C. then 386 mg of the product obtained in Stage 1 above is added: the reaction medium is left under agitation for 3 hours 30 minutes then left to return to ambient temperature. Then 10 ml of water is added, followed by separating, washing with water, drying at a temperature of approximately 50° C. and taking up in 110 mg in 10 ml of methanol. 4 ml of 1.4N HCl in ethanol is added followed by concentrating to ~4 ml, leaving to crystallize, separating and washing with ethanol then drying at a temperature of approximately 50° C. In this way 110 mg of expected product is obtained in the form of beige powder.

| NMR in DMSO | |
|---|---|
| 1.32(t) | $CO_2$—$CH_2$—$CH_3$ |
| 4.31(q) | $CO_2$—$CH_2$—$CH_3$ |
| 1.39(m) | |
| 1.52(m) 2.10(m) | axial $CH_2$ of the cyclohexyl |
| 2.06(m) | equatorial $CH_2$ of the cyclohexyl |
| 3.03(b) | |
| 3.68(bt) | trans isomer axial H of the cyclopentyl |
| 4.85(b) | —N—CH of the cyclopentyl |
| 2.16(m) | $CH_2$ in alpha position of the cyclopentyl |
| 1.70 and 1.90(m) | $CH_2$ in beta position of the cyclopentyl |
| 7.98(d) 2H | |

-continued

| NMR in DMSO | |
|---|---|
| 8.18 masked 5H AA' BB'<br>7.58-9.28-11.13 | —NH-phenyl-C= + —N=CH— + —NH$_2$<br>mobile absorptions |

EXAMPLE 7 trans-N2-(4-aminocyclohexyl)-9-cyclopentyl-N6-[2-[(phenylmethyl)-amino]-ethyl]-9H-purine-2,6-diamine trihydrochloride

Stage 1: N-(2-aminoethyl)-2-chloro-9-cyclopentyl-9H-purin-6-amine.

3 g of the product obtained in Stage 1 of Example 1, 21 ml of butanol, 7.5 ml of 1,2-ethanediamine are mixed together and the reaction medium is taken to 75° C. for 3 hours. The solvent is evaporated off and after chromatography on silica eluting with methylene chloride/methanol/ammonium hydroxide in a proportion of 85/15/1.5, 2.73 g of expected product is obtained in the form of a yellow resin.

IR spectrum CHCl$_3$
NH 3423 cm−1

>=O 1685 cm−1 heterocycle 1619; 1576; 1530; 1498 cm−1

Stage 2: 2-chloro-9-cyclopentyl-N-[2-[(phenylmethyl)-amino]-ethyl]-9H-purin-6-amine 141 mg of the product obtained in Stage 1 above, 2 ml of methanol, 0.07 ml of benzaldehyde, 0.1 ml of acetic acid and 0.055 g of NaBH$_3$CN are mixed together and the reaction medium is left at ambient temperature for approximately 4 hours. 10 ml AcOEt is added, followed by washing with 2×5 ml H$_2$O, then with 5 ml of a saturated aqueous solution of NaCl, drying and evaporating the solvent. After chromatography on silica eluting with CH$_2$Cl$_2$/methanol/ammonium hydroxide in a proportion of 90/10/1, 100 mg of expected product is obtained.

Stage 3: trans-N2-(4-aminocyclohexyl)-9-cyclopentyl-N6-[2-[(phenylmethyl)-amino]-ethyl]-9H-purine-2,6-diamine trihydrochloride The operation is carried out as in Stage 3 of Example 1 starting from 0.090 g of the product obtained in Stage 2 above, 277 mg of trans-1,4-diaminocyclohexane, then the reaction medium is heated to approximately 140° C. for 2 hours and purified on a silica cartridge with CH$_2$Cl$_2$/methanol/ammonium hydroxide in a proportion of 85/15/1.5. The product is salified with a 1.4N solution of HCl in EOOH. In this way 70 mg of expected product is obtained.

| NMR in DMSO | |
|---|---|
| 1.34(m) 2H<br>1.48(m) 2H | the axial H of the cyclohexyl |
| 1.70(m)<br>1.90(m)<br>2.04(m)<br>2.14(m) | the CH$_2$'s of the cyclopentyl<br>+ the equatorial CH$_2$'s of the cyclohexyl |
| 3.03(bs) | axial H$_4$ |
| 3.93(bs) | axial H$_1$ |
| 3.23(bs)<br>3.67(assumed masked)<br>4.23(bs) | the CH$_2$—N's |
| 4.75(m) | CH of the cyclopentyl |
| 7.42(m) | |
| 7.56(m) | -phenyl- |
| 8.14(s)<br>7.97 | N—CH—N |
| 8.33<br>9.26 | assumed mobile H's |

EXAMPLE 8 trans-N-[2-[(4-aminocyclo-hexyl)-amino]-9-cyclopentyl-9H-purin-6-yl]-benzene-sulphonamide dihydrochloride

Stage 1: N-[[2-chloro-9-cyclopentyl-9H-purin-6-yl]-amino]-benzenesulphonamide.

257 mg of the product obtained in Stage 1 of Example 1 above, 4 ml of dimethoxyethane (DME), 157 mg of benzenesulphonamide and 390 mg of caesium carbonate (Cs$_2$CO$_3$) are mixed together and the reaction medium is agitated at a temperature of approximately 100° C. for 2 hours. 4 ml of 2N hydrochloric acid and 4 ml of water is added, followed by extracting with 30 ml of ethyl acetate, drying, filtering, evaporating to dryness, impasting in 5 ml of ether and drying under vacuum at approximately 50° C. In this way 237 mg of expected product is obtained in the form of beige crystals.

Stage 2: trans-N-[2-[(4-aminocyclohexyl)-amino]-9-cyclopentyl-9H-purin-6-yl]-benzenesulphonamide dihydrochloride 570 mg of trans-1,4-diaminocyclohexane is taken to a temperature of approximately 140° C. then 188 mg of the product obtained in Stage 1 above is added and the reaction medium is left at this temperature for approximately 5 hours, then left to return to ambient temperature. 10 ml of water is added, followed by separating and drying under vacuum at a temperature of approximately 50° C. After chromatography on silica eluting with methylene chloride/methanol/ammonium hydroxide in a proportion of 70/30/1, impasting in 5 ml of ether and drying at a temperature of approximately 50° C. are carried out. In this way 40 mg of expected product is obtained in the form of brown crystals.

| NMR in DMSO | |
|---|---|
| 1.32(m) 2H<br>1.48(m) 2H } | the axial H's of the cyclohexyl |
| 1.67(m) 2H<br>1.87(m) 2H<br>2.04(masked)<br>3.04(bs) 1H<br>3.56(bt) 1H<br>4.70(m) 1H } | the $CH_2$'s of the cyclopentyl<br>axial $H_4$<br>axial $H_1$<br>CH of the cyclopentyl |
| 7.59(m) 3H<br>7.96(m) 1H } | aromatic H's |
| 8.12(s) 1H<br>8.04 | N=CH—N<br>assumed mobile H's |

EXAMPLE 9 trans(.+−.)-N2-(4-aminocyclohexyl)-9-(1-methylpropyl)-N6-(phenylmethyl)-9H-purine-2,6-diamine (2R, 3S)-2,3-dihydroxybutanedioate

Stage 1: (.+−.)-2,6-dichloro-9-(1-methylpropyl)-9H-purine

The operation is carried out as in Stage 1 of Example 3 and 1.32 mg of dichloro-2,6-purine, 2.75 g of triphenylphosphine (P(phenyl)3), 35 ml of tetrahydrofuran and 0.96 ml of 2-butanol are mixed together, the reaction medium is agitated at ambient temperature and 1.63 ml of DEAD (diethylazodicarboxylate) is added over approximately 20 minutes and agitation is carried out overnight at ambient temperature. The reaction medium is poured into 10 ml of a 1 M solution of $NaH_2PO_4$ followed by extracting 3 times with 10 ml of ethyl acetate, washing with 10 ml of water then with 5 ml of an aqueous solution of sodium chloride, drying and evaporating to dryness. After chromatography on silica eluting with methylene chloride/ethyl acetate in a proportion of 90/10 then another chromatography on silica eluting with cyclohexane/ethyl acetate/methylene chloride in a proportion of 70/15/15, 1.27 g of expected product is obtained in the form of white crystals.

Stage 2: (.+−.)-2-chloro-9-(1-methylpropyl)-N-(phenyl-methyl)-9H-purin-6-amine The operation is carried out as in Stage 2 of Example 3 and 161 mg of the product obtained in Stage 1 above, 3 ml of butanol and 0,132 ml of benzylamine are mixed together and the reaction medium is heated to a temperature of approximately 90 to 110° C. for approximately 5 hours, then left to return to ambient temperature. After leaving to crystallize, the reaction medium is diluted with 10 ml of isopropanol, followed by separating, washing with 10 ml of isopropanol and drying under vacuum at approximately 50° C. After chromatography on silica eluting with methylene chloride/ethyl acetate in a proportion of 50/50, In this way 179 mg of expected product is obtained in the form of white crystals.

Stage 3: trans(.+−.)-N2-(4-aminocyclohexyl)-9-(1-methylpropyl)-N6-(phenylmethyl)-9H-purine-2,6-diamine(2R,3S)-2,3-dihydroxybutanedioate The operation is carried out as in Stage 3 of Example 3 and 388 mg of trans-1,4-diaminocyclohexane is taken to a temperature of 150° C. and 107 mg of the product obtained in Stage 2 above is added and the reaction medium is left at a temperature of 140 to 150° C. for approximately 17 hours then left to return to ambient temperature. After then taking up in 10 ml of ethyl acetate/water in a proportion of 50/50, the reaction medium is left to settle, followed by re-extracting with 2×10 ml of ethyl acetate, washing with 10 ml of water and 5 ml of an aqueous solution of sodium chloride, drying and evaporating to dryness. After purification on silica eluting with methanol/ammonium hydroxide (NH4OH) in a proportion of 98/2, 10 ml of a 1M solution of m tartaric acid in ethanol is added followed by leaving to crystallize, separating, washing with 2×1 ml of ethanol and drying at a temperature of approximately 50° C. In this way 78 mg of expected product is obtained in the form of beige crystals.

| NMR in DMSO | |
|---|---|
| 0.73(t) 3H | $CH_3$—$CH_2$—CH—$CH_3$ |
| 1.69 to 1.99(m) | $CH_3$—$CH_2$—CH—$CH_3$ |
| 1.44(d) | $CH_3$—$CH_2$—CH—$CH_3$ |
| 4.27(m) 1H | $CH_3$—$CH_2$—CH—CH |
| 1.11 to 1.41(m) | the axial H of the cyclohexyl |
| 1.91(d) | the equatorial H of the cyclohexyl |
| 2.95(t) | axial $H_4$ |
| 3.58(m) | axial $H_1$ |
| 4.59(bs) 2H | phenyl-$CH_2$—NH |
| 6.17(d) <1H | NH—CH |
| 7.19(m) 1H<br>7.28(m) 2H<br>7.34(m) 2H } | aromatic H's |
| 7.77–7.74 | N=CH—N |
| 9.24<br>7.81 } | assumed mobile H's |

EXAMPLE 10 trans-N-(2-((2-((4-amino-cyclohexyl) amino)-9-cyclopentyl-9H-purin-6-yl)-amino)-ethyl)-4-methyl-benzenesulphonamide dihydrochloride

Stage 1: N-[2-[(2-chloro-9-cyclopentyl-9H-purin-6-yl)-amino]-ethyl]-4-methyl-benzenesulphonamide 280 mg of the product obtained in Stage 1 of Example 7, 3 ml of methylene chloride, 0.17 ml of $NEt_3$ (triethylamine) and 230 mg of 4-methyl-benzenesulphonic acid chloride are mixed together then the reaction medium is agitated at ambient temperature for approximately 30 minutes. Then 2 ml of water is added, followed by extracting with 2×5 ml of methylene chloride, washing with 5 ml of water, drying, evaporating, impasting in ether, separating and drying. In this way 345 mg of expected product is obtained.

Stage 2: trans-N-(2-((2-((4-amino-cyclohexyl)-amino)-9-cyclopentyl-9H-purin-6-yl)-amino)-ethyl)-4-methyl-benzenesulphonamide dihydrochloride 320 mg of the product obtained in Stage 1 above and 844 mg of trans-1,4-diaminocyclohexane are mixed together and the reaction medium is heated to approximately 140° C. for approximately 3 hours then lowered to 80° C., 5 ml AcOEt, then 10 ml of water are added warm. The reaction medium is left to return to ambient temperature, followed by extracting with 2×10 ml of ethyl acetate, washing with 10 ml of a saturated solution of sodium chloride then drying. After purification by chromatography on silica eluting with methylene chloride/methanol/ammonium hydroxide in a proportion of 90/10/1, 1.5 ml of hydrochloric acid/ethanol 1.4N, is added followed by leaving to crystallize, filtering, rinsing with 5 ml of ether and drying under vacuum. In this way 173 mg of expected product is obtained in the form of white crystals.

| NMR in DMSO | |
|---|---|
| 1.39(m) 2H } | the axial H of the cyclohexyl |
| 1.53(m) 2H | |
| 1.71(m) 2H } | |
| 1.90(m) 2H | |
| 2.07(masked) | the CH2's of the cyclopentyl |
| 2.18(m) 2H | |
| 2.34(s) 3H | phenyl-C$\underline{H_3}$ |
| 3.10(m) 3H | 1(CH$_2$)$_2$—NH + assumed axial H$_4$ |
| 3.71(m) 3H | 1(CH$_2$)$_2$—NH + assumed axial H$_1$ |
| 4.76(m) 1H | CH of the cyclopentyl |
| 7.29 2H } | -phenyl-SO$_2$ |
| 7.652H AA' BB' | |
| 8.10(bs) <3H | NH$_2$ + N=CH—N |
| 7.54 | |
| 8.26 | |
| 8.81 | assumed mobile H's |

EXAMPLE 11

Dihydrochloride of trans(.+−.)[[2-[(4-amino-cyclohexyl)-amino]-9-(tetrahydro-3-furanyl)-9H-purin-6-yl]-amino]-benzoate of ethyl Stage 1: ethyl (.+−.)-4-[[2-chloro-9-(tetrahydro-3-furanyl)-9H-purin-6-yl]-amino]-benzoate The operation is carried out as in Stage 2 of Example 2 starting from 181 mg of the product obtained in Stage 1 of Example 2 and 3 ml of butanol and using 124 ml of ethyl 4-amino-benzoate in place of the benzylamine. In this way 214 mg of expected product is obtained in the form of white crystals.

| NMR in DMSO | |
|---|---|
| 2.31(m) | |
| 2.55(m) 2H | CH—C$\underline{H_2}$—CH$_2$ |
| 3.91(m) 2H | O—C$\underline{H_2}$—CH |

| NMR in DMSO | |
|---|---|
| 5.22(m) 2H | O—CH$_2$—C$\underline{H}$ |
| 3.86(m) 1H } | O—C$\underline{H_2}$—CH$_2$ |
| 4.14(m) 1H | |
| 1.33(t) | CO$_2$—CH$_3$—CH$_2$ |
| 4.30(q) | |
| 7.95 to 8.03 AA'BB' | N-phenyl-C= |
| 8.41(s) 1H | N=C$\underline{H}$—N |
| 10.71(s) | =C—N$\underline{H}$ |

Stage 2: Dihydrochloride of ethyl trans(.+−.) [[2-[(4-aminocyclo-hexyl)-amino]-9-(tetrahydro-3-furanyl)-9H-purin-6-y]-amino]-benzoate The operation is carried out as in Stage 3 of Example 2 starting from 200 mg of the product obtained in Stage 1 above and 600 mg of trans-1,4-diaminocyclohexane. After purification on silica eluting with methanol/triethylamine (TEA) in a proportion of 95/5, salification is carried out with 1 to 2 ml of 1.4 N hydrochloric acid in ethanol, followed by diluting with 3 ml of ethyl acetate, leaving for two hours at ambient temperature, separating, washing with 5 ml of ethyl acetate and drying at a temperature of approximately 50° C. In this way 110 mg of expected product is obtained in the form of pink beige crystals.

| NMR in DMSO | |
|---|---|
| 1.32(t) | CO$_2$—CH$_2$—C$\underline{H_3}$ |
| 4.30(q) | CO$_2$—C$\underline{H_2}$—CH$_3$ |
| 1.30 to 1.60 | the axial H's of the cyclohexyl |
| 2.07 | the equatorial H's of the cyclohexyl |
| 2.36(m) } | CH$_2$ in position 4 |
| 2.50(m) | |
| 3.02 | CH$_2$—N + |
| 3.69 | CH—NC= |
| 3.86(m) } | CH$_2$ in position 5 |
| 4.13(m) | |
| 3.97(m) } | CH$_2$ in position 2 |
| 4.05(m) | |
| 5.17(bs) | H$_3$ |
| 7.96 to 8.17 | -phenyl-O- |
| 8.17 | weak absorption mobile NH3 + |
| 9.11(s) to 11.07(s) | NH |
| 7.56 | other mobile H's |

EXAMPLE 12 trans-N2-(4-aminocyclohexyl)-N6-(2-aminoethyl)-9-cyclopentyl-9H-purine-2,6-diamine trihydrochloride 160 mg of the product obtained in Stage 1 of Example 7, 10 ml of butanol and 690 mg of trans-1,4-diaminocyclohexane are mixed together, the reaction medium is heated to approximately 150° C. for approximately 4 days. After chromatography on silica eluting with methylene chloride/methanol/ammonium hydroxide in a proportion of 70/25/05 salification is carried out with a 1.4N solution of HCl in ethanol and in this way 60 mg of expected product is obtained.

| NMR in DMSO | |
|---|---|
| 1.25 to 1.55 | the axial H's of the cyclohexyl |
| 1.60 to 2.23 | the equatorial H's of the cyclohexyl and the CH2's of the cyclopentyl |
| 3.11 | C$\underline{H}$—→N |
| 3.77 | =C—NH—C$\underline{H}$— |
| 3.05 | |
| 3.68(b) | =C—N—C$\underline{H}_2$ |
| 4.77(bs) | N=C—N—CH |
| 8.16(bs) | mobile H's |

EXAMPLE 13 trans-(.+−.)-N2-(4-aminocyclohexyl)-N6-[(3-iodophenyl)-methyl]-9-(tetrahydro-3-furanyl)-9H-purine-2,6-diamine (2R,3S)-2,3-dihydroxybutanedioate Stage 1: (.+−.)-2-chloro-N-[(3-iodophenyl)-methyl]-9-(tetrahydro-3-furanyl)-9H-purin-6-amine The operation is carried out as in Stage 2 of Example 2 starting from 133 mg of the product obtained in Stage 1 of Example 2 and 2 ml of butanol and using 0.2 mg of 3-iodo-benzenemethanamine (1.1 eq) in place of the benzylamine. In this way 208 mg of expected product is obtained in the form of white crystals.

| NMR in CDCl$_3$ | |
|---|---|
| 2.16(m) | |
| 2.61(m) | CH$_2$ in position 4 |
| 3.97(m) | |
| 4.19(m) | CH$_2$ in position 5 |
| 3.98(m) | |
| 4.09(bd) | CH$_2$ in position 2 |
| 5.31(m) | H$_3$ |
| 6.57(bs) | NH |
| 7.07(t) | H$_5$' |
| 7.34(d) | |
| 7.62(d) | H$_4$' and H$_6$' |
| 7.73(bs) | H$_2$' |
| 7.90(s) | CH=N |

Stage 2: trans(.+−.)-N2-(4-aminocyclohexyl)-N6-[(3-iodophenyl)-methyl]-9-(tetrahydro-3-furanyl)-9H-purine-2,6-diamine (2R,3S)-2,3-dihydroxybutanedioate The operation is carried out as in Stage 3 of Example 2 starting from 187 mg of the product obtained in Stage 1 above and 470 mg of trans-1,4-diaminocyclohexane. After purification on silica eluting with methanol/Ammonium hydroxide (NH$_4$OH) in a proportion of 98/2 and salification with a 1 M solution of m. tartaric acid in ethanol, the reaction medium is left overnight at ambient temperature, followed by separating, washing with 10 ml of ethyl acetate and drying at a temperature of approximately 50° C. In this way 137 mg of expected product is obtained in the form of beige crystals.

| NNR in DMSO | |
|---|---|
| 1.29(m) | the axial CH$_2$'s of the cyclohexyl |
| 1.93(d) | the equatorial CH$_2$'s of the cyclohexyl |
| 2.27(m) | |
| 2.40(m) | 2H O—CH$_2$—CH$_2$ |
| 2.95(bt) 1H | axial H$_4$ |
| 3.60(m) 1H | axial H$_1$ |
| 3.77 to 4.00 4H | in excess |
| 4.08 1H | the CH$_2$—O's |
| 4.56(bs) 2H | phenyl-C$\underline{H}_2$—NH |
| 4.94(m) 1H | —N—C$\underline{H}$—CH$_2$—O |
| 6.31(d) <1H | N$\underline{H}$—CH |
| 7.11(t) 1H | H$_5$' |
| 7.35(d) 1H | |
| 7.57(d) 1H | H$_4$', H$_6$' |
| 7.71(s) 1H | H$_2$' |
| 7.73(s) 1H | N=C$\underline{H}$—N |
| 7.99 | assumed mobile H |

EXAMPLE 14

Sodium salt of trans-4((2-(4-amino-cyclohexyl)-amino)-9-cyclopentyl-9H-purin-6-yl)amino)-benzoic acid 240 mg of the product of Example 6, 10 ml of ethanol then 1 ml of sodium (.+−.)-2-chloro-N-propyl-9-(tetrahydro-3-furanyl)-9H-purin-6-amine are introduced at ambient temperature, the reaction medium is agitated at ambient temperature for approximately 20 hours, heated to approximately 95° C. for approximately 3 hours then left overnight at ambient temperature, followed by evaporating to dryness, impasting in acetic acid then in ether, drying at approximately 50° C. and in this way 244 mg of expected product is obtained in the form of beige crystals.

| NMR in DMSO | |
|---|---|
| 1.17(m) 2H | |
| 1.26(m) 2H | the axial H's of the cyclohexyl |
| 1.67(m) | |
| 1.83(m) | |
| 1.98(m) 12H | the equatorial H's of the cyclohexyl + |
| 2.08(m) | the CH$_2$'s of the cyclopentyl |
| 2.53(masked) | axial H$_4$ |
| 3.65(ml) 1H | axial H$_1$ |
| 4.68(m) 1H | CH of the cyclopentyl |
| 6.43(d) <1H | —HN—C$\underline{H}$— |
| 7.76 2H | |
| 7.91 2H | AA' BB' NH-phenyl-CHO |
| 7.88(s) 1H | —N=C$\underline{H}$—N— |
| 9.28 | assumed mobile H |

EXAMPLE 15 trans (.+−.)-N2-(4-aminocyclo-hexyl)-N6-propyl-9-(tetrahydro-3-furanyl)-9H-purine-2,6-diamine dihydrochloride

Stage 1: (.+−.)-2-chloro-N-propyl-9-(tetrahydro-3-furanyl)-9H-purin-6-amine The operation is carried out as in Stage 2 of Example 2 starting from 181 mg of the product obtained in Stage 1 of Example 2 and 3 ml of butanol and using 0.062 ml of 1-propanamine in place of the benzylamine. In this way 136 mg of expected product is obtained in the form of beige crystals.

| NMR in DMSO | |
|---|---|
| 1.02(t) | C$\underline{H_3}$—CH$_2$—CH$_2$—NH$_2$ |
| 1.71(m) | CH$_3$—C$\underline{H_2}$—CH$_2$—NH$_2$ |
| 3.59(m) | CH$_3$—CH$_2$—C$\underline{H_2}$—NH$_2$ |
| 2.17 (m) | } CH$_2$ in position 4 |
| 2.61(m) | |
| 3.99(m) | } CH$_2$ in position 2 |
| 4.09(bd) | |
| 3.99(m) | } CH$_2$ in position 5 |
| 4.19(m) | |
| 6.04 and 5.80 | resolved NH |
| 7.89(s) | CH=N |

Stage 2: trans(.+−.)-N2-(4-aminocyclo-hexyl)-N6-propyl-9-(tetrahydro-3-furanyl)-9H-purine-2,6-diamine dihydrochloride The operation is carried out as in Stage 3 of Example 2 starting from 109 mg of the product obtained in Stage 1 above and 445 mg of trans-1,4-diaminocyclohexane. After purification on silica eluting with methanol/ammonium hydroxide (NH$_4$OH) in a proportion of 98/2, salification is carried out with 1.4 N hydrochloric acid in ethanol. In this way 78 mg of expected product is obtained in the form of crystals.

| NMR in DMSO | |
|---|---|
| 0.94(t) 3H | C$\underline{H_3}$—CH$_2$—CH$_2$—NH— |
| 1.65(m) 2H | CH$_3$—C$\underline{H_2}$—CH$_2$—NH |
| 3.58(bs, masked) | CH$_3$—CH$_2$—C$\underline{H_2}$—NH |
| 1.37 to 1.52 | the axial H's of the cyclohexyl |
| 2.08 | the equatorial H's of the cyclohexyl |
| 3.05(bn) 1H | axial H$_4$ |
| 3.72(bt) 1H | axial H$_1$ |
| 8.12(bs) | N=CHN = mobile H's (NH$_2$) |
| 9.32(bs) <1H | mobile H |

EXAMPLE 16 trans-N-[2-[(4-aminocyclo-hexyl)-amino]-9-cyclopentyl-9H-purin-6-yl]-4-(1-methylethyl)-benzenesulphonamide dihydrochloride

Stage 1: N-[[2-chloro-9-cyclopentyl-9H-purin-6-yl]amino]-4-(1-methylethyl)-benzenesulphonamide The operation is carried out as in Stage 1 of Example 8 and 257 mg of the product obtained in Stage 1 of Example 1, 4 ml of dimethoxyethane (DME), 390 mg of carbonate of caesium (CS$_2$CO$_3$) and 199 mg of 4-(1-methylethyl)-benzenesulphonamide in place of the benzenesulphonamide are mixed together and the reaction medium is agitated at a temperature of approximately 100° C. for approximately 2 hours 30 minutes, left to return to ambient temperature and acidified with 4 ml of 2N hydrochloric acid, followed by extracting with 2×10 ml of ethyl acetate, drying and evaporating to dryness. Crystallization is carried out from 5 ml of ether, followed by separating and drying at ambient temperature. In this way 187 mg of expected product is obtained in the form of colourless crystals.

Stage 2: trans-N-[2-[(4-aminocyclo-hexyl)amino]-9-cyclopentyl-9H-purin-6-yl]-4-(1-methylethyl)-benzenesulphonamide dihydrochloride The operation is carried out as in Stage 2 of Example 8 and 456 mg of trans-1,4-diaminocyclohexane is taken to a temperature of approximately 150° C., 168 mg of the product obtained in Stage 1 above is added and the reaction medium is maintained at this temperature of 150° C. for approximately 3 hours 30 minutes then left to return to ambient temperature. 10 ml of water is added, followed by separating, washing with 5 ml of water and drying under vacuum at a temperature of approximately 50° C. Acidification is carried out to pH=4–5, followed by extracting with 10 ml of ethyl acetate then the product in the aqueous phase is evaporated to dryness. After dissolving in 5 ml of ethanol, 5 ml of ethanol/1.4N hydrochloric acid is added, followed by evaporating to dryness, impasting in 5 ml of ether and in this way 42 mg of expected product is obtained in the form of crystals.

| NNR in DMSO | |
|---|---|
| 1.22(d) 6H | C$\underline{H_3}$—CH |
| 2.98(m) 1H | CH$_3$—C$\underline{H}$ |
| 1.33(m) 2H | } the axial H's of the cyclohexyl |
| 1.53(m) 2H | |
| 1.68(m) 2H | |
| 1.88(m) 2H | the CH$_2$'s of the cyclopentyl + |
| 2.06(m) 8H | the equatorial CH$_2$'s of the cyclohexyl |
| 3.00(masked) | axial H$_4$ |
| 3.57(m) | axial H$_1$ |
| 4.71(m) 1H | CH of the cyclopentyl |

-continued

| NNR in DMSO | | |
|---|---|---|
| 7.43 2H | } | AA'BB' iPr-phenyl-SO$_2$— |
| 7.88 2H | | |
| 8.11(s) 1H | | N=C$\underline{H}$—N |
| 5.10 | } | assumed mobile H's |
| 8.22 | | |

EXAMPLE 17 trans-N2-(4-aminocyclo-hexyl)-9-cyclopentyl-N6-[2-[[(4-methoxyphenyl)-methyl]-amino]-ethyl]-9H-purine-2,6-diamine trihydrochloride Stage 1: 2-chloro-9-cyclopentyl-N-[2-[[(4-methoxyphenyl)-methyl]-amino]-ethyl]-9H-purin-6-amine The operation is carried out as in Stage 2 of Example 7 starting from 280 mg of the product obtained in Stage 1 of Example 7, 4 ml of methanol, 0.2 ml of 4-methoxybenzaldehyde, 0.2 ml of acetic acid and 100 mg of NaBH$_3$CN and the reaction medium is agitated at ambient temperature for approximately 6 hours. 10 ml AcOEt is added, followed by washing with 2×5 ml H$_2$O, then 5 ml of a saturated aqueous solution of NaCl, followed by drying and evaporating the solvent. After chromatography on silica eluting with CH$_2$Cl$_2$/methanol/ammonium hydroxide in a proportion of 90/10/1, 208 mg of expected product is thus obtained.

Stage 2: trans-N2-(4-aminocyclohexyl)-9-cyclopentyl-N6-[2-[[(4-methoxyphenyl)-methyl]-amino]-ethyl]-9H-purine-2,6-diamine trihydrochloride The operation is carried out as in Stage 3 of Example 7 starting from 186 mg of the product obtained in Stage 1 above, 490 mg of trans-1,4-diaminocyclohexane, the reaction medium is heated to approximately 140° C. for 10 hours. Purification is carried out on silica eluting with CH$_2$Cl$_2$/MeOH/NH$_4$OH (85/15/1.5) then salification with a 1.4N solution of hydrochloric acid to in ethanol. In this way 60 mg of expected product is obtained.

| NMR in DMSO | | |
|---|---|---|
| 1.38(m) 2H | } | the axial H's of the cyclohexyl |
| 1.55(m) 2H | | |
| 1.71(m) | } | the CH$_2$'s of the cyclopentyl |
| 1.90(m) | | |
| 2.05(masked) | | |
| 2.17(m) | | |
| 2.06(m) | | the equatorial H's of the cyclohexyl |
| 3.04(m, b) | | axial H$_4$ |
| 3.23(bs) 2H | } | NH—C$\underline{H}_2$—C$\underline{H}_2$—NH |
| 3.99(bs) 2H | | |
| 3.71(m) | | axial H$_1$ |
| 3.78(s) | | O—C$\underline{H}_3$ |
| 4.15(s) 2H | | NH—C$\underline{H}_2$-phenyl |
| 4.77(m) | | CH of the cyclopentyl |
| 6.96 2H | } | O-phenyl- |

| NMR in DMSO | | |
|---|---|---|
| 7.51 2H AA'BB' | | |
| 8.24(s) 1H | | N=CH—N— |
| 8.12 | } | assumed mobile H's |
| 8.70 | | |
| 9.42 | | |

EXAMPLE 18 trans-N2-(4-aminocyclohexyl)-9-cyclopentyl-N6-[2-[[(7-methoxy-1,3-benzodioxol-5-yl)-methyl]-amino]-ethyl]-9H-purine-2,6-diamine trihydrochloride Stage 1: 2-chloro-9-cyclopentyl-N-[2-[[(7-methoxy-1,3-benzodioxol-5-yl)-methyl]-amino]-ethyl]-9H-purin-6-amine The operation is carried out as in Stage 2 of Example 7 starting from 280 mg of the product obtained in Stage 1 of Example 7, 4 ml of methanol, 250 mg of 7-methoxy-1,3-benzodioxole-5-carboxaldehyde in place of the benzaldehyde, 0.2 ml of acetic acid and 0.4 ml of tetrahydrofuran and the reaction medium is left for 4 hours at ambient temperature. Then 100 mg of NaBH3CN is added and agitation is carried out at ambient temperature for approximately 3 hours. 10 ml AcOEt is added, followed by washing with 2×5 ml H$_2$O, then 5 ml of saturated aqueous solution of NaCl, followed by drying and evaporating the solvent and purification by chromatography on silica eluting with methylene chloride/methanol/ammonium hydroxide in a proportion of 90/10/1. In this way 311 mg of expected product is obtained in the form of beige crystals.

Stage 2: trans-N2-(4-aminocyclohexyl)-9-cyclopentyl-N6-[2-[[(7-methoxy-1,3-benzodioxol-5-yl)-methyl]-amino]-ethyl]-9H-purine-2,6-diamine trihydrochloride The operation is carried out as in Stage 3 of Example 7 starting from 65 mg of the product obtained in Stage 1 above, 743 mg of trans-1,4-diaminocyclohexane, the reaction medium is heated to approximately 140° C. for 3 hours, followed by treating with 10 ml of water, extracting with 2×10 ml of ethyl acetate, washing with 10 ml of NaCl (saturated aqueous solution) and drying over MgSO$_4$. Salification is carried out with 1.4N HCL/EtOH, followed by filtering, washing with 5 ml EtOH then drying at ~50° C. In this way 161 mg of expected product is obtained.

| NMR in DMSO | | |
|---|---|---|
| 1.35(m) 2H | } | the axial H's of the cyclohexyl |
| 1.53(m) 2H | | |
| 1.70(m) 2H | } | the CH$_2$'s of the cyclopentyl |
| 1.89(m) 2H | | |
| 2.06(masked) | | |
| 2.15(m) 2H | | |
| 3.03(m, b) 1H | | axial H$_4$ |

-continued

NMR in DMSO

| | | |
|---|---|---|
| 3.21(bs) 2H | } | NH—CH$_2$—CH$_2$—NH |
| 3.96(bs) | | |
| 3.70(bt) | axial H$_1$ | |
| 3.83(s) | O—CH$_3$ | |
| 4.12(s) 2H | NH—CH$_2$-phenyl | |
| 4.76(m) 1H | CH of the cyclopentyl | |
| 6.01(s) 2H | O—CH$_2$—O | |
| 6.84(d) | } | H$_4$, H$_6$ |
| 6.96(d) | | |
| 8.24(s) 1H | N=CH—N | |
| 9.42 | } | assumed mobile H's |
| 8.63 | | |
| 8.08 | | |

EXAMPLE 19 trans-N2-(4-aminocyclohexyl)-N6-[2-[[[4-chloro-3-trifluoromethyl)-phenyl]-methyl]-amino]-ethyl]-9-cyclopentyl-9H-purine-2,6-diamine trihydrochloride Stage 1: 2-chloro-N-[2-[[[4-chloro-3-(trifluoromethyl)-phenyl]-methyl]-amino]-ethyl]-9-cyclopentyl-9H-purin-6-amine The operation is carried out as in Stage 2 of Example 7 starting from 280 mg of the product obtained in Stage 1 of Example 7, 4 ml of methanol, 292 mg of 4-chloro-3-(trifluoromethyl)-benzaldehyde in place of the benzaldehyde and 0.2 ml of acetic acid, then the reaction medium is agitated at ambient temperature for approximately 3 hours.

100 mg of NaBH$_3$CN is added and the reaction medium is agitated at ambient temperature for approximately 3 hours. 10 ml AcOEt is added, followed by washing with 2×5 ml H$_2$O, then with 5 ml of a saturated aqueous solution of NaCl, followed by drying and evaporating the solvent. After purification by chromatography on silica eluting with methylene chloride/methanol/ammonium hydroxide in a proportion of 90/10/1, 367 mg of expected product is obtained in the form of beige crystals.

Stage 2: trans-N2-(4-aminocyclohexyl)-N6-[2-[[[4-chloro-3-(trifluoromethyl)-phenyl]-methyl]-amino]-ethyl]-9-cyclopentyl-9H-purine-2,6-diamine trihydrochloride.

The operation is carried out as in Stage 3 of Example 7 starting from 320 mg of the product obtained in Stage 1 above and 770 mg of trans-1,4-diaminocyclohexane and the reaction medium is heated to approximately 140° C. for 3 hours. After purification by chromatography on silica eluting with methylene chloride/methanol/ammonium hydroxide in a proportion of 85/25/1.5 salification is carried out with 1.4N HCl/EtOH, followed by filtering, washing with 5 ml EtOH then drying at ~50° C. In this way 166 mg of expected product is obtained.

NMR in DMSO

| | | |
|---|---|---|
| 1.35(m) 2H | } | the axial H's of the cyclohexyl |
| 1.54(m) 2H | | |
| 1.70(m) 2H | } | the CH$_2$'s of the cyclopentyl |
| 1.90(m) 2H | | |
| 2.03(masked) | | |
| 2.16(m) 2H | | |
| 2.03(m) | the equatorial H's of the cyclohexyl | |
| 3.03(m, b) 1H | axial H$_4$ | |
| 3.72(bt) | axial H$_1$ | |
| 9.28(bs) 2H | | |
| 4.00(bs) | NH—CH$_2$—CH$_2$—NH | |
| 4.34(bs) 2H | NH—CH$_2$—phenyl | |
| 4.78(m) 1H | CH of the cyclopentyl | |
| 7.94(dd) 1H | H$_5$' | |
| 7.77(d) 1H | H$_6$' | |
| 8.15(d) 1H | H$_3$' | |
| 8.33(s) 1H | N=CH—N | |
| 8.11 | } | assumed mobile H's |
| 8.84 | | |
| 9.73 | | |

EXAMPLE 20 trans-N2-(4-aminocyclohexyl)-9-cyclopentyl-N6-[(diphenylmethyl)-amino]-ethyl]-9H-purine-2,6-diamine trihydrochloride Stage 1: 2-chloro-9-cyclopentyl-N-[2-[(diphenylmethyl)-amino]-ethyl]-9H-purin-6-amine The operation is carried out as in Stage 2 of Example 7 starting from 141 mg of the product obtained in Stage 1 of Example 7, 2 ml of methanol, 0.7 ml (15 eq) of benzaldehyde and 0.1 ml of acetic acid then the reaction medium is agitated at ambient temperature for approximately 3 hours. Then 55 mg of sodium cyanoborohydride (NaBH$_3$CN) is added and the reaction medium is agitated at ambient temperature for 1 hour. 10 ml AcOEt is added, followed by washing with 2×5 ml H$_2$O, then 5 ml of a saturated aqueous solution of NaCl, drying and evaporating the solvent. After purification by chromatography on silica eluting with methylene chloride/ethyl acetate in a proportion of 70/30, the product obtained is impasted in hexane and in this way 143 mg of expected product is obtained.

Stage 2: trans-N2-(4-aminocyclohexyl)-9-cyclopentyl-N6-[(diphenylmethyl)-amino]-ethyl]-9H-purine-2,6-diamine trihydrochloride The operation is carried out as in Stage 3 of Example 7 starting from 90 mg of the product obtained in Stage 1 above and 222 mg of trans-1,4-diaminocyclohexane and the reaction medium is heated to approximately 140° C. for approximately 2 hours. After purification by chromatography on silica eluting with methylene chloride/methanol/ammonium hydroxide in a proportion of 85/15/1.5 salification is carried out with 1.4N HCl/EtOH, followed by filtering, washing with 5 ml of EtOH then drying at ~50° C.

| NNR in DMSO | |
|---|---|
| 1.37(m) 2H<br>1.53(m) 2H | } the axial H's of the cyclohexyl |
| 1.72(m)<br>1.90(m)<br>2.04(m)<br>2.18(m) | the equatorial H's of the cyclohexyl and the CH$_2$'s of the cyclopentyl |
| 3.04(bs) 1H | axial H$_4$ |
| 3.24(bs) 2H<br>3.97(bt) | } NH—C$\underline{H}_2$—C$\underline{H}_2$—NH |
| 3.68(bt) 1H | H$_1$ axial |
| 4.29(bs) 2H | NH—C$\underline{H}_2$-phenyl |
| 4.75(m) 1H | =C—N—CH |
| 7.34(m)<br>7.61(bs) 10H | } the aromatics |
| 8.19 | N=CH—N |
| 8.08<br>8.68 | } assumed mobile H's |

EXAMPLE 21 dihydrochloride of trans-4-[[[2-[(4-aminocyclohexyl)-amino]-9-cyclopentyl-9H-purin-6-yl]-amino]-methyl]-benzoic acid The operation is carried out as in Stage 3 of Example 1 starting from 741 mg of trans-1,4-diaminocyclohexane which is heated to approximately 140° C. then 500 mg of the product obtained in Stage 2 of Example 1 is added and the reaction medium is left at this temperature for approximately 3 hours then left to return to ambient temperature. 5 ml H$_2$O is added, followed by filtering. The precipitate is taken up in 10 ml of ethanol then 3 ml of 1.4N hydrochloric acid in ethanol is added, followed by filtering the insoluble part and evaporating to dryness. The residue is impasted in ether, followed by drying at ambient temperature and in this way 45 mg of expected product is obtained.

| NMR in DMSO | |
|---|---|
| 1.34(m) 2H<br>1.48(m) 2H | } the axial H's of the cyclohexyl |
| 1.70 2H<br>1.89 2H<br>2.01 masked<br>2.17 2H | } the CH2's of the cyclopentyl |
| 2.01(m) | the equatorial H's of the cyclohexyl |
| 3.01(bs) 1H | axial H$_4$ |
| 3.68(bt) 1H | axial H$_1$ |
| 4.76(m) 1H | CH of the cyclopentyl |
| 4.91(bs) 2H | HN—C$\underline{H}_2$-phenyl |
| 7.50 2H<br>7.91 2H | } AA' BB' phenyl-CHO |
| 8.01<br>9.26 | } assumed mobile H's |

EXAMPLE 22

Trihydrochloride of methyl trans 4-[[[2-[[2-[(4-amino-cyclohexyl)-amino]-9-cyclopentyl-9H-purin-6-yl]-amino]-ethyl]-amino]-methyl]-benzoate Stage 1: methyl 4-[[[2-[(2-chloro-9-cyclopentyl-9H-purin-6-yl)-amino]-ethyl]-amino]-methyl]-benzoate The operation is carried out as in Stage 2 of Example 7 starting from 280 mg of the product obtained in Stage 1 of Example 7, 4 ml of methanol, 230 mg of methyl 4-formyl-benzoate in place of the benzaldehyde and 0.2 ml of acetic acid then the reaction medium is agitated at ambient temperature for 5 hours. Then 100 mg of NaBH3CN is added and the reaction medium is agitated at ambient temperature for approximately 1 hour. 10 ml AcOEt is added, followed by washing with 2×5 ml H$_2$O, then 5 ml of a saturated aqueous solution of NaCl, drying and evaporating the solvent. After purification by chromatography on silica eluting with methylene chloride/methanol/ammonium hydroxide in a proportion of 95/05/0.5, 260 mg of expected product is obtained.

Stage 2: Trihydrochloride of methyl trans 4-[[[2-[[2-[(4-amino-cyclohexyl)-amino]-9-cyclopentyl-9H-purin-6-yl]-amino]-ethyl]-amino]-methyl]-benzoate The operation is carried out as in Stage 3 of Example 7 starting from 256 mg of the product obtained in Stage 1 above and 700 mg of trans-1,4-diaminocyclohexane and the reaction medium is heated to approximately 140° C. for approximately 4 hours, followed by extracting with 3×10 ml of ethyl acetate and washing with 10 ml of a saturated aqueous solution of sodium chloride. After purification by chromatography on silica eluting with methylene chloride/methanol/ammonium hydroxide in a proportion of 85/15/1.5, salification is carried out with 1.4N HCl/EtOH, followed by filtering, washing with 5 ml EtOH then drying at 50° C. In this way 70 mg of expected product is obtained.

| NMR in DMSO | |
|---|---|
| 1.38(m) 2H<br>1.52(m) 2H | } the axial H's of the cyclohexyl |
| 1,70–1.89<br>2.06(masked)–2.17 | } the CH$_2$'s of the cyclopentyl |
| 2.04(m) | the equatorial H's of the cyclohexyl |
| 3.04(bs) 1H | axial H$_4$ |
| 3.28(bs) 2H<br>4.00(bs) | } NH—C$\underline{H}_2$—C$\underline{H}_2$—NH |
| 3.72(bt) 1H | axial H$_1$ |
| 4.32(bs) 2H | NH—C$\underline{H}_2$-phenyl |
| 4.77 | CH of the cyclopentyl |
| 3.88(s) | CO$_2$—CH$_3$ |
| 7.74 2H<br>7.98 2H AA'BB' | phenyl-CO$_2$CH$_3$ |
| 7.69 2H<br>7.89 2H AA'BB' | phenyl-CO$_2$H |
| 8.33 | N=CH—N |
| 8.13 | |
| 8.90 | |

| NMR in DMSO | |
|---|---|
| 9.48 | } assumed mobile H's |
| 9.68 | |

EXAMPLE 23 trans-N2-(4-aminocyclo-hexyl)-N6-[4-cyanophenyl)-methyl]-amino]-ethyl]-9-cyclo-pentyl-9H-purine-2,6-diamine trihydrochloride Stage 1: 2-chloro-N-[2-[[(4-cyanophenyl)-methyl]-amino]-ethyl]-9-cyclopentyl-9H-purin-6-amine The operation is carried out as in Stage 2 of Example 7 starting from 280 mg of the product obtained in Stage 1 of Example 7, 184 mg of 4-cyano-benzaldehyde in place of the benzaldehyde, 4 ml of methanol and 0.2 ml of acetic acid and 0.5 ml of tetrahydrofuran then the reaction medium is agitated at ambient temperature for approximately 5 hours. then 100 mg of $NaBH_3CN$ is added and agitation is carried out at ambient temperature for 1 hour. 10 ml AcOET is added, followed by washing with 2×5 ml $H_2O$, then 5 ml of a saturated aqueous solution of NaCl, drying and evaporating the solvent. After purification by chromatography on silica eluting with methylene chloride/methanol/hydroxylamine in a proportion of 95/05/0.33, 347 mg of expected product is obtained in the form of white crystals.

Stage 2: trans-N2-(4-aminocyclohexyl)-N6-[4-cyanophenyl)-methyl]-amino]-ethyl]-9-cyclopentyl-9H-purin-2,6-diamine trihydrochloride The operation is carried out as in Stage 3 of Example 7 starting from 250 mg of the product obtained in Stage 1 above and 720 mg of trans-1,4-diaminocyclohexane and the reaction medium is heated to approximately 140° C. for 4 hours, followed by taking up in 10 ml $H_2O$, extracting with 3×10 ml of ethyl acetate and washing with 10 ml of saturated sodium chloride. After purification by chromatography on silica eluting with methylene chloride/methanol/hydroxylamine in a proportion of (85/15/1.5), salification is carried out with 1.4N HCl/EtOH, followed by filtering, washing with 5 ml EtOH then drying at ~50° C. In this way 222 mg of expected product is obtained.

| NMR in DMSO | |
|---|---|
| 1.36(m) 2H | } the axial H's of the cyclohexyl |
| 1.55(m) 2H | |
| 1.70(m) 2H | } the CH2's of the cyclopentyl |
| 1.89(m) 2H | |
| 2.05(masked) | |
| 2.17(m) 2H | |
| 2.04(m) | the equatorial H's of the cyclohexyl |
| 3.04(bs) 1H | axial $H_4$ |
| 3.73(bt) 1H | axial $H_1$ |
| 3.28(bs) 2H | } NH—$CH_2$—$CH_2$—NH |
| 4.02(bs) 2H | |

| NMR in DMSO | |
|---|---|
| 4.33(bs) 2H | NH—$CH_2$-phenyl |
| 4.78(m) 1H | CH of the cyclopentyl |
| 7.83 2H | } phenyl-CN |
| 7.88 2HAA'BB' | |
| 8.39(bs) 1H | N=CH—N |
| 8.19 | } assumed mobile H's |
| 9.02 | |

EXAMPLE 24 trans-N2-(4-aminocyclohexyl)-9-cyclopentyl-N6-[2-[[3,4-5-trimethoxyphenyl)-methyl]-amino]-ethyl]-9H-purin-2,6-diamine trihydrochloride Stage 1: 2-chloro-9-cyclopentyl-N-[2-[[(3,4,5-trimethoxy-phenyl)-methyl]-amino]-ethyl]-9H-purin-6-amine The operation is carried out as in Stage 2 of Example 7 starting from 280 mg of the product obtained in Stage 1 of Example 7, 275 mg of 3,4,5 trimethoxybenzaldehyde in place of the benzaldehyde, 4 ml of methanol and 0.2 ml of acetic acid then the reaction medium is agitated at ambient temperature for 5 hours. Then 100 mg of $NaBH_3CN$ is added and the reaction medium is agitated at ambient temperature for approximately 1 hour. 10 ml AcOEt is added, followed by washing with 2×5 ml $H_2O$, then 5 ml of a saturated aqueous solution of NaCl, drying and evaporating the solvent. After purification by chromatography on silica eluting with methylene chloride/methanol/ammonium hydroxide in a proportion of 95/05/0.33, 305 mg of expected product is obtained in the form of white crystals.

Stage 2: trans-N2-(4-aminocyclohexyl)-9-cyclopentyl-N6-[2-[[3,4-5-trimethoxyphenyl)-methyl]-amino]-ethyl]-9H-purin-2,6-diamine trihydrochloride The operation is carried out as in Stage 3 of Example 7 starting from 297 mg of the product obtained in Stage 1 above and 735 mg of trans-1,4-diaminocyclohexane and the reaction medium is heated to approximately 140° C. for 3 hours 30 minutes, followed by pouring into 10 ml of $H_2O$, extracting with 3×10 ml of ethyl acetate and washing with 10 ml of saturated sodium chloride. After purification by chromatography on silica eluting with methylene chloride/methanol/ammonium hydroxide in a proportion of 85/15/1.5, salification is carried out with 1.4N HCl/EtOH, followed by filtering, washing with 5 ml EtOH then drying at ~50° C.

| NMR in DMSO | |
|---|---|
| 1.38(m) 2H | } the axial H's of the cyclohexyl |
| 1.52(m) 2H | |
| 2.07(m) | the equatorial H's of the cyclohexyl |

-continued

| NMR in DMSO | |
|---|---|
| 3.04(ml) 1H | axial H₄ |
| 3.73(partially masked) | axial H₁ |
| 1.70 | |
| 1.98 | the C—CH₂C |
| 2.18 | |
| 4.78 | N—CH N-cyclopentyl |
| 3.24(ml) 2H | NH—CH₂—CH₂—NH |
| 4.02(bs) 2H | |
| 3.68(s) | O—CH₃ |
| 3.80(s) 3H | |
| 4.15 | N—CH₂—C=H₂ the CH's of the tetrasubstituted ring |
| 8.11(b)–8.35(b) 1H | N=CH—N |
| 5.48 | |
| 7.75 | |
| 8.11 | assumed mobile H's |
| 8.99 | |
| 9.57 | |

EXAMPLE 25 trans-N2-(4-aminocyclohexyl)-N6-[2-[[(4-chlorophenyl)-methyl]-amino]-ethyl]-9-cyclopentyl-9H-purin-2,6-diamine trihydrochloride Stage 1: 2-chloro-N-[2-[[(4-chlorophenyl)-methyl]-amino]-ethyl]-9-cyclopentyl-9H-purin-6-amine The operation is carried out as in Stage 2 of Example 7 starting from 280 mg of the product obtained in Stage 1 of Example 7, 197 mg of 4-chlorobenzaldehyde in place of the benzaldehyde, 4 ml of methanol and 0.2 ml of acetic acid then the reaction medium is agitated at ambient temperature for 5 hours. Then 100 mg of NaBH₃CN is added and the reaction medium is agitated at ambient temperature for approximately 1 hour. 10 ml AcOEt is added, followed by washing with 2×5 ml of H₂O, then 5 ml of a saturated aqueous solution of NaCl, drying and evaporating the solvent. After purification by chromatography on silica eluting with methylene chloride/methanol/ammonium hydroxide in a proportion of 95/05/0.33, 258 mg of expected product is obtained.

Stage 2: trans-N2-(4-aminocyclohexyl)-N6-[2-[[(4-chlorophenyl)-methyl]-amino]-ethyl]-9-cyclopentyl-9H-purin-2,6-diamine trihydrochloride The operation is carried out as in Stage 3 of Example 7 starting from 242 mg of the product obtained in Stage 1 above and 680 mg of trans-1,4-diaminocyclohexane and the reaction medium is heated to approximately 140° C. for approximately 3 hours 30 minutes, then poured into H₂O, followed by extracting with 3×10 ml of ethyl acetate and washing with 10 ml of saturated sodium chloride. After purification by chromatography on silica eluting with methylene chloride/methanol/ammonium hydroxide in a proportion of 85/15/1.5, salification is carried out with HCl/EtOH 1.4N followed by filtering, washing with 5 ml EtOH then drying at ~ 50° C.

| NNR in DMSO | |
|---|---|
| 1.37(m) 2H | the axial H's of the cyclohexyl |
| 1.54(m) 2H | |
| 1.70(m) 2H | |
| 1.89(m) 2H | |
| 2.05(masked) | the CH2's of the cyclopentyl |
| 2.17(m) 2H | |
| 2.05(m) | the equatorial H's of the cyclohexyl |
| 3.05(bs) 1H | axial H₄ |
| 3.25(bs) 2H | NH—CH₂—CH₂—NH |
| 3.99(bs) 2H | |
| 3.77(bt) 1H | axial H₁ |
| 4.12(bs) 2H | HN—CH₂-phenyl |
| 4.78(m) 1H | CH of the cyclopentyl |
| 7.47 2H | -phenyl-Cl |
| 7.63 2H AA'BB' | |
| 8.35(bs) 1H | N=CH—N |
| 8.13 | |
| 8.91 | assumed mobile H's |
| 9.61 | |

EXAMPLE 26 trans-N-[2-[(4-aminocyclo-hexyl)-amino]-9-cyclopentyl-9H-purin-6-yl]-3-bromo-benzene-sulphonamide dihydrochloride Stage 1: 3-bromo-N-[[2-chloro-9-cyclopentyl-9H-purin-6-yl]-amino]-benzenesulphonamide The operation is carried out as in Stage 1 of Example 8 starting from 257 mg of the product obtained in Stage 1 of Example 1, 4 ml of dimethoxyethane (DME), 390 mg of caesium carbonate (Cs₂CO₃) and 236 mg of 3-bromo-benzenesulphonamide in place of the benzenesulphonamide and the reaction medium is agitated at a temperature of approximately 100° C. for approximately 2 hours 30 minutes left to return to ambient temperature, acidified with 4 ml of hydrochloric acid 2N, followed by extracting with 2×10 ml of ethyl acetate, drying, evaporating to dryness, impasting in 5 ml of ether, separating and drying at ambient temperature. In this way 356 mg of expected product is obtained in the form of beige crystals.

Stage 2: trans-N-[2-[(4-aminocyclohexyl)-amino]-9-cyclopentyl-9H-purin-6-yl]-3-bromo-benzene-sulphonamide dihydrochloride The operation is carried out as in Stage 2 of Example 8 and 400 mg of trans-1,4-diaminocyclohexane is taken to a temperature of approximately 150° C., 319 mg of the product obtained in Stage 1 above is added and the reaction medium is maintained at this temperature of 150° C. overnight, then left to return to ambient temperature followed by chromatography on silica eluting with CH₂CL/MeOH/NH₄OH (70/30/1). Then 4 ml of ethanol and 4 ml of ethanol/1.4N hydrochloric acid are added, followed by evaporating to dryness, impasting in 10 ml of ether/ethyl acetate in a proportion of 50/50 and drying under vacuum at a temperature of approximately 50° C. In this way 231 mg of expected product is obtained in the form of beige crystals.

| NMR in DMSO | |
|---|---|
| 1.34(m) 2H<br>1.50(m) 2H | } the axial H's of the cyclohexyl |
| 1.68(m) 2H<br>1.87(m) 2H<br>2.07(masked) | } the CH$_2$'s of the cyclopentyl |
| 2.07 | the equatorial H's of the cyclohexyl |
| 3.05(bs) 1H | axial H$_4$ |
| 3.60(bt) 1H | axial H$_1$ |
| 4.71(m) 1H | CH of the cyclopentyl |
| 7.54(t) 1H | H$_5$' |
| 7.80(ddd) 1H | H$_6$' |
| 7.95(dt) 1H | H$_4$' |
| 8.09(t) 1H | H$_2$' |
| 8.18(bs) | N=CH—N |
| 8.14 | assumed mobile H's |

EXAMPLE 27 trans-N-[2-[(4-aminocyclo-hexyl)-amino]-9-cyclopentyl-9H-purin-6-yl]-3-(trifluoro-methyl)-benzenesulphonamide dihydrochloride Stage 1: N-[[2-chloro-9-cyclopentyl-9H-purin-6-yl]-amino]-3-trifluoromethyl benzenesulphonamide The operation is carried out as in Stage 1 of Example 8 starting from 257 mg of the product obtained in Stage 1 of Example 1, 4 ml of dimethoxyethane (DME), 390 mg of caesium carbonate (CS$_2$CO$_3$) and 225 mg of 3-trifluoromethyl-benzenesulphonamide in place of the benzenesulphonamide and the reaction medium is agitated at a temperature of approximately 100° C. for approximately 2 hours 30 minutes, then left to return to ambient temperature, acidified with 4 ml of 2N hydrochloric acid, followed by extracting with 2×10 ml of ethyl acetate, drying and evaporating to dryness, impasting in 10 ml of ether, separating and drying at ambient temperature. In this way 273 mg of expected product is obtained in the form of colourless crystals.

Stage 2: trans-N-[2-[(4-aminocyclohexyl)-amino]-9-cyclopentyl-9H-purin-6-yl]-3-(trifluoromethyl)-benzenesulphonamide dihydrochloride The operation is carried out as in Stage 2 of Example 8 and 286 mg of trans-1,4-diaminocyclohexane is taken to a temperature of approximately 150° C., 222 mg of the product obtained in Stage 1 above is added and the reaction medium is maintained at this temperature of 150° C. for 3 hours, then at 110° C. overnight then at 150° C. for 2 hours, then left to return to ambient temperature. Chromatography is carried out on silica eluting with CH$_2$Cl$_2$/MeOH/NH$_4$OH (70/30/1), then 5 ml of ethanol and 4 ml of ethanol/1.4N hydrochloric acid are added, followed by evaporating to dryness, impasting in 5 ml of ether/ethyl acetate in a proportion of 50/50 and drying under vacuum to a temperature of approximately 50° C. In this way 166 mg of expected product is obtained in the form of beige crystals.

| NMR in DMSO | |
|---|---|
| 1.33(m) 2H<br>1.49(m) 2H | } the axial H's of the cyclohexyl |
| 1.67(bs) 2H<br>1.86(bs) 2H | |
| 2.08(masked) | the CH$_2$'s of the cyclopentyl |
| 2.05 | the equatorial H's of the cyclohexyl |
| 3.04(bs) 1H | axial H$_4$ |
| 3.60(bt) 1H | axial H$_1$ |
| 4.71(bs) 1H | CH of the cyclopentyl |
| 7.82(bt) 1H | H$_5$' |
| 7.96(bd) 1H | H$_4$' |
| 8.24(m) 2H | H$_6$', H$_2$' |
| 8.16(masked) | N=CH—N |
| 8.16 | assumed mobile H's |

EXAMPLE 28 trans-N-[2-[(4-aminocyclo-hexyl)-amino]-9-cyclopentyl-9H-purin-6-yl]-4-(1,1-dimethyl-ethyl)-benzenesulphonamide dihydrochloride Stage 1: N-[[2-chloro-9-cyclopentyl-9H-purin-6-yl]-amino]-4-(1,1-dimethylethyl)-benzenesulphonamide The operation is carried out as in Stage 1 of Example 8 starting from 257 mg of the product obtained in Stage 1 of Example 1, 4 ml of dimethoxyethane (DME), 390 mg of caesium carbonate (Cs$_2$CO$_3$) and 213 mg of 4-(1,1-dimethylethyl)benzene-sulphonamide in place of the benzenesulphonamide and the reaction medium is agitated at a temperature of approximately 100° C. for approximately 4 hours, left to return to ambient temperature and 4 ml of 2N hydrochloric acid and 5 ml of water are added, followed by extracting with 40 ml of ethyl acetate, drying, evaporating to dryness, impasting in 10 ml of ether, separating and drying at ambient temperature. In this way 253 mg of expected product is obtained in the form of beige crystals.

Stage 2: trans-N-[2-[(4-aminocyclohexyl)-amino]-9-cyclopentyl-9H-purin-6-yl]-4-(1,1-dimethylethyl) benzenesulphonamide dihydrochloride The operation is carried out as in Stage 2 of Example 8 and 286 mg of trans-1,4-diaminocyclohexane is taken to a temperature of approximately 150° C., 217 mg of the product obtained in Stage 1 above is added and the reaction medium is maintained at this temperature for approximately 5 hours, then left to return to ambient temperature, followed by chromatography on silica eluting with methylene chloride/methanol/ammonium hydroxide in a proportion of 70/30/1 and dissolving in 10 ml of ethanol. Then 4 ml of 1.4N hydrochloric acid/ethanol is added, followed by evaporating to dryness, impasting in 10 ml of ether and drying at ambient temperature. In this way 107 mg of expected product is obtained in the form of beige crystals.

| NMR in DMSO | |
|---|---|
| 1.31(s) | tBu |
| 1.34(partially masked) } 1.54(m) | the axial H's of the cyclohexyl |
| 1.69(m) 1.88(m) } 2.05(masked) | the CH2's of the cyclopentyl |
| 2.05 | the equatorial H's of the cyclohexyl |
| 3.04(bs) 1H | axial $H_4$ |
| 3.58(bt) 1H | axial $H_1$ |
| 4.71(m) 1H | CH of the cyclopentyl |
| 7.59 2H } 7.89 2H | AA'BB' $O_2$S-phenyl-tBu |
| 8.16(bs) >3H | N=C$\underline{H}$—N + assumed mobile H's |

EXAMPLE 29 trans (.+−.)-N2-(4-aminoocyclo-hexyl)-N6-propyl-9-(tetrahydro-3-thienyl)-9H-purin-6-amine dihydrochloride Stage 1: 2-chloro-N-propyl-9-(tetrahydro-3-thienyl)-9H-purin-2,6-diamine.

The operation is carried out as in Stage 2 of Example 5 starting from 160 mg of the product obtained in Stage 1 of Example 5, 3 ml of butanol and using 0.100 ml of 1-propanamine in place of the benzylamine and the reaction medium is taken to a temperature of approximately 80 to 85° C. for 24 hours, left to return to ambient temperature, followed by evaporating to dryness, impasting in 10 ml of ethyl acetate at ambient temperature, separating, washing with 10 ml and drying under vacuum at a temperature of approximately 50° C. In this way 123 mg of expected product is obtained in the form of white crystals.

Stage 2: trans(.+−.)-N2-(4-aminocyclo-hexyl)-N6-propyl-9-(tetrahydro-3-thienyl)-9H-purin-2,6-diamine dihydrochloride The operation is carried out as in Stage 3 of Example 5 starting from 400 mg of trans-1,4-diaminocyclohexane and 106 mg of the product obtained in Stage 1 above, the reaction medium is taken to a temperature of approximately 140 to 145° C. for approximately 6 hours then left to return to ambient temperature. After purification on silica eluting with methanol/ammonium hydroxide ($NH_4OH$) in a proportion of 98/2 and salification with 1.4 N hydrochloric acid in ethanol, 30 mg of expected product is obtained in the form of pink beige crystals.

| NMR in DMSO | |
|---|---|
| 0.94(t) 3H | C$\underline{H}_2$—CH$_2$—CH$_2$—NH— |
| 1.64(m) 2H | CH$_2$—C$\underline{H}_2$—CH$_2$—NH |
| 3.55(masked) | CH$_2$—CH$_2$—C$\underline{H}_2$—NH |
| 1.43(m) 4H | the axial H's of the cyclohexyl |
| 2.07(bt) 4H | the equatorial H's of the cyclohexyl |
| 2.43(m) masked | S—C$\underline{H}_2$—C$\underline{H}_2$ |
| 2.98(m) 2H | S—C$\underline{H}_2$—CH$_2$ |
| 3.05(masked) | assumed axial $H_4$ |
| 3.72(bt) 1H | axial $H_1$ |
| 3.27(m) | S—C$\underline{H}_2$—CH |
| 5.03(m) 1H | S—CH$_2$—C$\underline{H}$ |
| 8.01(bs) 3H | N=CH—N + mobile H's |
| 8.18(bs) } 9.06(bs) | mobile H's |

EXAMPLE 30 trans(.+−.)-N2-(4-aminocyclo-hexyl)-N6-[(3-iodophenyl)-methyl]-9-(tetrahydro-3-thienyl)-9H-purin-2,6-diamine dihydrochloride Stage 1: 2-chloro-N-[(3-iodophenyl)-methyl]-9-(tetrahydro-3-thienyl)-9H-purin-6-amine The operation is carried out as in Stage 2 of Example 5 starting from 160 mg of the product obtained in Stage 1 of Example 5, 3 ml of butanol and using 0.114 ml of 3-iodobenzenemethanamine in place of the benzylamine and the reaction medium is taken to a temperature of approximately 80 to 85° C. for approximately 30 hours, left to return to ambient temperature, diluted with 3 ml of isopropanol, placed for approximately one hour at a temperature of approximately 0° C., followed by separating, washing with 5 ml of isopropanol and drying under vacuum to a temperature of approximately 50° C. After purification on silica eluting with methylene chloride/ethyl acetate in a proportion 90/10, 173 mg of expected product is thus obtained in the form of white-yellow crystals.

Stage 2: trans(.+−.)-N2-(4-aminocyclo-hexyl)-N6-[(3-iodophenyl)-methyl]-9-(tetrahydro-3-thienyl)-9H-purin-2,6-diamine dihydrochloride The operation is carried out as in Stage 3 of Example 5 starting from 330 mg of trans-1,4-diaminocyclohexane and 137 mg of the product obtained in Stage 1 above, the reaction medium is taken to a temperature of approximately 140 to 145° C. for approximately 6 hours then left to return to ambient temperature and left overnight. After purification on silica eluting with methanol/ammonium hydroxide ($NH_4OH$) in a proportion of 98/2 salification is carried out with 1.4 N hydrochloric acid in ethanol, followed by separating, washing and drying at a temperature of approximately 50° C. In this way 74 mg of expected product is obtained in the form of brown-pink crystals.

| NMR in DMSO | |
|---|---|
| 1.35(m) } 1.49(m) 4H | the axial H's of the cyclohexyl |
| 2.02(bd) 4H | the equatorial H's of the cyclohexyl |
| 2.42 } 2.54 masked in part | S—C$\underline{H}_2$—C$\underline{H}_2$ |

-continued

| NMR in DMSO | |
|---|---|
| 2.97(m) 3H | S—C$\underline{H}_2$—CH$_2$ + H$_4$ assumed axial |
| 3.27(m) 2H | S—C$\underline{H}_2$—CH |
| 3.71(bt) masked in part | axial H$_1$ |
| 4.80(bs) 2H | NH—C$\underline{H}_2$-phenyl |
| 5.05(m) 1H | N—C$\underline{H}$—CH$_2$—S— |
| 7.16(t) 1H | H$_5$' |
| 7.45(d) 1H } H$_4$', H$_6$' | |
| 7.64(d) 1H } | |
| 7.80(s) 1H | H$_2$' |
| 8.04(bs) >2H | N=CH—N + assumed mobile H's |
| 8.33(bs) } assumed mobile H's | |
| 9.37(bs) } | |

EXAMPLE 31 trans(.+−.)-N2-(4-aminocyclo-hexyl)-N6-phenyl-9-(tetrahydro-3-thienyl)-9H-purin-2,6-diamine dihydrochloride Stage 1: 2-chloro-N-phenyl-9-(tetrahydro-3-thienyl)-9H-purin-6-amine The operation is carried out as in Stage 2 of Example 5 starting from 160 mg of the product obtained in Stage 1 of Example 5, 3 ml of butanol and using 0.055 ml of aniline in place of the benzylamine and the reaction medium is taken to a temperature of approximately 80 to 85° C. for 20 hours, left to return to ambient temperature, diluted with 5 ml of isopropanol, placed for approximately one hour at a temperature of approximately 0° C., followed by separating, washing with 5 ml of isopropanol and drying under vacuum to a temperature of approximately 50° C. After purification on silica eluting with methylene chloride/ethyl acetate in a proportion of 90/10, 173 mg of expected product is thus obtained in the form of white crystals.

Stage 2: trans(.+−.)-N2-(4-aminocyclo-hexyl)-N6-phenyl-9-(tetrahydro-3-thienyl)-9H-purin-2,6-diamine dihydrochloride The operation is carried out as in Stage 3 of Example 5 starting from 536 mg of trans-1,4-diaminocyclohexane and 156 mg of the product obtained in Stage 1 above, the reaction medium is taken to a temperature of approximately 140 to 145° C. for approximately 4 hours 30 minutes then left to return to ambient temperature. After purification on silica eluting with methanol/ammonium hydroxide (NH$_4$OH) in a proportion of 98/2 salification is carried out with 1.4 N hydrochloric acid in ethanol, followed by separating, washing and drying at a temperature of approximately 50° C. In this way 145 mg of expected product is obtained in the form of pink beige crystals.

| NMR in DMSO | |
|---|---|
| 1.39(m) } the axial H's of the cyclohexyl | |
| 1.52(m) 4H } | |
| 2.07 4H | the equatorial H's of the cyclohexyl |
| 2.46(masked) } —C$\underline{H}_2$—CH$_2$—S | |
| 2.60(m) 1H } | |
| 3.00(m) 3H | C$\underline{H}_2$—CH$_2$—S + assumed axial H$_4$ |
| 3.32(m) 2H | —CH—C$\underline{H}_2$—S |
| 5.13(m) 1H | —C$\underline{H}$—CH$_2$—S |
| 3.71(m) 1H | axial H$_1$ |
| 7.11(t) 1H } | |
| 7.39(t) 2H } aromatic H | |
| 7.94(d) 2H } | |
| 8.08(bs) >2H | N=C$\underline{H}$—N + mobile H's |
| 8.86 } assumed mobile H's | |
| 10.52 } | |

EXAMPLE 32 dihydrochloride of ethyl trans(.+−.)-4-[[2-[(4-amino-cyclohexyl)-amino]-9-(tetrahydro-3-thienyl)-9H-purin-6-yl]-amino]-benzoate Stage 1: ethyl 4-((2-chloro-9-(tetrahydro-3-thienyl)-9H-purin-6-yl)-amino)-benzoate The operation is carried out as in Stage 2 of Example 5 starting from 160 mg of the product obtained in Stage 1 of Example 5, 3 ml of butanol and using 100 mg of ethyl 4-aminobenzoate in place of the benzylamine and the reaction medium is taken to a temperature of approximately 80 to 85° C. for 30 hours, left to return to ambient temperature, diluted with 3 ml of isopropanol, placed for approximately one hour at a temperature of approximately 0° C., followed by separating, washing with 5 ml of isopropanol and drying under vacuum at a temperature of approximately 50° C. After purification on silica eluting with methylene chloride/ethyl acetate in a proportion of 90/10, 202 mg of expected product is thus obtained in the form of white-cream crystals.

Stage 2: dihydrochloride of ethyl trans(.+−.)-4-[[2-[(4-amino-cyclohexyl)-amino]-9-(tetrahydro-3-thienyl)-9H-purin-6-yl]-amino]-benzoate The operation is carried out as in Stage 3 of Example 5 starting from 513 mg of trans-1,4-diaminocyclohexane which is taken to a temperature of approximately 70 to 75° C. and 181 mg of the product obtained in Stage 1 above is added, the reaction medium is taken to a temperature of approximately 140 to 145° C. for 4 hours 30 minutes then left to return to ambient temperature. After purification on silica eluting with methanol/ammonium hydroxide (NH$_4$OH) in a proportion of 98/2 and salification with 1.4 N hydrochloric acid in ethanol, separation is carried out, followed by washing with 10 ml of ethanol and drying at a temperature of approximately 50° C. In this way 150 mg of expected product is obtained in the form of white crystals.

| NMR in DMSO | | |
|---|---|---|
| 1.33(t) 3H | C$\underline{H}_3$—CH$_2$—O | |
| 4.31(q) | CH$_3$—C$\underline{H}_2$—O | |
| 1.45(m) 4H | the axial H's of the cyclohexyl | |
| 2.08(bt) 4H | the equatorial H's of the cyclohexyl | |
| 2.43(dd) } | CH$_2$ in position 4 | |
| 2.58(dd) } | | |
| 2.98(m) 2H | CH$_2$ in position 5 | |
| 3.00(masked) | axial H$_4$' | |
| 3.31(m) 2H | CH$_2$ in position 2 | |
| 3.70(bt) 1H | axial H$_1$' | |
| 5.12(m) 1H | H$_3$ | |
| 7.95 2H } | NH-phenyl-C=O | |
| 8.16 2H AB } | | |
| 8.08(masked) | N=C$\underline{H}$—N | |
| 8.08 } | | |
| 8.83 } assumed mobile H's | | |
| 10.73 } | | |

| NMR in DMSO | | |
|---|---|---|
| 1.39(m) } | the axial H's of the cyclohexyl | |
| 1.52(m) 4H } | | |
| 2.06(bt) 4H | the equatorial H's of the cyclohexyl | |
| 2.42(m) } | S—CH$_2$—C$\underline{H}_2$ | |
| 2.59(m) } | | |
| 2.99(m) | S—C$\underline{H}_2$—CH$_2$ | |
| 3.00(masked) | assumed axial H$_4$ | |
| 3.31(m) | S—C$\underline{H}_2$—CH | |
| 5.10(m) 1H | S—CH$_2$—C$\underline{H}$ | |
| 3.69(bt) 1H | assumed axial H$_1$ | |
| 7.33 2H } | O-phenyl-N | |
| 8.09 2H AB } | | |
| 8.04 >2H | N=C$\underline{H}$—N + mobile H's | |
| 8.60 } assumed mobile H's | | |
| 10.35 } | | |

EXAMPLE 33 trans(.+−.)-N2-(4-amino-cyclohexyl)-9-(tetrahydro-3-thienyl)-N6-[4-(trifluoro-methoxy)-phenyl]-9H-purin-2,6-diamine dihydrochloride.

Stage 1: 2-chloro-9-(tetrahydro-3-thienyl)-N-[4-(trifluoromethoxy)-phenyl]-9H-purin-6-amine The operation is carried out as in Stage 2 of Example 5 starting from 160 mg of the product obtained in Stage 1 of Example 5, 3 ml of butanol and using 0.081 ml of 4-(trifluoro-methoxy)-benzenamine in place of the benzylamine and the reaction medium is taken to a temperature of approximately 80 to 85° C. for approximately 20 hours, left to return to ambient temperature, diluted with 3 ml of isopropanol, placed for approximately one hour at a temperature of approximately 0° C., followed by separating, washing with 5 ml of isopropanol and drying under vacuum at a temperature of approximately 50° C. After purification on silica eluting with methylene chloride/ethyl acetate in a proportion of 90/10, 203 mg of expected product is obtained in the form of white crystals.

Stage 2: trans(.+−.)-N2-(4-aminocyclo-hexyl)-9-(tetrahydro-3-thienyl)-N6-[4-(trifluoromethoxy)-phenyl]-9H-purin-2,6-diamine dihydrochloride The operation is carried out as in Stage 3 of Example 5 starting from 186 mg of the product obtained in Stage 1 above and 513 mg of trans-1,4-diaminocyclohexane, the reaction medium is taken to a temperature of approximately 140 to 145° C. for 4 hours 30 minutes then left to return to ambient temperature. After purification on silica eluting with methanol/ammonium hydroxide (NH$_4$OH) in a proportion of 98/2 and salification with 1.4 N hydrochloric acid in ethanol, separation is carried out, followed by washing with 10 ml of ethanol and drying at a temperature of approximately 50° C. In this way 117 mg of expected product is obtained in the form of pink beige crystals.

EXAMPLE 34 trans (.+−.)-N2-(4-aminocyclo-hexyl)-N6-phenyl-9-(tetrahydro-3-furanyl)-9H—purin-2,6-diamine dihydrochloride Stage 1: (.+−.)-2-chloro-N-phenyl-9-(tetrahydro-3-furanyl)-9H-purin-6-amine.

The operation is carried out as in Stage 2 of Example 2 from 200 mg (0.77 mM) of the product obtained in Stage 1 of Example 2 and 3 ml of butanol and using 0.088 ml of aniline (0.96 mmole) in place of the benzylamine. In this way 213 mg of expected product is obtained in the form of white crystals.

Stage 2: trans (.+−.)-N2-(4-aminocyclo-hexyl)-N6-phenyl-9-(tetrahydro-3-furanyl)-9H— purine-2,6-diamine dihydrochloride The operation is carried out as in Stage 3 of Example 2 starting from 198 mg of the product obtained in Stage 1 above and 716 mg of trans-1,4-diaminocyclohexane. After purification on silica eluting with methanol/ammonium hydroxide (NH4OH) in a proportion of 98/2 and salification with 1.4 N hydrochloric acid in ethanol, 169 mg of expected product is obtained in the form of pink beige crystals

| NMR in DMSO | | |
|---|---|---|
| 1.39(m) 2H | | |
| 1.53(m) 2H | the axial H's of the cyclohexyl | |
| 2.08(m) 4H | the equatorial H's of the cyclohexyl | |
| 2.38(m) 1H } | O—CH$_2$—C$\underline{H}_2$ | |
| 2.55(masked) } | | |
| 3.03(bs) 1H | axial H$_4$ | |
| 3.73(bt) 1H | axial H$_1$ | |
| 3.89(m) 1H } | O—C$\underline{H}_2$—CH$_2$ | |
| 4.13(m) 1H } | | |
| 4.04(m) 2H | O—CH$_2$—CH | |
| 5.14(m) 1H | N—C$\underline{H}$ | |
| 7.10(t) 1H | | |

-continued

| NMR in DMSO | |
|---|---|
| 7.38(t) 2H } aromatic H | |
| 7.93(d) 21H | |
| 8.06(bs) <3H | CH—N + $NH_2$ |
| 8.68 to 10.36 | mobile H's |

EXAMPLE 35 trans(.+−.)-N2-(4-aminocyclo-hexyl)-9-(tetrahydro-3-furanyl)-N6-[(4-trifluoromethoxy)-phenyl]-9H-purin-2,6-diamine dihydrochloride

Stage 1: (.+−.)-2-chloro-9-(tetrahydro-3-furanyl)-N-[4-(trifluoromethoxy)-phenyl]-9H-purin-6-amine The operation is carried out as in Stage 2 of Example 2 starting from 200 mg (0.77 mmoles) of the product obtained in Stage 1 of Example 2 and 3 ml of butanol and using 0.130 ml of 4-(trifluoromethoxy)-benzenamine (0.96 mmoles) in place of the benzylamine. In this way 72 mg of expected product is obtained in the form of white crystals.

Stage 2: trans(.+−.)-N2-(4-aminocyclo-hexyl)-9-(tetrahydro-3-furalyl)-N6-[(4-trifluoromethoxy)-phenyl]-9H-purin-2,6-diamine dihydrochloride The operation is carried out as in Stage 3 of Example 2 starting from 153 mg of the product obtained in Stage 1 above and 433 mg of trans-1,4-diaminocyclohexane. After purification on silica eluting with methanol/ammonium hydroxide ($NH_4OH$) in a proportion of 98/2 and salification with 1.4 N hydrochloric acid in ethanol, 114 mg of expected product is obtained in the form of white cream crystals.

| NMR in DMSO | |
|---|---|
| 1.38(m) 2H } the axial H's of the cyclohexyl | |
| 1.51(m) 2H | |
| 2.07(bt) 4H | the equatorial H's of the cyclohexyl |
| 2.36(m) 1H } O—$CH_2$—$CH_2$ | |
| 2.50(masked) | |
| 3.03(bs) 1H | axial $H_4$ |
| 3.70(masked) | assumed axial $H_1$ |
| 3.88(masked) } O—$CH_2$—$CH_2$ | |
| 4.12(m) 1H | |
| 4.02(d) 2H | O—$CH_2$—CH |
| 5.10(m) 1H | N—CH |
| 7.31 2H } AA'BB' NH-phenyl-$OCF_3$ | |
| 8.09 2H | |
| 8.00(bd) <3H | N=CH—N + $NH_2$ |
| 8.41(s) to 10.18(s) | mobile H's |

EXAMPLE 36 trans-N2-(4-aminocyclohexyl)-9-(1-ethylpropyl)-N6-propyl-9H-purin-2,6-diamine dihydrochloride

Stage 1: 2-chloro-9-(1-ethylpropyl)-N-propyl-9H-purin-6-amine.

The operation is carried out as in Stage 2 of Example 3 from 200 mg of the product obtained in Stage 1 of Example 3 and 4 ml of butanol and using 0.129 ml of propylamine in place of the benzylamine. Agitation is carried out at ambient temperature then the reaction medium is taken to a temperature of 80 to 85° C. for 5 hours, left to return to ambient temperature, followed by evaporating to dryness then impasting in 5 ml of pentane at ambient temperature, separating, washing and drying at a temperature of approximately 50° C. After purification on silica eluting with methylene chloride/ethyl acetate in a proportion of 90/10, 145 mg of expected product is obtained in the form of white crystals.

Stage 2: trans-N2-(4-aminocyclohexyl)-9-(1-ethylpropyl)-N6-propyl-9H-purin-2,6-diamine dihydrochloride The operation is carried out as in Stage 3 of Example 3 starting from 121 mg of the product obtained in Stage 1 above and 489 mg of trans-1,4-diaminocyclohexane and the reaction medium is taken to a temperature of 140 to 150° C. for 4 hours then cooled down to 70–80° C., diluted with 20 ml of water/ethyl acetate in a proportion of 50/50 and left to settle, followed by washing with 10 ml of water and 5 ml of an aqueous solution of sodium chloride, drying and evaporating to dryness. After purification on silica eluting with methanol/ammonium hydroxide ($NH_4OH$) in a proportion of 98/2 and salification with 1.4N hydrochloric acid in ethanol, 114 mg of expected product is obtained in the form of crystals.

| NMR in DMSO | |
|---|---|
| 0.77(t) 6H | $CH_3$—$CH_2$—CH |
| 0.95(t) 3H | $CH_3$—$(CH_2)_2$ |
| 1.39(m) } the axial H's of the cyclohexyl | |
| 1.49(m) 4H | |
| 1.65(m) 2H | $CH_3$—$CH_2$—$CH_2$—NH |
| 1.92(m) 4H | $CH_2$—$CH_3$ |
| 2.07(m) 4H | the equatorial H's of the cyclohexyl |
| 3.05(bs) 1H | axial $H_4$ |
| 3.56(bs) | NH—$CH_2$—$CH_2$—$CH_3$ |
| 3.68(bt) 1H | axial $H_1$ |
| 4.19(m) | N—CH |
| 8.08(bs) 3H | $NH_2$ + N=CH—N |
| 8.22 to 9.22 | assumed mobile H's |

EXAMPLE 37 trans-N2-(4-aminocyclohexyl)-9-(1-ethylpropyl)-N6-phenyl-9H-purin-2,6-diamine dihydrochloride

Stage 1: 2-chloro-9-(1-ethylpropyl)-N-phenyl-9H-purin-6-amine.

The operation is carried out as in Stage 2 of Example 3 starting from 200 mg (0.77 mmoles) of the product obtained in Stage 1 of Example 3 and 4 ml of butanol and using 0.088 ml (0.96 mmoles) of aniline in place of the benzylamine. Agitation is carried out at ambient temperature then the reaction medium is taken to a temperature of 80 to 85° C. for 22 hours, left to return to ambient temperature, diluted with 4 ml of isopropanol, left for two days at a temperature of approximately 0° C., followed by separating, washing with 10 ml of isopropanol and drying at a temperature of approximately 50° C.

After purification on silica eluting with methylene chloride/ethyl acetate in a proportion of 90/10, 104 mg of expected product is obtained in the form of white crystals.

Stage 2: trans-N2-(4-aminocyclohexyl)-9-(1-ethylpropyl)-N6-phenyl-9H-purin-2,6-diamine dihydrochloride The operation is carried out as in Stage 3 of Example 3 starting from 97 mg of the product obtained in Stage 1 above and 350 mg of trans-1,4-diaminocyclohexane and the reaction medium is taken to a temperature of 140 to 150° C. for approximately 4 hours then cooled down to 70–80° C. and diluted with 20 ml of water/ethyl acetate in a proportion of 50/50, left to settle, followed by washing with 10 ml of water and 5 ml of an aqueous solution of sodium chloride, drying and evaporating to dryness. After purification on silica eluting with methanol/ammonium hydroxide ($NH_4OH$) in a proportion of 98/2 and salification with 1.4 N hydrochloric acid in ethanol, 66 mg of expected product is obtained in the form of crystals.

| NMR in DMSO | |
|---|---|
| 0.82(t) 6H | $C\underline{H_3}$—$CH_2$— |
| 1.96(masked) | $CH_3$—$C\underline{H_2}$ |
| 1.39(m) 1.52(m) 4H | the axial H's of the cyclohexyl |
| 2.08(m) | the equatorial H's of the cyclohexyl |
| 3.02(bs) 1H | axial $H_4$ |
| 3.70(tt) 1H | axial $H_1$ |
| 4.32(m) | N—$C\underline{H}$—$CH_2$— |
| 7.11 7.39 7.93 | aromatic H's |
| 8.03(bs) >2H | $NH_2$ + N=$C\underline{H}$—N |
| 8.78 to 10.40 | mobile H's |

EXAMPLE 38 trans-N-[2-[(4-aminocyclo-hexyl)-amino]-9-cyclopentyl-9H-purin-6-yl]-4-ethoxy-benzenesulphonamide dihydrochloride

Stage 1: N-[[2-chloro-9-cyclopentyl-9H-purin-6-yl]-amino]-4-ethoxy-benzenesulphonamide.

The operation is carried out as in Stage 1 of Example 8 starting from 257 mg of the product obtained in Stage 1 of Example 1, 4 ml of dimethoxyethane (DME), 390 mg of caesium carbonate ($Cs_2CO_3$) and 201 mg of 4-ethoxy-benzenesulphonamide in place of the benzenesulphonamide and the reaction medium is agitated at a temperature of approximately 100° C. for approximately 2 hours 30 minutes left to return to ambient temperature, acidified with 4 ml of 2N hydrochloric acid, followed by extracting with 2×10 ml of ethyl acetate, drying, filtering, evaporating to dryness, impasting in 10 ml of ether and drying at ambient temperature. In this way 325 mg of expected product is obtained in the form of beige crystals.

Stage 2: trans-N-[2-[(4-aminocyclohexyl)-amino]-9-cyclopentyl-9H-purin-6-yl]-4-ethoxy-benzene-sulphonamide dihydrochloride The operation is carried out as in Stage 2 of Example 8 and 400 mg of trans-1,4-diaminocyclohexane is taken taken to a temperature of approximately 150° C., 295 mg of the product obtained in Stage 1 above is added, and the reaction medium is maintained at this temperature for approximately 7 hours 30 minutes, then left to return to ambient temperature. Chromatography is carried out on silica eluting with methylene chloride/methanol/ammonium hydroxide in a proportion of 70/30/1 then 90/10/1 in order to purify the product. Then 10 ml of ethanol and 3 ml of 1.4N hydrochloric acid/ethanol are added, followed by evaporating to dryness, impasting in 10 ml of ether and drying under vacuum at a temperature of approximately 60° C. In this way 146 mg of expected product is obtained in the form of beige crystals.

| NMR in DMSO | |
|---|---|
| 1.34(masked) 1.51(m) 2H | the axial H's of the cyclohexyl |
| 1.34(t) 4.12(a) 2H | $C\underline{H_3}$—$CH_2$—O $CH_3$—$C\underline{H_2}$—O |
| 1.67(m) 2H 1.86(m) 2H 2.05(masked) | the CH2's of the cyclopentyl |
| 2.05(bd) | the equatorial H's of the cyclohexyl |
| 3.03(bs) 1H | axial $H_4$ |
| 3.57(bt) 1H | axial $H_1$ |
| 4.71(m) 1H | CH of the cyclopentyl |
| 7.08 2H 7.89 2H AA'BB' | O-phenyl-$SO_2$— |
| 8.11 | N=CH—N + $NH_2$ |
| 4.79 8.27 | the mobile H's |

EXAMPLE 39 trans-N-[2-[(4-aminocyclo-hexyl)-amino]-9-cyclopentyl-9H-purin-6-yl]-4-bromo-benzene-sulphonamide dihydrochloride Stage 1: 4-bromo-N-[[2-chloro-9-cyclopentyl-9H-purin-6-yl]-amino]-benzenesulphonamide The operation is carried out as in Stage 1 of Example 8 starting from 257 mg of the product obtained in Stage 1 of Example 1, 4 ml of dimethoxyethane (DME), 390 mg of caesium carbonate ($Cs_2CO_3$) and 236 mg of 4-bromo-benzenesulphonamide in place of the benzenesulphonamide and the reaction medium is agitated at a temperature of approximately 100° C. for approximately 2 hours 30 minutes left to return to ambient temperature, acidified with 4 ml of 2N hydrochloric acid, followed by extracting with 2×10 ml of ethyl acetate, drying, filtering, evaporating to dryness, impasting in 10 ml of ether and drying at ambient temperature. In this way 226 mg of expected product is obtained in the form of beige crystals.

Stage 2: trans-N-[2-[(4-aminocyclohexyl)-amino]-9-cyclopentyl-9H-purin-6-yl]-4-bromo-benzene-sulphonamide dihydrochloride The operation is carried out as in Stage 2 of Example 8 and 228 mg of trans-1,4-diaminocyclohexane is taken to a temperature of approximately 150° C., 182 mg of the product obtained in Stage 1 above is added and the reaction medium is maintained at this temperature for approximately 8 hours. Chromatography is carried out on silica eluting with methylene chloride/methanol/ammonium hydroxide in a proportion of 80/20/1, then 10 ml of ethanol, 4 ml of 1.4N hydrochloric acid/ethanol are added, followed by leaving overnight, evaporating to dryness, impasting in 10 ml of ether and drying under vacuum at a temperature of approximately 60° C. In this way 74 mg of expected product is obtained in the form of beige crystals.

| NMR in DMSO | |
|---|---|
| 1.34(m) 2H  <br> 1.50(m) 2H | } the axial H's of the cyclohexyl |
| 2.07(m) 4H | the equatorial H's of the cyclohexyl |
| 3.04(bs) 1H | axial $H_4$ |
| 3.58(bt) 1H | axial $H_1$ |
| 4.70(m) 1H | N—CH of the cyclopentyl |
| 1.68(m) 2H  <br> 1.87(m) 2H  <br> 2.07(m) 4H | } the CH2's of the cyclopentyl |
| 7.75  <br> 7.88 | } AA'BB'-phenyl- |
| 8.01(s)  <br> 8.03(bs) 3H | } N—CH=N + mobile H's |

EXAMPLE 40 trans-N-[2-[(4-aminocyclo-hexyl)-amino]-9-cyclopentyl-9H-purin-6-yl]-4-methyl-benzene-sulphonamide dihydrochloride Stage 1: N-[[2-chloro-9-cyclopentyl-9H-purin-6-yl]-amino]-4-methyl-benzenesulphonamide.

The operation is carried out as in Stage 1 of Example 8 starting from 257 mg of the product obtained in Stage 1 of Example 1, 4 ml of dimethoxyethane (DME), 390 mg of caesium carbonate ($Cs_2CO_3$) and 171 mg of 4-methyl-benzenesulphonamide in place of the benzenesulphonamide and the reaction medium is agitated at a temperature of approximately 100° C. for approximately 2 hours 30 minutes left to return to ambient temperature and acidified with 4 ml of 2N hydrochloric acid, followed by extracting with 2×10 ml of ethyl acetate, drying, filtering, evaporating to dryness, impasting in 10 ml of ether and drying at ambient temperature. In this way 292 mg of expected product is obtained in the form of beige crystals.

Stage 2: trans-N-[2-[(4-aminocyclohexyl)-amino]-9-cyclopentyl-9H-purin-6-yl]-4-methyl-benzene-sulphonamide dihydrochloride The operation is carried out as in Stage 2 of Example 8 and 285 mg of trans-1,4-diaminocyclohexane is taken to a temperature of approximately 150° C., 196 mg of the product obtained in Stage 1 above is added and the reaction medium is maintained at this temperature for approximately 7 hours. Chromatography is carried out on silica eluting with methylene chloride/methanol/ammonium hydroxide in a proportion of 80/20/1, then 8 ml of ethanol, 4 ml of 1.4N hydrochloric acid/ethanol are added and followed by leaving overnight, evaporating to dryness, impasting in 10 ml of ether and drying under vacuum at a temperature of approximately 60° C. In this way 112 mg of expected product is obtained in the form of beige crystals.

| NMR in DMSO | |
|---|---|
| 1.33(m) 2H  <br> 1.51(m) 2H | } the axial H's of the cyclohexyl |
| 1.68(m) 2H  <br> 1.87(m) 2H  <br> 2.06(m) 4H | } the CH2's of the cyclopentyl |
| 2.06(bd) 4H | the equatorial H's of the cyclohexyl |
| 3.02(bs) 1H | axial $H_4$ |
| 3.58(bt) 1H | axial $H_1$ |
| 4.71(m) 1H | CH of the cyclopentyl |
| 7.37 2H  <br> 7.85 2H | } AA'BB'-phenyl-SO2 |
| 8.12 <3H | N—CH=N + $NH_2$ |
| 8.16(s) 1H | mobile H |

EXAMPLE 41 trans-N2-(4-aminocyclohexyl-9-(1-ethylpropyl)-N6-[(3-iodophenyl)-methyl]-9H-purin-2,6-diamine dihydrochloride

Stage 1: 2-chloro-9-(1-ethylpropyl)-N-[(3-iodophenyl)-methyl]-9H-purin-6-amine.

The operation is carried out as in Stage 2 of Example 3 starting from 200 mg of the product obtained in Stage 1 of Example 3 and 4 ml of butanol and using 0.123 ml of 3-iodo-benzenemethanamine in place of the benzylamine. Agitation is carried out at ambient temperature then the reaction medium is taken to a temperature of 80 to 85° C. for 22 hours, left to return to ambient temperature, diluted with 4 ml of isopropanol, left for three hours at a temperature of approximately 0° C., followed by separating, washing with 10 ml of isopropanol and drying at a temperature of approximately 50° C. After purification on silica eluting with cyclohexane/ethyl acetate/methylene chloride in a proportion of 70/15/15, 235 mg of expected product is obtained in the form of white crystals.

Stage 2: trans-N2-(4-aminocyclohexyl-9-(1-ethylpropyl)-N6-[(3-iodophenyl)-methyl]-9H-purin-2,6-diamine dihydrochloride The operation is carried out as in Stage 3 of Example 3 starting from 226 mg of the product obtained in Stage 1 above and 565 mg of trans-1,4-diaminocyclohexane and the reaction medium is taken to a temperature of 140 to 150° C. for 4 hours then cooled down to 70–80° C., diluted with 20 ml of water/ethyl acetate in a proportion of 50/50 and left to settle, followed by washing with 10 ml of water and 5 ml of an aqueous solution of sodium chloride, drying and evaporating to dryness. After purification on silica eluting with methanol/ammonium hydroxide (NH4OH) in a proportion of 98/2 and salification with 1.4 N hydrochloric acid in ethanol, 160 mg of expected product is obtained in the form of crystals.

| NMR in DMSO | |
|---|---|
| 0.79(t) 6H | C$\underline{H_3}$—CH$_2$—CH |
| 1.93(m) 4H | CH$_3$—C$\underline{H_2}$—CH |
| 1.37(m) 2H | } the axial H's of the cyclohexyl |
| 1.50(m) 2H | |
| 2.05(m) 4H | the equatorial H's of the cyclohexyl |
| 3.03(bs) 1H | axial H$_4$ |
| 3.70(bt) 1H | axial H$_1$ |
| 4.24(m) | C$\underline{H}$—(CH$_2$—CH$_3$)$_2$ |
| 4.83(bs) 2H | NH—C$\underline{H_2}$-phenyl |
| 7.17(t) 1H | H$_5$' |
| 7.46(d) 1H | } H$_4$' H$_6$' |
| 7.64(dt) 1H | |
| 7.82(s) 1H | H$_2$' |
| 8.04(bs) 3H | NH$_2$ + N=C$\underline{H}$—N |
| 8.31 to 9.32 | mobile H's |

EXAMPLE 42 trans-N2-(4-aminocyclohexyl)-9-(1-ethylpropyl)-N6-[4-(trifluoromethoxy)-phenyl]-9H-purin-2,6-diamine dihydrochloride

Stage 1: 2-chloro-9-(1-ethylpropyl)-N-[4-(trifluoromethoxy)-phenyl]-9H-purin-6-amine The operation is carried out as in Stage 2 of Example 3 starting from 200 mg of the product obtained in Stage 1 of Example 3 and 4 ml of butanol and using 0.13 ml of 4-(trifluoromethoxy)-benzenamine in place of the benzylamine. The reaction medium is agitated at ambient temperature then taken to a temperature of 80 to 85° C. for 22 hours, left to return to ambient temperature, diluted with 4 ml of isopropanol, left for four hours at a temperature of approximately 0° C., followed by separating, washing with 10 ml of isopropanol and drying at a temperature of approximately 50° C.

After purification on silica eluting with cyclohexane/ethyl acetate/methylene chloride in a proportion of 70/15/15, 169 mg of expected product is obtained in the form of white crystals.

Stage 2: trans-N2-(4-aminocyclohexyl)-9-(1-ethylpropyl)-N6-[4-(trifluoromethoxy)-phenyl]-9H-purin-2,6-diamine dihydrochloride The operation is carried out as in Stage 3 of Example 3 starting from 160 mg of the product obtained in Stage 1 above and 456 mg of trans-1,4-diaminocyclohexane and the reaction medium is taken to a temperature of 140 to 150° C. for 4 hours then cooled down to 70–80° C. and diluted with 20 ml of water/ethyl acetate in a proportion of 50/50 and left to settle, followed by washing with 10 ml of water and 5 ml of an aqueous solution of sodium chloride, drying and evaporating to dryness. After purification on silica eluting with methanol/ammonium hydroxide (NH$_4$OH) in a proportion of 98/2 and salification with 1.4 N hydrochloric acid in ethanol, 149 mg of expected product is obtained in the form of crystals.

| NMR in DMSO | |
|---|---|
| 0.77(t) 6H | (C$\underline{H_3}$—CH$_2$)$_2$—CH |
| 1.95(m) | (CH$_3$—C$\underline{H_2}$)$_2$—CH |
| 1.34(m) 2H | |
| 1.50(m) 2H | the axial H's of the cyclohexyl |
| 2.03(m) 4H | the equatorial H's of the cyclohexyl |
| 3.02(bs) 1H | axial H$_4$ |
| 3.64(bt) 1H | axial H$_1$ |
| 4.30(m) 1H | C$\underline{H}$—(CH$_2$—CH$_3$)$_2$ |
| 7.38 | |
| 8.09 2H AA'BB' | F$_3$CO-phenyl-N |
| 8.07 | NH$_2$ + N=C$\underline{H}$—N |
| 8.93 to 10.76 | assumed mobile H's |

EXAMPLE 43 dihydrochloride of ethyl trans-4-[[2-[(4-aminocyclo-hexyl)-amino]-9-(1-ethylpropyl)-9H-purin-6-yl-]amino]-benzoate

Stage 1: ethyl 4-[[2-chloro-9-(1-ethylpropyl)-9H-purin-6-yl-]amino]-benzoate The operation is carried out as in Stage 2 of Example 3 starting from 200 mg of the product obtained in Stage 1 of Example 3 and 4 ml of butanol and using 158 mg of ethyl 4-amino-benzoate in place of the benzylamine. Agitation is carried out at ambient temperature then the reaction medium is taken to a temperature of 80 to 85° C. for 22 hours, left to return to ambient temperature, diluted with 4 ml of isopropanol, left for two days at a temperature of approximately 0° C., followed by separating, washing with 10 ml of isopropanol and drying at a temperature of approximately 50° C. After purification on silica eluting with methylene chloride/ethyl acetate in a proportion of 90/10, 209 mg of expected product is obtained in the form of white crystals.

Stage 2: dihydrochloride of ethyl trans-4-[[2-[(4-aminocyclohexyl)-amino]-9-(1-ethylpropyl)-9H-purin-6-yl-]-amino]-benzoate The operation is carried out as in Stage 3 of Example 3 starting from 198 mg of the product obtained in Stage 1 above and 582 mg of trans-1,4-diaminocyclohexane and the reaction medium is taken to a temperature of 140 to 150° C. for 4 hours then cooled down to 70–80° C., diluted with 20 ml of water/ethyl acetate in a proportion of 50/50 and left to settle, followed by washing with 10 ml of water and 5 ml of an aqueous solution of sodium chloride, drying and evaporating to dryness. After purification on silica eluting with methanol/ammonium hydroxide ($NH_4OH$) in a proportion of 98/2 and salification with 1.4 N hydrochloric acid in ethanol, 184 mg of expected product is obtained in the form of crystals.

| NMR in DMSO | |
|---|---|
| 0.80(t) 6H | C$\underline{H}$3—CH2—CH |
| 2.00(q) 4H | CH3—C$\underline{H}$2—CH |
| 1.39(m) 2H<br>1.53(m) 2H | } the axial H's of the cyclohexyl |
| 2.09(m) 4H | the equatorial H's of the cyclohexyl |
| 3.03(bs) 1H | axial $H_4$ |
| 3.69(btt) 1H | axial $H_1$ |
| 4.32(m) | N—C$\underline{H}$—(CH$_2$)$_2$ + O—C$\underline{H}_2$—CH$_3$ |
| 1.34(t) 3H | O—CH$_2$—C$\underline{H}_3$ |
| 7.96 2H<br>8.15 2H | } AA'BB' =C—NH-phenyl-CO$_2$ |
| 8.08 | NH$_2$ + N=C$\underline{H}$—N |
| 9.00 to 10.86 | assumed mobile H's |

EXAMPLE 44 trans(.+−.)-N2-(4-aminocyclo-hexyl)-N6-[(3-iodophenyl)-methyl]-9-(1-methylpropyl)-9H-purin-2,6-diamine dihydrochloride

Stage 1: (.+−.)-2-chloro-N-[(3-iodophenyl)-methyl]-9-(1-methylpropyl)-9H-purin-6-amine The operation is carried out as in Stage 2 of Example 9 starting from 200 mg of the product obtained in Stage 1 of Example 9 and 4 ml of butanol and using 0.128 ml of 3-iodo-benzenemethanamine in place of the benzylamine. The reaction medium is taken to a temperature of 80 to 85° C. for approximately 22 hours, left to return to ambient temperature, diluted with 4 ml of isopropanol and placed for two days at a temperature of approximately 0° C., followed by separating, washing with 10 ml of isopropanol and drying at a temperature of approximately 50° C. After purification on silica eluting with methylene chloride/ethyl acetate in a proportion of 90/10, 290 mg of expected product is obtained in the form of white crystals.

Stage 2: trans(.+−.)-N2-(4-aminocyclo-hexyl)-N6-[(3-iodophenyl)-methyl]-9-(1-methylpropyl)-9H-purin-2,6-diamine dihydrochloride The operation is carried out as in Stage 3 of Example 9 starting from 279 mg of the product obtained in Stage 1 above and 720 mg of trans-1,4-diaminocyclohexane. After purification under the same conditions as for Example 9, salification is carried out with 10 ml 1.4N HCl/Ethanol followed by evaporating to dryness. In this way 232 mg of expected product is obtained in the form of crystals.

| NMR in DMSO | |
|---|---|
| 0.80(t) 3H | C$\underline{H}_3$—CH$_2$— |
| 1.78 to 2.00 2H | CH$_3$—C$\underline{H}_2$ |
| 1.27 to 1.58(m) 4H | the axial H's of the cyclohexyl |
| 1.52(d) 3H | C$\underline{H}_3$—CH |
| 2.03(m) 4H | the equatorial H's of the cyclohexyl |
| 3.03(bs) 1H | axial $H_4$ |
| 3.69(bt) 1H | axial $H_1$ |
| 4.49(m) 1H | N—C$\underline{H}$—CH$_3$ |
| 4.78(bs) 2H | NH—C$\underline{H}_2$-phenyl |
| 7.16(t) | $H_5$ |
| 7.46(bd) 1H | |
| 7.64(dt) 1H | $H_4$, $H_6$ |
| 7.80(bs) 1H | $H_2$ |
| 8.06(bs) <3H | NH$_2$ + N=C$\underline{H}$—N |
| 8.41 to 9.42 | assumed mobile H's |

EXAMPLE 45 trans-N-(4-aminocyclohexyl)-2-[[[2-[[2-[(4-aminocyclohexyl)-amino]-9-cyclopentyl-9H-purin-6-yl]-amino]-ethyl]-amino]-sulphonyl]-benzamide trihydrochloride

Stage 1: ethyl 2[[[2-[(2-chloro-9-cyclopentyl-9H-purin-6-yl)-amino]-ethyl]-amino]-sulphonyl]-benzoate The operation is carried out as in Stage 1 of Example 10 starting from 280 mg of the product obtained in Stage 1 of Example 7, 4 ml of methylene chloride, 0.2 ml of triethylamine and 400 mg of methyl 2-(chlorosulphonyl)benzoate in place of 4-methyl-benzenesulphonic acid chloride then the reaction medium is agitated at ambient temperature for approximately 30 minutes. Then 5 ml of water is added, followed by extracting with 2×10 ml of methylene chloride, washing with 5 ml of $H_2O$, drying and evaporating. After chromatography on silica eluting with methylene chloride/ethyl acetate in a proportion of 70/30, 129 mg of expected product is thus obtained.

Stage 2: trans-N-(4-aminocyclohexyl)-2-[[[2-[[2-[(4-aminocyclohexyl)-amino]-9-cyclopentyl-9H-purin-6-yl]-amino]-ethyl]-amino]-sulphonyl]-benzamide trihydrochloride The operation is carried out as in Stage 2 of Example 10 starting from 111 mg of the product obtained in Stage 1 above and 262 mg of trans-1,4-diaminocyclohexane and the reaction medium is heated to approximately 140° C. for approximately 3 hours then returned to 80° C., 5 ml of AcOEt then 10 ml of warm water are added, followed by leaving to return to ambient temperature, extracting with 2×10 ml of ethyl acetate, washing with 10 ml of saturated aqueous solution of sodium chloride then drying. After purification by chromatography on silica eluting with methylene chloride/methanol/ammonium hydroxide in a proportion of 80/20/2.5, 5 ml of 1.4N hydrochloric acid/ethanol is added, the reaction medium is left to crystallize followed by filtering, rinsing with ml of ether and drying under vacuum. In this way 58 mg of expected product is obtained in the form of a beige solid.

| NMR in DMSO | |
|---|---|
| 1.29 to 1.62 8H | the axial H's of the cyclohexyl |
| 1.71(m) 2H | |
| 1.90(m) 2H | the CH2's of the cyclopentyl |
| 2.07(masked) | |
| 2.18(m) 2H | |
| 2.07(m) 8H | the equatorial H's of the cyclohexyl |
| 3.02(bs) >2H in excess | the axial $H_4$—$H_4$"s |
| 3.18(m) 2H | the $CH_2$—NH's |
| 3.11(masked) | |
| 3.71(masked) 3H | the assumed axial $H_1$—$H_1$"s |
| 4.76(m) 1H | CH of the cyclopentyl |

| NMR in DMSO — continued | |
|---|---|
| 7.42(dd) 1H | |
| 7.58(m) 2H | aromatic H's |
| 7.84(dd) 1H | |
| 8.17 | the $NH_2$ + N=CH—N |
| 7.02 | |
| 8.23 | |
| 8.37 | assumed mobile H's |
| 8.83 | |

EXAMPLE 46 trans-N-(2-[[2-[(4-aminocyclo-hexyl)-amino]-9-cyclopentyl-9H-purin-6-yl]-amino]-ethyl]-trifluoromethanesulphonamide dihydrochloride

Stage 1: N-[2-[(2-chloro-9-cyclopentyl-9H-purin-6-yl)-amino]-ethyl]-trifluoromethanesulphonamide The operation is carried out as in Stage 1 of Example 10 starting from 280 mg of the product obtained in Stage 1 of Example 7, 3 ml of methylene chloride, 0.17 ml of triethylamine, 0.128 ml of trifluoromethanesulphonic acid chloride in place of the 4-methyl-benzenesulphonic acid chloride then the reaction medium is agitated at ambient temperature for approximately 30 min. Then 2 ml of water is added, followed by extracting with 3×5 ml of methylene chloride, washing with 5 ml of saturated sodium chloride, drying, evaporating, impasting in 5 ml of ether then in 5 ml of pentane, separating and drying. In this way 315 mg of expected product is obtained in the form of a beige solid.

Stage 2: trans-N-(2-[[2-[(4-aminocyclo-hexyl)-amino]-9-cyclopentyl-9H-purin-6-yl]-amino]-ethyl]-trifluoromethanesulphonamide dihydrochloride The operation is carried out as in Stage 2 of Example 10 starting from 292 mg of the product obtained in Stage 1 above and 810 mg of trans-1,4-diaminocyclohexane and the reaction medium is heated to approximately 140° C. for approximately 3 hours then returned to 80° C., 5 ml of AtOEt then 10 ml of warm water are added, followed by leaving to return to ambient temperature, extracting with 2×10 ml of ethyl acetate, washing with 10 ml of saturated sodium chloride and drying. After purification by chromatography on silica eluting with methylene chloride/methanol/ammonium hydroxide in a proportion of 85/15/1.5, 5 ml of 1.4N hydrochloric acid/ethanol is added, the reaction medium is left to crystallize followed by filtering, rinsing with 5 ml of ether and drying under vacuum. In this way 167 mg of expected product is obtained in the form of white solid.

| NMR in DMSO | |
|---|---|
| 1.38(m) 2H | the axial H's of the cyclohexyl |
| 1.52(m) 2H | |
| 1.70(m) 2H | |

-continued

| NMR in DMSO | |
|---|---|
| 1.90(m) 2H <br> 2.03 masked(m) <br> 2.18(m) 2H | the CH2's of the cyclopentyl |
| 2.07(m) 4H | the equatorial H's of the cyclohexyl |
| 3.05(bs) 1H | axial H$_4$ |
| 3.46(bt) 2H | CH$_2$—NH—SO$_2$ |
| 3.74(bt) | axial H$_1$ |
| 3.79(masked) | CH$_2$—NH—C=N |
| 4.77(m) 1H | CH of the cyclopentyl |
| 8.02 <3H | the NH$_2$ + N=CH—N |
| 8.31 <br> 8.93 <br> 9.47 | assumed mobile H's |

EXAMPLE 47 trans-4-[(4-aminocyclohexyl)-amino]-N-[2-[[2-[(4-aminocyclohexyl)amino]-9-cyclopentyl-9H-purin-6-yl]-amino]-ethyl]-benzenesulphonamide trihydrochloride Stage 1: N-[2-[(2-chloro-9-cyclopentyl-9H-purin-6-yl)-amino]-ethyl]-4-fluoro-benzenesulphonamide The operation is carried out as in Stage 1 of Example 10 starting from 280 mg of the product obtained in Stage 1 of Example 7, 3 ml of methylene chloride, 0.17 ml of triethylamine and 0.128 ml of 4-fluorobenzenesulphonic acid chloride in place of the 4-methyl-benzenesulphonic acid chloride then the reaction medium is agitated at ambient temperature for approximately 30 min. Then 2 ml of water is added, followed by extracting with 3×5 ml of methylene chloride, washing with 5 ml of saturated sodium chloride, drying, evaporating, impasting in 5 ml of ether then in 5 ml of pentane, separating and drying. In this way 360 mg of expected product is obtained.

Stage 2: trans-4-[(4-aminocyclohexyl)-amino]-N-[2-[[2-[(4-aminocyclohexyl)amino]-9-cyclopentyl-9H-purin-6-yl]-amino]ethyl]-benzenesulphonamide trihydrochloride The operation is carried out as in Stage 2 of Example 10 starting from 173 mg of the product obtained in Stage 1 above and 450 mg of trans-1,4-diaminocyclohexane and the reaction medium is heated to approximately 140° C. for approximately 3 hours then left to return to 80° C., 5 ml of AcOEt then 5 ml of warm water are added, the reaction medium is left to return to ambient temperature, followed by extracting with 2×10 ml of ethyl acetate, washing with 10 ml of saturated sodium chloride then drying. After purification by chromatography on silica eluting with methylene chloride/methanol/ammonium hydroxide in a proportion of 75/22/03, 5 ml of 1.4N hydrochloric acid/ethanol is added, the reaction medium is left to crystallize followed by filtering, rinsing with 5 ml of ether and drying under vacuum. In this way 62 mg of expected product is obtained in the form of white crystals.

| NMR in DMSO | |
|---|---|
| 1.15 to 1.61(m) 8H | the axial H's of the cyclohexyl |
| 1.69(m) 2H <br> 1.88(m) 2H <br> 2.03 masked(m) <br> 2.17(m) 2H | the CH2's of the cyclopentyl |
| 2.03(m) 8H | the equatorial H's of the cyclohexyl |
| 2.99(m) 4H | 1 CH$_2$—CH$_2$—NH + H$_4$—H$_4$' assumed axial |
| 3.22(bt) 1H | axial H$_1$' |
| 3.70(m) 3H | 1 CH$_2$—CH$_2$—NH + assumed axial H$_1$ |
| 4.75(m) 1H | CH of the cyclopentyl |
| 6.63 2H <br> 7.45 2H AA'BB' | SO$_2$-phenyl-NH |
| 8.15(s) in excess | the NH$_2$ + N=CH—N |
| 7.18 <br> 8.31 <br> 8.37 <br> 8.96 | assumed mobile H's |

EXAMPLE 48 trans-N-(2-[[2-[[4-aminocyclo-hexyl)-amino]-9-cyclopentyl-9H-purin-6-yl]-amino]-ethyl]-4-(trifluoromethyl)-benzenesulphonamide dihydrochloride Stage 1: N-[2-[(2-chloro-9-cyclopentyl-9H-purin-6-yl)-amino]-ethyl]-4-(trifluoromethyl)-benzenesulphonamide The operation is carried out as in Stage 1 of Example 10 starting from 280 mg of the product obtained in Stage 1 of Example 7, 3 ml of methylene chloride, 0.17 ml of triethylamine and 280 mg of 4-(trifluoromethyl)benzenesulphonic acid chloride in place of the 4-methyl-benzenesulphonic acid chloride, then the reaction medium is agitated at ambient temperature for approximately 30 min. Then 2 ml of water is added, followed by extracting with 3×5 ml of methylene chloride, washing with 5 ml of saturated sodium chloride, drying, evaporating, impasting in 5 ml of ether then in 5 ml of pentane, separating, and drying. In this way 375 mg of expected product is obtained.

Stage 2 trans-N-(2-[[2-[[4-aminocyclo-hexyl)-amino]-9-cyclopentyl-9H-purin-6-yl]-amino]-ethyl]-4-(trifluoromethyl)-benzenesulphonamide dihydrochloride The operation is carried out as in Stage 2 of Example 10 starting from 188 mg of the product obtained in Stage 1 above and 440 mg of trans-1,4-diaminocyclohexane and the reaction medium is heated to approximately 140° C. for approximately 3 hours, left to return to 80° C., 5 ml of AcOEt then 5 ml of warm water are added, the reaction medium is left to return to ambient temperature, followed by extracting with 2×5 ml of ethyl acetate, washing with 5 ml of saturated sodium chloride, then drying. After purification by chromatography on silica eluting with methylene chloride/methanol/ammonium hydroxide in a proportion of 90/10/1, 5 ml of 1.4N hydrochloric acid/ethanol is added, the reaction medium is left to crystallize, followed by filtering, rinsing with 5 ml of ether and drying under vacuum. In this way 148 mg of expected product is obtained in the form of white crystals.

| NMR in DMSO | |
|---|---|
| 1.36(m) 2H | } the axial H's of the cyclohexyl |
| 1.51(m) 2H | |
| 1.70(m) 2H | } the CH2's of the cyclopentyl |
| 1.88(m) 2H | |
| 2.04 masked(m) | |
| 2.16(m) 2H | |
| 2.06 | the equatorial H's of the cyclohexyl |
| 3.05(bs) | H$_4$ axial |
| 3.15 2H | } HN—CH$_2$—CH$_2$—NH + H$_1$ assumed axial |
| 3.69 3H | |
| 4.75(m) 1H | CH of the cyclopentyl |
| 7.88 2H | |
| 8.00 2H AA'BB' | F$_3$C-phenyl-SO$_2$ |
| 8.10 3H | the NH$_2$ + N=C$\underline{H}$—N |
| 8.30 | } assumed mobile H's |
| 8.92 | |

EXAMPLE 49 trans(.+−.)-N2-(4-aminocyclo-hexyl)-9-(1-methyl-propyl)-N6-propyl-9H-purin-2,6-diamine dihydrochloride Stage 1: (.+−.)-2-chloro-9-(1-methylpropyl)N-propyl-9H-purin-6-amine The operation is carried out as in Stage 2 of Example 9 starting from 200 mg of the product obtained in Stage 1 of Example 9 and 4 ml of butanol and using 0.132 ml 1-propanamine in place of the benzylamine. Agitation is carried out at ambient temperature then the reaction medium is taken to a temperature of 80 to 85° C. for approximately 22 hours, left to return to ambient temperature, followed by taking up in 5 ml of ethyl acetate, evaporating to dryness, impasting in 5 ml of pentane at ambient temperature, separating, washing with 5 ml of pentane and drying at a temperature of approximately 50° C.

After purification on silica eluting with methylene chloride/ethyl acetate in a proportion of 90/10, 203 mg of expected product is obtained in the form of white crystals.

Stage 2: trans(.+−.)-N2-(4-aminocyclo-hexyl)-9-(1-methylpropyl)-N6-propyl-9H-purin-2,6-diamine dihydrochloride The operation is carried out as in Stage 2 of Example 44 starting from 117 mg of the product obtained in Stage 1 above and 500 mg of trans-1,4-diaminocyclohexane. In this way 80 mg of expected product is obtained in the form of crystals.

| NMR in DMSO | |
|---|---|
| 0.81(t) 3H | C$\underline{H}_3$—CH$_2$—CH |
| 0.96(t) 3H | C$\underline{H}_3$—CH$_2$—CH$_2$ |
| 1.38 to 1.47 4H | the axial H's of the cyclohexyl |
| 1.52(d) 2H | C$\underline{H}_3$—CH |
| 1.66(m) 2H | CH$_3$—C$\underline{H}_2$—CH$_2$ |
| 1.96(m) 2H | CH$_3$—C$\underline{H}_2$—CH |
| 2.08(m) 4H | the equatorial H's of the cyclohexyl |
| 3.04(bs) 1H | axial H$_4$ |
| 3.63(bs) 2H | HN—C$\underline{H}_2$— (chain) |
| 3.72(bt) 1H | axial H$_1$ |
| 4.43(m) 1H | N—C$\underline{H}$— |
| 8.11(bs) <3H | NH$_2$ + N=C$\underline{H}$—N |
| 8.25 to 9.12 | assumed mobile H's |

EXAMPLE 50 trans(.+−.)-N2-(4-aminocyclo-hexyl))-9-(1-methyl-propyl)-N6-[4-(trifluoromethoxy)-phenyl]-9H-purin-2,6-diamine dihydrochloride Stage 1: (.+−.)-2-chloro-9-(1-methylpropyl)-N-[4-(trifluoromethoxy)-phenyl]-9H-purin-6-amine The operation is carried out as in Stage 2 of Example 9 starting from 200 mg of the product obtained in Stage 1 of Example 9 and 4 ml of butanol and using 0.135 ml of 4-(trifluoromethoxy)-benzenamine in place of the benzylamine. Agitation is carried out at ambient temperature then the reaction medium is taken to a temperature of 80 to 85° C. for approximately 22 hours, left to return to ambient temperature, diluted with 4 ml of isopropanol and placed for two days at a temperature of approximately 0° C., followed by separating, washing with 5 ml of isopropanol and drying at a temperature of approximately 50° C. After purification on silica eluting with methylene chloride/ethyl acetate in a proportion of 90/10, 210 mg of expected product is obtained in the form of white crystals.

Stage 2: trans(.+−.)-N2-(4-aminocyclo-hexyl)-9-(1-methylpropyl)-N6-[4-(trifluoromethoxy)-phenyl]-9H-purin-2,6-diamine dihydrochloride The operation is carried out as in Stage 2 of Example 44 starting from 201 mg of the product obtained in Stage 1 above and 595 mg of trans-1,4-diaminocyclohexane. In this way 139 mg of expected product is obtained in the form of crystals.

| NMR in DMSO | |
|---|---|
| 0.84(t) 3H | C$\underline{H}_3$—CH$_2$ |
| 1.83 to 2.02(m) 2H | CH$_3$—C$\underline{H}_2$ |
| 1.38 to 1.53 4H | the axial H's of the cyclohexyl |
| 1.57(d) 3H | C$\underline{H}_3$—CH |
| 2.05(m) 4H | the equatorial H's of the cyclohexyl |
| 3.02(bs) 1H | axial H$_4$ |
| 3.69(bt) 1H | axial H$_1$ |
| 4.54(m) 1H | N—C$\underline{H}$—CH$_2$— |
| 7.36 | |
| 8.08 2H | } AA'BB' O-phenyl-NH |
| 8.10(masked) | } NH$_2$ + N=C$\underline{H}$—N |
| 8.94 | } assumed mobile H's |
| 10.74 | |

EXAMPLE 51 dihydrochloride of ethyl trans(+−)-4-[[2-[[4-aminocyclo-hexyl]-amino]-9-(1-methylpropyl)-9H-purin-6-yl]amino]-benzoate Stage 1: ethyl (.+−.)-4-[[2-chloro-9-(1-methylpropyl)-9H-purin-6-yl]-amino]-benzoate The operation is carried out as in Stage 2 of Example 9 starting from 200 mg of the product obtained in Stage 1 of Example 9 and 4 ml of butanol and using 0.165 mg of ethyl 4-amino-benzoate in place of the benzylamine. Agitation is carried out at ambient temperature then the reaction medium is taken to a temperature of 80 to 85° C. for approximately 22 hours, left to return to ambient temperature, diluted with 4 ml of isopropanol and placed for two days at a temperature of approximately 0° C., followed by separating, washing with 5 ml of isopropanol and drying at a temperature of approximately 50° C. After purification on silica eluting with methylene chloride/ethyl acetate in a proportion of 90/10, 289 mg of expected product is obtained in the form of white crystals.

Stage 2: dihydrochloride of ethyl trans(+−)-4-[[2-[[4-aminocyclo-hexyl]-amino]-9-(1-methylpropyl)-9H-purin-6-yl]-amino]-benzoate The operation is carried out as in Stage 2 of Example 44 starting from 275 mg of the product obtained in Stage 1 above and 840 mg of trans-1,4-diaminocyclohexane. In this way 267 mg of expected product is obtained in the form of crystals.

| NMR in DMSO | |
|---|---|
| 0.84(t) 3H | C$\underline{H_3}$—CH$_2$ |
| 1.85 to 2.04(m) 2H | CH$_3$—C$\underline{H_2}$ |
| 1.34(t) 3H | C$\underline{H_3}$—CH$_2$—O |
| 4.32(q) 2H | CH$_3$—C$\underline{H_2}$—O |
| 1.37 to 1.53 4H | the axial H's of the cyclohexyl |
| 1.57(d) 3H | C$\underline{H_3}$—CH |
| 2.09(m) 4H | the equatorial H's of the cyclohexyl |
| 3.03(bs) 1H | axial H$_4$ |
| 3.71(bt) 1H | axial H$_1$ |
| 4.56(m) 1H | N—C$\underline{H}$—CH$_2$— |
| 7.96 2H | |
| 8.15 2H AA'BB' | NH-phenyl-C=O |
| 8.10(bs) <3H | NH$_2$ + N=C$\underline{H}$—N |
| 9.08 | assumed mobile H's |
| 10.93 | |

EXAMPLE 52 trans(.+−.)-N2-(4-aminocyclo-hexyl)-9-(1-methyl-propyl)-N6-phenyl-9H-purin-2,6-diamine dihydrochloride Stage 1: (.+−.)-2-chloro-9-(1-methylpropyl)-N-phenyl-9H-purin-6-amine.

The operation is carried out as in Stage 2 of Example 9 starting from 200 mg of the product obtained in Stage 1 of Example 9 and 4 ml of butanol and using 0.091 ml of aniline in place of the benzylamine. Agitation is carried out at ambient temperature then the reaction medium is taken to a temperature of 80 to 85° C. for approximately 22 hours, left to return to ambient temperature, diluted with 4 ml of isopropanol and placed for two days at a temperature of approximately 0° C., followed by separating, washing with 5 ml of isopropanol and drying at a temperature of approximately 80° C. After purification on silica eluting with methylene chloride/ethyl acetate in a proportion of 90/10, 176 mg of expected product is obtained in the form of white crystals.

Stage 2: trans(.+−.)-N2-(4-aminocyclo-hexyl)-9-(1-methylpropyl)-N6-phenyl-9H-purin-2,6-diamine dihydrochloride The operation is carried out as in Stage 2 of Example 44 starting from 166 mg of the product obtained in Stage 1 above and 629 mg of trans-1,4-diaminocyclohexane. In this way 158 mg of expected product is obtained in the form of crystals.

| NMR in DMSO | |
|---|---|
| 0.84(t) 3H | C$\underline{H_3}$—CH$_2$ |
| 1.83 to 2.10(m) 2H | CH$_3$—C$\underline{H_2}$ |
| 1.29 to 1.61 4H | the axial H's of the cyclohexyl |
| 1.57(d) 3H | C$\underline{H_3}$—CH |
| 2.08(m) 4H | the equatorial H's of the cyclohexyl |
| 3.02(bs) 1H | axial H$_4$ |
| 3.70(bt) 1H | axial H$_1$ |
| 4.55(m) 1H | —C$\underline{H}$—CH$_2$— |
| 7.12(t) 1H | |
| 7.40(t) 2H | aromatic H |
| 7.94(d) 2H | |
| 8.10(bs) <3H | NH$_2$ + N=C$\underline{H}$—N |
| 9.01 | assumed mobile H's |
| 10.66 | |

EXAMPLE 53 trans-N-[2-[[2-[(4-aminocyclo-hexyl)-amino]-9-cyclopentyl-9H-purin-6-yl]-amino]-ethyl]-4-methoxy-benzenesulphonamide dihydrochloride Stage 1: N-[2-[(2-chloro-9-cyclopentyl-9H-purin-6-yl)-amino]-ethyl]-4-methoxy-benzenesulphonamide The operation is carried out as in Stage 1 of Example 10 starting from 280 mg of the product obtained in Stage 1 of Example 7, 4 ml of methylene chloride, 0.2 ml of triethylamine and 248 mg of 4-methoxy-benzenesulphonic acid chloride in place of the 4-methyl-benzenesulphonic acid chloride then agitation is carried out at ambient temperature for approximately one night. Then 2 ml of water is added, followed by extracting with 3×5 ml of methylene chloride, washing with 5 ml of saturated sodium chloride, drying, evaporating, impasting in 5 ml of ether then in 5 ml of pentane, separating, and drying. After chromatography on silica eluting with methylene chloride/CH$_3$CN in a proportion of 70/30, 250 mg of expected product is thus obtained in the form of a beige solid.

Stage 2: trans-N-[2-[[2-[(4-aminocyclo-hexyl)-amino]-9-cyclopentyl-9H-purin-6-yl]-amino]-ethyl]-4-methoxy-benzenesulphonamide dihydrochloride The operation is carried out as in Stage 2 of Example 10 starting from 126 mg of the product obtained in Stage 1 above and 319 mg of trans-1,4-diaminocyclohexane and the reaction medium is heated to approximately 140° C. for approximately 3 hours, left to return to 80° C., 5 ml of AcOEt is added, 5 ml of warm water is added, the reaction medium is left to return to ambient temperature, followed by extracting with 2×5 ml of ethyl acetate, washing with 5 ml of saturated sodium chloride, then drying. After purification by chromatography on silica eluting with methylene chloride/methanol/ammonium hydroxide in a proportion of 85/15/1.5, 5 ml of 1.4N hydrochloric acid/ethanol is added, the reaction medium is left to crystallize, followed by filtering, rinsing with 5 ml of ether and drying under vacuum. In this way 95 mg of expected product is obtained in the form of a beige solid.

| NMR in DMSO | |
|---|---|
| 1.39(m) 2H<br>1.53(m) 2H | the axial H's of the cyclohexyl |
| 2.05 | the equatorial H's of the cyclohexyl |
| 1.71 and 1.90 | C$\underline{H}_2$—CH$_2$—CH—N |
| 2.00 and 2.17 | CH$_2$—C$\underline{H}_2$—CH—N |
| 4.75 | CH$_2$—CH$_2$—C$\underline{H}$—N |
| 3.03(masked) | axial H$_4$ |
| 3.71(masked) | axial H$_1$ |
| 3.09(t)<br>3.71(m) | N—CH$_2$—CH$_2$—N |
| 3.82(s) | phenyl-O-methyl |
| 7.00<br>7.70 | phenyl-O-methyl |
| 7.47<br>8.04<br>8.24<br>8.73 | assumed mobile H's and CH=N |

EXAMPLE 54 trans-N-[2-[[2-[(4-aminocyclo-hexyl)-amino]-9-cyclopentyl-9H-purin-6-yl]-amino]-ethyl]-4-chloro-benzenesulphonamide dihydrochloride Stage 1: 4-chloro-N-[2-[(2-chloro-9-cyclopentyl-9H-purin-6-yl)-amino]-ethyl]-benzenesulphonamide The operation is carried out as in Stage 1 of Example 10 starting from 280 mg of the product obtained in Stage 1 of Example 7, 4 ml of methylene chloride, 0.2 ml of triethylamine and 255 mg of 4-chlorobenzenesulphonic acid chloride in place of the 4-methyl-benzenesulphonic acid chloride then the reaction medium is agitated at ambient temperature for 30 minutes. Then 2 ml of water is added, followed by extracting with 3×5 ml of methylene chloride, washing with 5 ml of saturated sodium chloride, drying, evaporating, impasting in 5 ml of ether then in 5 ml of pentane, separating, and drying. After chromatography on silica eluting with methylene chloride/CH$_3$CN in a proportion of 70/30, 350 mg of expected product is obtained in the form of a beige solid.

Stage 2: trans-N-[2-[[2-[(4-aminocyclo-hexyl)-amino]-9-cyclopentyl-9H-purin-6-yl]-amino]-ethyl]-4-chloro benzenesulphonamide dihydrochloride.

The operation is carried out as in Stage 2 of Example 10 starting from 161 mg of the product obtained in Stage 1 above and 403 mg of trans-1,4-diaminocyclohexane and the reaction medium is heated to approximately 140° C. for approximately 3 hours 30 minutes left to return to 80° C., 5 ml of AcOEt then 5 ml of warm water are added, the reaction medium is left to return to ambient temperature, followed by extracting with 2×5 ml of ethyl acetate, washing with 5 ml of saturated sodium chloride, then drying. After purification by chromatography on silica eluting with methylene chloride/methanol/ammonium hydroxide in a proportion of 85/15/1.5, 5 ml of 1.4N hydrochloric acid/ethanol is added, the reaction medium is left to crystallize, followed by filtering, rinsing with 5 ml of ether and drying under vacuum. In this way 113 mg of expected product is obtained in the form of beige white crystals.

| NMR in DMSO | |
|---|---|
| 1.37(m) 2H<br>1.57(m) 2H | the axial H's of the cyclohexyl |
| 2.04 | the equatorial H's of the cyclohexyl |
| 1.70 and 1.89 | C$\underline{H}_2$—CH$_2$—CH—N |
| 2.00 and 2.17 | CH$_2$—C$\underline{H}_2$—CH—N |
| 4.75 | CH$_2$—CH$_2$—C$\underline{H}$—N |
| 3.05(masked) | axial H$_4$ |
| 3.70(masked) | axial H$_1$ |
| 3.13(q)<br>3.70(bt) | N—CH$_2$—CH$_2$—N |
| 7.84(t) | NH—CH$_2$ |
| 7.53<br>7.76(s) | phenyl-SO$_2$ |
| 8.07<br>8.28<br>8.85 | assumed mobile H's and CH=N |

EXAMPLE 55 trans-N-[2-[2-[(4-aminocyclo-hexyl)-amino]-9-cyclopentyl-9H-purin-6-yl]-amino]-ethyl]-1-methyl-ethanesulphonamide dihydrochloride Stage 1: N-[2-[(2-chloro-9-cyclopentyl-9H-purin-6-yl)-amino]-ethyl]-1-methyl-ethanesulphonamide.

The operation is carried out as in Stage 1 of Example 10 starting from 280 mg of the product obtained in Stage 1 of Example 7, 4 ml of methylene chloride, 0.2 ml of triethylamine and 172 mg of 1-methylethanesulphonic acid chloride in place of the 4-methyl-benzenesulphonic acid chloride then the reaction medium is agitated at ambient temperature for approximately 30 min. Then 2 ml of water is added, followed by extracting with 3×5 ml of methylene chloride, washing with 5 ml of saturated sodium chloride, drying, evaporating, impasting in 5 ml of ether then in 5 ml of pentane, separating, and drying. After chromatography on silica eluting with methylene chloride/CH$_3$CN in a proportion of 70/30, 115 mg of expected product is thus obtained in the form of white crystals.

Stage 2: trans-N-[2-[2-[(4-aminocyclo-hexyl)-amino]-9-cyclopentyl-9H-purin-6-yl]-amino]-ethyl]-1-methyl-ethanesulphonamide dihydrochloride The operation is carried out as in Stage 2 of Example 10 starting from 157 mg of the product obtained in Stage 1 above and 315 mg of trans-1,4-diaminocyclohexane and the reaction medium is heated to approximately 140° C. for approximately 3 hours 30 minutes returned to 80° C., 5 ml of AcOEt and 5 ml of warm water are added, the reaction medium is left to return to ambient temperature, followed by extracting with 2×5 ml of ethyl acetate, washing with 5 ml of saturated sodium chloride, then drying. After purification by chromatography on silica eluting with methylene chloride/methanol/ammonium hydroxide in a proportion of 85/15/1.5, 5 ml of 1.4 N hydrochloric acid in ethanol is added, the reaction medium is left to crystallize, followed by filtering, rinsing with 5 ml of ether and drying under vacuum. In this way 98 mg of expected product is obtained in the form of white crystals.

| NMR in DMSO | |
|---|---|
| 1.23(d) | C$\underline{H}_3$—CH—C$\underline{H}_3$ |
| 3.19(m) | CH$_3$—C$\underline{H}$—CH$_3$ |
| 1.39(m) 2H <br> 1.53(m) 2H | the axial H's of the cyclohexyl |
| 2.06 | the equatorial H's of the cyclohexyl and the CH2's of the cyclohexyl |
| 1.71 and 1.90 | C$\underline{H}_2$—CH$_2$—CH—N |
| 2.00 and 2.17 | CH$_2$—C$\underline{H}_2$—CH—N |
| 4.76(m) | CH$_2$—CH$_2$—C$\underline{H}$—N |
| 3.05(masked) | axial H$_4$ |
| 3.73(masked) | axial H$_1$ |
| 3.29(t) <br> 3.76(m) | N—CH$_2$—CH$_2$—N |
| 6.94 | one of the N$\underline{H}$—CH$_2$'s |
| 8.04 <br> 8.25 <br> 8.85 | assumed mobile H's and CH=N |

EXAMPLE 56 dihydrochloride of ethyl trans-2-[([[2-[2-[(4-amino-cyclohexyl)-amino]-9-cyclopentyl-9H-purin-6-yl]-amino]-ethyl]-amino]-sulphonyl]-benzoate The operation is carried out as in Stage 1 of Example 45 using ethyl O-chlorosulphonyl-benzoate in place of methyl 2-(chlorosulphonyl)-benzoate. Starting from the product obtained in this way, the operation is carried out as in Stage 2 of Example 45 and the expected product is thus obtained.

EXAMPLE 57 trans-N-[±2-[(4-aminocyclo-hexyl)-amino]-9-cyclopentyl-9H-purin-6-yl]-benzamide dihydrochloride The operation is carried out as in Stage 1 of Example 8 using benzamide in place of the benzenesulphonamide. Starting from the product obtained in this way, the operation is carried out as in Stage 2 of Example 8 and the expected product and is thus obtained.

EXAMPLE 58 dihydrochloride of trans-3-[[2-[(4-amino-cyclo-hexyl)-amino]-9-cyclopentyl-9H-purin-6-yl]-amino]-benzoic acid STADE 1: methyl 3-[(2-chloro-9-cyclopentyl-9H-purin-6-yl)amino]-benzoate The operation is carried out as in Stage 1 of Example 6 by introducing, at ambient temperature, 257 mg of the product obtained in Stage 1 of Example 1, 4 ml of butanol and 181 mg of methyl-3-aminobenzoate and the reaction medium is heated at a temperature of approximately 100° C. for approximately 5 hours, followed by evaporating, impasting in ether then drying. In this way 352 mg of expected product is obtained in the form of off-white crystals.

IR spectrum NUJOL

>=O 1722 cm−1

C=C+C=N+aromatic 1648; 1619; 1600; 1582; 1558; 1528; 1500 cm−1

| NMR in DMSO | |
|---|---|
| 1.72 (m) | |
| 1.89 (m) | |
| 2.01 (m) | |
| 2.19 (m) | the cyclic CH$_2$'s of the cyclopentyl |
| 3.88 (s) | —CO$_2$C$\underline{H}_3$ |
| 4.87 (m) 1H | —N—CH (CH of the cyclopentyl) |
| 8.52 (s) 1H | —C$\underline{H}$=N |
| 7.51 (t) | H$_5$ |
| 7.68 (d) | H$_6$ |
| 8.13 (bd) | H$_4$ |
| 8.56 (bs) | H$_2$ |
| 10.58 (s) | NH |

Stage 2: dihydrochloride of trans-3-[[2-[(4-amino-cyclohexyl)-amino]-9-cyclopentyl-9H-purin-6-yl]-amino]benzoic acid The operation is carried out as in Stage 2 of Example 6 and 400 mg of trans-1,4-diaminocyclohexane is taken to a temperature of approximately 150° C. and 260 mg of the product obtained in Stage 1 above is added: the reaction medium is left under agitation for 5 hours then left overnight at ambient temperature. Then 5 ml of water is added, followed by extracting with 40 ml of ethyl acetate, adding 10 ml of methanol, drying, filtering, evaporating to dryness, taking up in 4 ml of 1.4 N HCl in ethanol and 20 ml of methanol, evaporating to dryness, then impasting in 5 ml of ether and drying at a temperature of approximately 60° C. In this way 73 mg of expected product is obtained in the form of a beige solid.

| NMR in DMSO | |
|---|---|
| 1.40 (m) } 1.52 (m) 4H | the axial H's of the cyclohexyl |
| 1.71 (m) 2H 1.91 (m) 2H 2.04 (m) 2H 2.19 (m) 4H } | CH2's of the cyclopentyl |
| 2.04 (m) 4H | equatorial H's of the cyclohexyl |
| 2.98 (bs) 1N | axial $H_4$ |
| 3.77 (bt) 1N | axial $H_1$ |
| 4.82 (m) 1H | CH cyclopentyl |
| 7.50 (t) 1H | $H_4'$ |
| 7.67 (d) 1H | $H_3'$ |
| 8.06 (bs) <3H | $NH_2$ + N=CH—N |
| 8.13 8.26 | $H_1'$, $H_5'$ |
| 8.44–8.83–10.58 | assumed mobile H's |

EXAMPLE 59

Dihydrochloride of ethyl trans-3-[[2-[(4-amino-cyclohexyl)-amino]-9-cyclopentyl-9H-purin-6-yl]amino]-benzoate Stage 1: ethyl 3-[(2-chloro-9-cyclopentyl-9H-purin-6-yl)amino]-benzoate 257 mg of the product obtained in Stage 1 of Example 1, 4 ml of n-butanol and 200 mg of ethyl-3-aminobenzoate are introduced at ambient temperature and the reaction medium is immersed in a bath at a temperature of approximately 100° C. for 6 hours and 30 minutes under agitation then for 16 hours at ambient temperature, left to return to ambient temperature, followed by separating, rinsing with ether then drying under reduced pressure. In this way 364 mg of expected product is obtained.

Stage 2: dihydrochloride of ethyl trans-3-[[2-[(4-aminocyclohexyl)-amino]-9-cyclopentyl-9H-purin-6-yl]amino]-benzoate 400 mg of trans-1,4-diaminocyclohexane is taken to approximately 140° C. then 270 mg of the product obtained in Stage 1 above is added, the reaction medium is left under agitation for 5 hours then left to return to ambient temperature. Then 15 ml of water is added, followed by extracting with dichloromethane, washing with water, drying and evaporating the solvents. The residue is chromatographed on silica eluting with methanol/ammonium hydroxide (98/2), taken up in ethanol, salified using a 1.4N solution of HCl in EtOH, followed by drying the expected hydrochloride at a temperature of approximately 60° C. In this way 156 mg of expected product is obtained.

| NNR in DMSO | |
|---|---|
| 1.35 (t) 3H, 4.35 (q) 2H | $CO_2$—$CH_2$—$CH_3$ |
| 1.43 (m) 4H | axial $CH_2$ of the cyclohexyl |
| 1.71 (m)–1.91 (m)–2.06 (masked)–2.20 (m) | $CH2$'s of the cyclopentyl |
| 2.07 (m) H | equatorial of the cyclohexyl |
| 3.00 (s) 1H, H4' | axial |
| 3.70 (t) 1H, H1' | axial |
| 4.84 (m) 1H | C$\underline{H}$ of the cyclopentyl |
| 7.53 (t) 1H, | $H_5$ |
| 7.68 (dt) 1H, | $H_4$ |
| 8.09 (bs) <3H | N=C$\underline{H}$ + mobile H's |
| 8.32 (t) 1H, | $H_2$ |
| 8.37 (d) 1H, | $H_6$ |
| 8.89–10.71 | mobile H's |

EXAMPLE 60 trans-4-((2-((4-amino-cyclohexyl)amino)-9-cyclopentyl-9H-purin-6-yl)amino)-benzamide dihydrochloride STADE 1: 4-[(2-chloro-9-cyclopentyl-9H-purin-6-yl)amino]-benzamide.

The operation is carried out as in Stage 1 of Example 6 by introducing, at ambient temperature, 193 mg of the product obtained in Stage 1 of Example 1, 2 ml of butanol and 68 mg of 4-aminobenzamide and the reaction medium is agitated at a temperature of approximately 100° C. for approximately 20 hours, followed by evaporating, impasting in ether then drying. In this way 170 mg of expected product is obtained in the form of crystals.

| IR spectrum NUJOL | |
|---|---|
| >=O | 1653 cm−1 |
| conjugated system + aromatic | 1616; 1605; 1555; 1517; 1491 cm−1 |
| NMR in DMSO | |
| 1.73 (m) 2H 1.90 (m) 2H 2.02 (m) 2H 2.19 (m) 2H | the CH2's of the cyclopentyl |
| 4.87 (m) 1H | CH of the cyclopentyl |
| 8.43 (s) 1H | N=C$\underline{H}$—N— |
| 10.33 (s) 1H | |
| 7.22 (bs) | assumed mobile H's |
| 7.86 7.93 } | -phenyl-C= |

Stage 2: trans-4-((2-((4-aminocyclohexyl)-amino)-9-cyclopentyl-9H-purin-6-yl)amino)-benzamide dihydrochloride The operation is carried out as in Stage 2 of Example 6 and 800 mg of trans-1,4-diaminocyclohexane is introduced at ambient temperature under agitation then the reaction medium is heated at approximately 150° C. until melting and 249 mg of the product obtained in Stage 1 above is added, the reaction medium is left under agitation for 4 hours 30 minutes then left to return to ambient temperature. Then 10 ml of water is added, followed by extracting with 10 ml of methylene chloride containing 25% of methanol, drying, filtering, evaporating to dryness and taking up in 5 ml of ethanol. 2 ml of 1.4 N HCl in ethanol is added, followed by evaporating, leaving to crystallize, separating and washing with ethanol then drying at a temperature of approximately 60° C. In this way 207 mg of expected product is obtained in the form of colourless crystals.

| NMR in DMSO | |
|---|---|
| 1.43 | } the axial H's of the CH2's of the cyclohexyl |
| 1.60 | |
| 2.08 | the equatorial H's of the CH2's of the cyclohexyl |
| 1.75 (m) 2H | |
| 1.95 (m) 2H | |
| 2.05 (m) 2H | the CH2's of the cyclopentyl |
| 2.20 (m) 2H | |
| 3.04 (m) | axial $H_4'$ |
| 3.76 (tt) | axial $H_1'$ |
| 4.84 (m) | angular H of the cyclopentyl |
| 7.96 | } -phenyl- |
| 8.06 | |
| 8.10 | mobile H's and $H_2$ |
| 8.88 (s), 10.65 (s), 7.3 | mobile H's |

EXAMPLE 61 trans-3-[[[2-[(4-aminocyclo-hexyl)-amino]-9-cyclo-pentyl-9H-purin-6-yl]amino]methyl]-benzamide dihydrochloride The operation is carried out as in Example 6 using 3 methylaminobenzamide in Stage 1 of Example 6 in place of the ethyl-4-aminobenzoate. Then the operation is carried out as in Stage 2 of Example 6 and in this way the expected product is obtained.

EXAMPLE 62 dihydrochloride of ethyl trans-3-[[[2-[(4-aminocy-clo-hexyl)-amino]-9-cyclopentyl-9H-purin-6-yl]amino]methyl]-benzoate The operation is carried out as in Example 1 using the hydrochloride of methyl 3-(aminomethyl)-benzoate in Stage 2 of Example 1 in place of the hydrochloride of methyl 4-(aminomethyl)-benzoate.

EXAMPLE 63 trans-N-(2-(([4-aminocyclo-hexyl)-amino)-9-cyclo-pentyl-9H-purin-6-yl)-3-pyridine-sulphonamide dihydrochloride Stage 1: N-[[2-chloro-9-cyclopentyl-9H-purin-6-yl]amino]-3-pyridinesulphonamide The operation is carried out as in Stage 1 of Example 8 starting from 514 mg of the product obtained in Stage 1 of Example 1, 8 ml of dimethoxyethane (DME), 780 mg of caesium carbonate ($Cs_2CO_3$) and 316 mg of 3-pyridine-sulphonamide in place of the benzene-sulphonamide and the reaction medium is agitated at a temperature of approximately 100° C. for approximately 5 hours 30 minutes and left overnight at ambient temperature. Then 4 ml of 2N hydrochloric acid is added, followed by separating the precipitate formed, rinsing with 5 ml of water and drying under vacuum at a temperature of approximately 50° C. In this way 414 mg of expected product is obtained in the form of beige crystals.

Stage 2: trans-N-(2-(([4-aminocyclo-hexyl)amino)-9-cyclopentyl-9H-purin-6-yl)-3-pyridine-sulphona-mide dihydrochloride The operation is carried out as in Stage 2 of Example 8 and 400 mg of trans-1,4-diaminocyclohexane is taken to a temperature of approximately 140° C., 265 mg of the product obtained in Stage 1 above is added and the reaction medium is maintained at this temperature for approximately 3 hours 30 minutes. After chromatography on silica eluting with methanol/ammonium hydroxide in a proportion of 98/2, then 4 ml of ethanol and 2 ml of methanol then 4 ml of 1.4N hydrochloric acid/ethanol are added, followed by filtering the slightly insoluble part, evaporating to dryness, impasting in 10 ml of ether and drying under vacuum at a temperature of approximately 60° C. In this way 148 mg of expected product is obtained in the form of brown crystals.

| NMR in DMSO | |
|---|---|
| 1.34 (m) 2H | } the axial H's of the cyclohexyl |
| 1.50 (m) 2H | |
| 1.68 (m) 2H | |
| 1.88 (m) 2H | the CH2's of the cyclopentyl |
| 2.05 (masked) | |
| 2.06 | the equatorial H's of the cyclohexyl |
| 3.03 (bs) 1H | axial $H_4$ |
| 3.59 (bt) 1H | axial $H_1$ |
| 4.72 (m) 1H | CH of the cyclopentyl |
| 7.62 (dd) | $H_5'$ |
| 8.33 (dt) 1H | $H_4'$ |
| 8.77 (dd) 1H | $H_6'$ |
| 9.12 (d) | $H_2'$ |
| 8.13 (bs) <3H | N=CH—N + $NH_2$ |
| 8.22 (s) 1H | assumed mobile H |

EXAMPLE 64 dihydrochloride of ethyl trans-4-[[2-[(4-aminocyclo-hexyl)amino]-9-cyclopentyl-9H-purin-6-yl]amino]-butanoate The operation is carried out as in Example 1 using ethyl ∝ aminobutyrate in Stage 2 of Example 1 in place of the hydrochloride of methyl-4-(aminomethyl)-benzoate, the operation is then carried out as in Stage 3 of Example 1 from the product obtained in this way.

EXAMPLE 65 dihydrochloride of ethyl trans-4-[[9-cyclopentyl-2-[[4-[[(1,1-dimethylethoxy)carbonyl]amino]cyclohexyl]methyl amino]-9H-purin-6-yl]amino]-benzoate The operation is carried out as in Stage 2 of Example 6 using trans 1-(NBOC)-4-(N-methyl)cyclohexane in place of trans 1-4 diaminocyclohexane. In this way the expected product is obtained.

EXAMPLE 66 dihydrochloride of ethyl trans-4-[[2-[(4-aminocyclohexyl)methylamino]-9-cyclopentyl-9H-purin-6-yl]amino]-benzoate The operation is carried out starting from the product of Example 65 by deprotecting the N-BOC amine by the action of trifluoroacetic acid. In this way the expected product is obtained.

EXAMPLE 67 trans-9-cyclopentyl-N2-(4-hydroxy-4-methylcyclohexyl)-N6-(phenylmethyl)-9H-purine-2,6-diamine dihydrochloride The operation is carried out as in Example 1 using benzylamine in Stage 2 of Example 1 in place of the hydrochloride of methyl 4-(aminomethyl)-benzoate, and in Stage 3 of Example 1,1-methyl-trans-1,4 aminocyclohexanol in place of trans 1-4 diaminocyclohexane.

EXAMPLE 68

N2-(4-amino-2-hydroxycyclo-hexyl)-9-cyclopentyl-N6-(phenylmethyl)-9H-purine-2,6-diamine dihydrochloride The operation is carried out as in Example 1 using benzylamine in Stage 2 of Example 1 in place of the hydrochloride of methyl 4-(aminomethyl)-benzoate, and in Stage 3 of Example 12-hydroxy-trans-1,4 diaminocyclohexane in place of trans 1-4 diaminocyclohexane.

EXAMPLE 69

N2-(4-amino-3-hydroxycyclo-hexyl)-9-cyclopentyl-N6-(phenylmethyl)-9H-purine-2,6-diamine dihydrochloride The operation is carried out as in Example 1 using benzylamine in Stage 2 of Example 1 in place of the hydrochloride of methyl 4-(aminomethyl)-benzoate, and in Stage 3 of Example 1,3-hydroxy-trans-1,4 diaminocyclohexane in place of trans 1-4 diaminocyclohexane.

EXAMPLE 70 trans-N2-(4-amino-3-fluoro-cyclohexyl)-9-cyclopentyl-N6-(phenylmethyl)-9H-purine-2,6-diamine dihydrochloride The operation is carried out as in Example 1 using benzylamine in Stage 2 of Example 1 in place of the hydrochloride of methyl 4-(aminomethyl)-benzoate, and in Stage 3 of Example 1,3-fluoro-trans-1,4 diaminocyclohexane in place of trans 1-4 diaminocyclohexane.

EXAMPLE 71 trans-2-[(4-aminocyclo-hexyl)oxy]-9-cyclopentyl-N-(phenylmethyl)-9H-purin-6-amine dihydrochloride The operation is carried out as in Example 1 using benzylamine in Stage 2 of Example 1 in place of the hydrochloride of methyl 4-(aminomethyl)-benzoate, and in Stage 3 of Example 1, trans-1,4 Bocaminocyclohexanol in the presence of sodium hydride (NaH) in dimethylformamide in place of trans 1-4 diaminocyclohexane.

EXAMPLE 72

4-[[9-cyclopentyl-6-[(phenyl-methyl)amino]-9H-purin-2-yl]amino]-cyclohexanone dihydrochloride The operation is carried out starting from the product of Example 4 by oxidation in DMF in the presence of (PDC) pyridinium dichromate and in this way the expected product is obtained after filtration on silica eluting with $CH_2Cl_2$/methanol: 80/20.

EXAMPLE 73

O-methyloxime of 4-[[9-cyclopentyl-6-[(phenylmethyl) amino]-9H-purin-2-yl]amino]-cyclohexanone dihydrochloride The operation is carried out starting from the product of Example 72 by reacting with O-methylhydroxylamine in ethanol under reflux and in this way the expected product is obtained.

EXAMPLE 74 trans-N2-(4-aminocyclohexyl)-9-cyclopentyl-N6-[2-[[(3,4-dichlorophenyl)-methyl]-amino]-ethyl]-9H-purine-2,6-diamine trihydrochloride Stage 1: 2-chloro-9-cyclopentyl-N-[2-[[(3,4-dichlorophenyl)-methyl]-amino]-ethyl]-9H-purin-6-amine 281 mg of the product obtained in Stage 1 of Example 7, 4 ml of methanol, 0.2 ml of 3,4-dichloro-benzaldehyde and 0.2 ml of acetic acid are mixed together and the reaction medium is agitated for 2 hours and 30 minutes, 0.1 g of $NaBH_3CN$ is added and agitation is carried out at ambient temperature for 1 hour. After evaporating the solvent, the residue is chromatographed on silica eluting with $CH_2Cl_2$/methanol/ammonium hydroxide (95/0.5/0.33) and 278.4 mg of expected product is obtained.

Stage 2: trans-N2-(4-aminocyclohexyl)-9-cyclopentyl-N6-[2-[[(3,4-dichlorophenyl)-methyl]-amino]-ethyl]-9H-purine-2,6-diamine trihydrochloride 278 mg of the product obtained in Stage 1 above, 4 ml of butanol, 360 mg of trans-1,4-diamino-cyclohexane are mixed together, the reaction medium is heated to 140° C. for approximately 10 hours, left to return to ambient temperature. After evaporating, the residue is chromatographed on silica eluting with $CH_2Cl_2$/methanol/ammonium hydroxide (85/15/1.5) and 93 mg of product is obtained which is salified by a solution of 1.4N HCl in EtOH.

115 mg of expected product is obtained.

| NNR in DMSO | |
|---|---|
| 1.36 (m)–1.49 (m) | the axial H's of the cyclohexyl |
| 1.71 (m)–1.90 (m)–2.04 (m) | the CH2's of the cyclopentyl |
| 2.05 (m) | the equatorial H's of the cyclohexyl |
| 3.02 (bs) 1H | $H_4$ |
| 3.25 (t) 2H–3.90 (bs) 2H | the $CH_2$—N |
| 3.69 (assumed masked) | axial $H_1$ |
| 4.24 (bs) 2H | N—$CH_2$— phenyl |
| 4.73 (m) 2H | CH of the cyclopentyl |
| 7.56 (dd) 1H | $H_c$ |
| 7.67 (d) 1H | $H_b$ |
| 7.87 (d) 1H | $H_a$ |
| 7.93 (bs) 3H | NH |
| 9.40 >1H | |

EXAMPLE 75 trans-N2-(4-aminocyclohexyl)-9-cyclopentyl-N6-[2-[[[4-(trifluoromethoxy)-phenyl]-methyl]-amino]-ethyl]-9H-purine-2,6-diamine trihydrochloride Stage 1: 2-chloro-9-cyclopentyl-N-[2-[[[4-(trifluoromethoxy)-phenyl]-methyl]-amino]-ethyl]-9H-purin-6-amine 281 mg of the product obtained in Stage 1 of Example 7, 4 ml of methanol, 0.16 ml of 4-trifluoromethoxy-benzaldehyde and 0.2 ml of acetic acid are mixed together, the reaction medium is agitated for 2 hours and 30 minutes, 0.1 g of $NaBH_3CN$ is added and agitation is carried out at ambient temperature for 1 hour. The solvent is evaporated off, the residue is chromatographed on silica eluting with $CH_2Cl_2$/methanol/ammonium hydroxide (95/0.5/0.33) and 129 mg of expected product is obtained.

Stage 2: trans-N2-(4-aminocyclohexyl)-9-cyclopentyl-N6-[2-[[[4-(trifluoromethoxy)-phenyl]-methyl]-amino]-ethyl]-9H-purine-2,6-diamine trihydrochloride 129 mg of the product obtained in Stage 1 above, 4 ml of butanol, 170 mg of trans-1,4-diamino-cyclohexane are mixed together, the reaction medium is heated to 140° C. for approximately 5 hours and 30 minutes and left to return to ambient temperature. After evaporating, the residue is chromatographed on silica eluting with $CH_2Cl_2$/methanol/ammonium hydroxide (85/15/1.5) and 90 mg of product is obtained which is salified by a 1.4N solution of HCl in EtOH.

65 mg of expected product is obtained.

| NMR in DMSO | |
|---|---|
| 1.39 (m)–1.53 (m) 4H | the axial H's of the cyclohexyl |
| 1.72 (m)–1.89 (m)–2.17 (m) | the CH2's of the cyclopentyl |
| 2.06 (m) 4H | the equatorial H's of the cyclohexyl |
| 3.03(bs) 1H | $H_4$ |
| 3.17 (t) 4H–4.00(bs) 4H | the CH2—N's |
| 3.73 (masked) 1H | axial $H_1$ |
| 4.27 (s) 2H | N—$CH_2$— phenyl |
| 4.76 (m) 1H | CH of the cyclopentyl |
| 7.38–7.75 AA'BB' | $F_3$C—O-Phenyl-$CH_2$ |
| 8.20 (s) 1H | N=CH |
| 8.09 ≤ 2H | $NH_2$ |
| 8.05–9.62 | the NH |

EXAMPLE 76 trans-N2-(4-aminocyclohexyl)-9-cyclopentyl-N6-[2-[[(3,5-dichlorophenyl)-methyl)]-amino]-ethyl]-9H-purine-2,6-diamine trihydrochloride Stage 1: 2-chloro-9-cyclopentyl-N-[2-[[(3,5-dichlorophenyl) methyl]-amino]-ethyl]-9H-purin-6-amine 281 mg of the product obtained in Stage 1 of Example 7, 4 ml of methanol, 0.16 ml of 3,5-dichloro-benzaldehyde and 0.2 ml of acetic acid are mixed together, the reaction medium is agitated for 2 hours and 30 minutes, 0.1 g of $NaBH_3CN$ is added and agitation is carried out at ambient temperature for 1 hour. After evaporating the solvent, the residue is chromatographed on silica eluting with $CH_2Cl_2$/methanol/ammonium hydroxide (95/0.5/0.33) and 119 mg of expected product is obtained.

Stage 2: trans-N2-(4-aminocyclohexyl)-9-cyclopentyl-N6-[2-[[(3,5-dichlorophenyl)-methyl]-amino]-ethyl]-9H-purine-2,6-diamine trihydrochloride 119 mg of the product obtained in Stage 1 above, 4 ml of butanol and 155 mg of trans-1,4-diamino-cyclohexane are mixed together, the reaction medium is heated to 140° C. for approximately 5 hours, another 155 mg of trans-1,4-diaminocyclohexane is added, heating is again carried out at 140° C. for 3 hours and the reaction medium is left to return to ambient temperature. After evaporating, the residue is chromatographed on silica eluting with $CH_2Cl_2$/methanol/ammonium hydroxide (85/15/1.5) and 17.3 mg of product is obtained which is salified with a 1.4N solution of HCl in EtOH. 23.8 mg of expected product is obtained.

| NMR in DMSO | |
|---|---|
| 1.38 (m)–1.51 (m) 4H | the axial H's of the cyclohexyl |
| 1.71 (m)–1.91 (m)–2.16 (m) | the CH2's of the cyclopentyl |
| 2.06 (m) | the equatorial H's of the cyclohexyl |
| 3.03 (bs) 1H | $H_4$ |
| 3.27 (bt)–3.97 (bs) | the $CH_2$—N's |
| 3.72 (masked) | $H_1$ |
| 4.26 (s) 2H | N—$CH_2$— phenyl |

| NMR in DMSO | |
|---|---|
| 4.76 (m) 1H | CH of the cyclopentyl |
| 7.59 (t) 1H | $H_a$ |
| 7.70 (d) 2H | the $H_b$'s |
| 8.03 (bs)–8.40 (bs)–9.60 (bs) | the NH's |
| 8.16 (s) | N=CH |

EXAMPLE 77 trans-N2-(4-aminocyclohexyl)-9-cyclopentyl-N6-[2-[[(4-fluorophenyl)-methyl]-amino]-ethyl]-9H-purine-2,6-diamine trihydrochloride Stage 1: 2-chloro-9-cyclopentyl-N-[2-[[(4-fluorophenyl)-methyl]-amino]-ethyl]-9H-purin-6-amine 281 mg of the product obtained in Stage 1 of Example 7, 4 ml of methanol, 0.15 ml of 4-fluoromethoxy-benzaldehyde and 0.2 ml of acetic acid are mixed together, the reaction medium is agitated for 2 hours and 30 minutes, 0.1 g of NaBH$_3$CN is added and agitation is carried out at ambient temperature for 1 hour. After evaporating the solvent, the residue is chromatographed on silica eluting with CH$_2$Cl$_2$/methanol/ammonium hydroxide (95/0.5/0.33) and 230 mg of expected product is obtained.

Stage 2: trans-N2-(4-aminocyclohexyl)-9-cyclopentyl-N6-[2-[[(4-fluorophenyl)-methyl]-amino]-ethyl]-9H-purine-2,6-diamine trihydrochloride 200 mg of the product obtained in Stage 1 above, 4 ml of butanol and 400 mg of trans-1,4-diamino-cyclohexane are mixed together, the reaction medium is heated to 140° C. for approximately 16 hours, then left to return to ambient temperature. After evaporating, the residue is chromatographed on silica eluting with CH$_2$Cl$_2$/methanol/ammonium hydroxide (85/15/1.5) and 54 mg of product is obtained which is salified with a 1.4N solution of HCl in EtOH. 57.7 mg of expected product is obtained.

| NMR in DMSO | |
|---|---|
| 1.39 (m)–1.53 (m) 4H | the axial H's of the cyclohexyl |
| 1.71 (m)–1.90 (m)–2.17 (m) | the CH2's of the cyclopentyl |
| 2.05 (m) 4H | the equatorial H's of the cyclohexyl |
| 3.02 (bs) 1H | $H_4$ |
| 3.25 (bt) 2H–3.99 (bs) 2H | the CH$_2$—N's |
| 3.74 1H | $H_1$ |
| 4.22 (s) 2H | N—C$\underline{H}_2$— phenyl |
| 4.77 (m) 1H | CH of the cyclopentyl |
| 7.22 (bt) 2H | the $H_b$'s |
| 7.66 (dd) 2H | the $H_a$'s |
| 8.09 (bs) > 2H | NH |
| 8.22 (s) 1H | N=CH |
| 8.60 (bs) 1H–9.54 (bs) > 1H | NH |

EXAMPLE 78 trans-N2-(4-aminocyclohexyl)-9-cyclopentyl-N6-[2-[[[4-(trifluoromethyl)-phenyl]-methyl]-amino]-ethyl]-9H-purine-2,6-diamine trihydrochloride Stage 1: 2-chloro-9-cyclopentyl-N-[2-[[[4-(trifluoromethyl)-phenyl]-methyl]-amino]-ethyl]-9H-purin-6-amine 281 mg of the product obtained in Stage 1 of Example 7, 4 ml of methanol, 0.19 ml of 4-trifluoromethyl-benzaldehyde and 0.2 ml of acetic acid are mixed together, the reaction medium is agitated for 2 hours and 30 minutes, 0.1 g of NaBH$_3$CN is added and agitation is carried out at ambient temperature for 1 hour. After evaporating the solvent, the residue is chromatographed on silica eluting with CH$_2$Cl$_2$/methanol/ammonium hydroxide (95/0.5/0.33) and 146 mg of expected product is obtained.

Stage 2: trans-N2-(4-aminocyclohexyl)-9-cyclopentyl-N6-[2-[[[4-(trifluoromethyl)-phenyl]-methyl]-amino]-ethyl]-9H-purine-2,6-diamine trihydrochloride 220 mg of the product obtained as in Stage 1 above, 4 ml of butanol, 571 mg of trans-1,4-diamino-cyclohexane are mixed together, the reaction medium is heated to 140° C. for approximately 5 hours and 30 minutes, then left to return to ambient temperature. After evaporating, the residue is chromatographed on silica eluting with CH$_2$Cl$_2$/methanol/ammonium hydroxide (85/15/1.5) and the product obtained is salified with a 1.4N solution of HCl in EtOH. 66 mg of expected product is obtained.

| NMR in DMSO | |
|---|---|
| 1.39–1.53 | the axial H's of the cyclohexyl |
| 1.70–1.90–2.02–2.16 | the CH2's of the cyclopentyl |
| 2.05 | the equatorial H's of the cyclohexyl |
| 2.84–3.04 | $H_4$ |
| 3.29–4.00 | the CH$_2$—N's |
| 3.55–3.73 | $H_1$ axial |
| 4.34 (s) | N—C$\underline{H}_2$— phenyl |
| 4.76 | CH of the cyclopentyl |
| 7.76–7.85 | F$_3$C-Phenyl |
| 8.20 | N=CH |
| 8.07–8.43–8.59 | mobile H's |

EXAMPLE 79 trans-N2-(4-aminocyclohexyl)-9-cyclopentyl-N6-[2-[[(3-chlorophenyl)-methyl]-amino]-ethyl]-9H-purine-2,6-diamine trihydrochloride.

Stage 1: 2-chloro-N-[2-[[(3-chlorophenyl)-methyl]-amino]-ethyl]-9-cyclopentyl-9H-purin-6-amine 281 mg of the product obtained in Stage 1 of Example 7, 4 ml of methanol, 0.2 ml of 3-chloro-benzaldehyde and 0.2 ml of acetic acid are mixed together, the reaction medium is agitated for 2 hours and 30 minutes, 0.1 g of NaBH$_3$CN is added and agitation is carried out at ambient temperature for 1 hour. After evaporating the solvent, the residue is chromatographed on silica eluting with CH₂Cl₂/methanol/ammonium hydroxide (95/0.5/0.33) and 172 mg of expected product is obtained.

Stage 2: trans-N2-(4-aminocyclohexyl)-9-cyclopentyl-N6-[2-[[(3-chlorophenyl)-methyl]-amino]-ethyl]-9H-purine-2,6-diamine trihydrochloride 111 mg of the product obtained in Stage 1 above, 4 ml of butanol and 312 mg of trans-1,4-diamino-cyclohexane are mixed together, the reaction medium is heated to 140° C. for approximately 5 hours and 30 minutes, then left to return to ambient temperature. After evaporating, the residue is chromatographed on silica eluting with CH₂Cl₂/methanol/ammonium hydroxide (85/15/1.5) and 92.7 mg of product is obtained which is salified with a 1.4N solution of HCl in EtOH. 68 mg of expected product is obtained.

| NNR in DMSO | |
|---|---|
| 1.38 (m)–1.52 (m) 4H | the axial H's of the cyclohexyl |
| 1.71 (m)–1.90 (m)–2.15 (m) | the CH2's of the cyclopentyl |
| 2.05 (m) 4H | the equatorial H's of the cyclohexyl |
| 3.04 (bs) 1H | H4 |
| 3.26 (bt) 3.98 (bs) | the CH₂—N's |
| 3.72 (masked) | axial H₁ |
| 4.25 (s) 2H | CH₂— phenyl |
| 4.76 (m) 1H | CH of the cyclopentyl |
| 7.45 (m) 2H and 7.55 (m) 1H | H_b, H_c and H_d |
| 7.70 (bs) 1H | H_a |
| 8.04 (bs) > 2H–8.38 (bs) 1H–9.53 (bs) > 1H | NH |
| 8.15 (s) 1H | CH═N |

EXAMPLE 80 trans-N2-(4-aminocyclohexyl)-N6-[(1,1'-biphenyl)-4-yl]-9-cyclopentyl-9H-purin-2,6-diamine dihydrochloride

Stage 1: 2-chloro-N-[(1,1'-biphenyl)-4-yl]-9-cyclopentyl-9H-purin-6-amine 257 mg of the product obtained in Stage 1 of Example 1 in 4 ml of n-butanol and 203 mg of 4-aminobiphenyl are introduced at ambient temperature and the reaction medium is agitated for 5 hours and 30 minutes in a bath at 100° C. then left to return to ambient temperature, followed by separating and rinsing with ether then drying under reduced pressure. In this way 328 mg of expected product is obtained.

Stage 2: trans-N2-(4-aminocyclohexyl)-N6-[(1.1'-biphenyl)-4-yl]-9-cyclopentyl-9H-purin-2,6-diamine dihydrochloride 342 mg of trans-1,4-diaminocyclohexane is taken to approximately 150° C. then 234 mg of the product obtained in Stage 1 above is added, the reaction medium is maintained under agitation at 140° C. for 9 hours 30 minutes then left to return to ambient temperature. Then 10 ml of water is added, followed by extracting with dichloromethane, drying and evaporating the solvent. The residue is chromatographed on silica (eluent: MeOH/NH₄OH 98/2), followed by taking up in 5 ml of an ethanolic solution of hydrochloric acid, evaporating the solvents, impasting the residue in ether and drying under reduced pressure at 60° C. 93 mg of expected product is recovered.

| NMR in DMSO | |
|---|---|
| 1.42 (m)–1.53 (m) | axial H's of the cyclohexyl |
| 1.72 (m)–1.91 (m) 4H | CH₂—CH of the cyclopentyl |
| 2.09 (m) | equatorial H's of the cyclohexyl |
| 2.09 (m)–2.21 (m) 4H | CH₂—CH₂—CH of the cyclopentyl |
| 3.03 (bs) | H₄ |
| 3.73 (bt) | H₁ |
| 4.84 (m) | CH of the cyclopentyl |
| 7.34 (tt) 1H | H_c |
| 7.46 (bt) 2H | the H_b's |
| 7.69 (bd)–8.07 (bd) 4H AA'BB' | the H_a's + phenyl |
| 8.07 3H | —NH |
| 8.93 (s) 1H | CH—C═N |
| 10.66 (bs) | NH |

EXAMPLE 81 trans-4-[[2-[(4-amino-cyclohexyl)-amino]-9-cyclopentyl-9H-purin-6-yl]-amino]-benzeneacetonitrile dihydrochloride

Stage 1: 4-[(2-chloro-9-cyclopentyl-9H-purin-6-yl)-amino]-benzeneacetonitrile.

257 Mg of the product obtained in Stage 1 of Example 1 in 4 ml of n-butanol and 159 mg of 4-aminophenylacetonitrile are introduced at ambient temperature and the reaction medium is agitated for 5 hours and 30 minutes in a bath at 100° C. then left to return to ambient temperature, followed by separating, rinsing with ether then drying under reduced pressure. In this way 296 mg of expected product is obtained.

Stage 2: trans-4-[[2-[(4-aminocyclohexyl)-amino]-9-cyclopentyl-9H-purin-6-yl]-amino]-benzene-acetonitrile dihydrochloride 684 mg of trans-1,4-diaminocyclohexane is taken to approximately 140° C. then 211 mg of the product obtained in Stage 1 above is added, the reaction medium is maintained under agitation at 140° C. for 6 hours then left to return to ambient temperature. Then 10 ml of water is added, followed by extracting with dichloromethane, drying and evaporating the solvent. The residue is chromatographed on silica (eluent: MeOH/NH₄OH 98/2), followed by taking up in 6 ml of an ethanolic solution of hydrochloric acid, evaporating the solvents, impasting the residue in ether, drying under reduced pressure at 60° C. and 199 mg of expected product is recovered.

| NNR in DMSO | |
|---|---|
| 1.46 (m) | axial H's of the cyclohexyl |
| 1.72 (m)–1.91 (m) | |

-continued

| NNR in DMSO | |
|---|---|
| 2.08 (masked) | the CH2's of the cyclopentyl |
| 2.21 (m) 8H | |
| 2.09 (m) | equatorial H's of the cyclohexyl |
| 3.02 (bs) | axial $H_4$ |
| 3.71 (bt) | axial $H_1$ |
| 3.98 (s) 2H | phenyl-C$\underline{H}_2$—CN |
| 4.84 | CH of the cyclopentyl |
| 7.36–7.97 AA'BB' | phenyl |
| 8.06 (bs) 3H | —NH |
| 8.81 (s) 1H | C$\underline{H}$=N |
| 10.46 (bs) 1H | NH |

EXAMPLE 82 trans-N2-(4-aminocyclohexyl)-9-cyclopentyl-N6-[4-(4-morpholinyl)-phenyl]-9H-purin-2,6-diamine dihydrochloride Stage 1: 2-chloro-9-cyclopentyl-N-[4-(4-morpholinyl)phenyl]-9H-purin-6-amine 257 mg of the product obtained in Stage 1 of Example 1 in 4 ml of n-butanol and 214 mg of 4-morpholinoaniline are introduced at ambient temperature and the reaction medium is agitated for 24 hours at ambient temperature, followed by separating, rinsing with ether then drying under reduced pressure at 50° C. In this way 286 mg of expected product is obtained.

Stage 2: trans-N2-(4-aminocyclohexyl)-9-cyclopentyl-N6-[4-(4-morpholinyl)-phenyl]-9H-purin-2,6-diamine dihydrochloride 800 mg of trans-1,4-diaminocyclohexane is taken to approximately 140° C. then 286 mg of the product obtained in Stage 1 above is added, the reaction medium is maintained under agitation at 140° C. for 5 hours then left to return to ambient temperature. Then 15 ml of water is added, followed by extracting with dichloromethane, drying and evaporating the solvent. The residue is chromatographed on silica (eluent: MeOH/NH$_4$OH 98/2), followed by taking up in 4 ml of an ethanolic solution of hydrochloric acid, evaporating the solvents, drying under reduced pressure to 50° C. and 143 mg of expected product is recovered.

| NMR in DMSO | |
|---|---|
| 1.40 (m)–1.540 (m) | axial H's of the cyclohexyl |
| 1.72 (m)–1.91 (m) | |
| 2.07 (m) 8H | the CH2's of the cyclopentyl |
| 2.21 (m) | |
| 2.07 (m) 4H | equatorial H's of the cyclohexyl |
| 3.02 (bs) | axial $H_4$ |
| 3.20 (m) 4H | the C$\underline{H}_2$—N |
| 3.71 (tt) 1H | axial $H_1$ |
| 3.81 (m) 4H | the C$\underline{H}_2$—O's |
| 4.83 (m) | C$\underline{H}$ of the cyclopentyl |
| 7.10–7.77 AA'BB' 4H | phenyl |
| 8.12 (bs) 3H–10.46 (bs) 1H | the NH's and NH$_2$'s |
| 8.78 (s) 1H | C$\underline{H}$=N |

EXAMPLE 83 trans-4-[[2-[(4-amino-cyclohexyl)-amino]-9-cyclopentyl-9H-purin-6-yl]-amino]-benzonitrile dihydrochloride Stage 1: 4-[(2-chloro-9-cyclopentyl-9H-purin-6-yl)amino]-benzonitrile.

1.03 g of the product obtained in Stage 1 of Example 1 in 14 ml of n-butanol and 567 mg of 4-aminobenzonitrile are introduced at ambient temperature and the reaction medium is agitated for 7 hours in a bath at 100° C. then left for 16 hours at ambient temperature, followed by partially concentrating, separating and rinsing with ether then drying under reduced pressure. In this way 1.13 g of expected product is obtained.

Stage 2: trans-4-[[2-[(4-aminocyclohexyl)-amino]-9-cyclopentyl-9H-purin-6-yl]amino]-benzonitrile dihydrochloride 2 g of trans-1,4-diaminocyclohexane is taken to approximately 150° C. then 1.18 g of the product obtained in Stage 1 above is added, the reaction medium is maintained under agitation to 140° C. for 6 hours then left to return to ambient temperature. Then 30 ml of water is added, followed by extracting with dichloromethane, drying and evaporating the solvent. The residue is chromatographed on silica (eluent: MeOH/NH$_4$OH 98/2), 130 mg of the product obtained is removed and taken up in 10 ml of ethanol, 4 ml of an ethanolic solution of hydrochloric acid is added, followed by separating, washing with ether, drying under reduced pressure at 50° C. and 144 mg of expected product is recovered.

| NMR in DMSO | |
|---|---|
| 1.41(m)–1.53(m) | axial H's of the cyclohexyl |
| 1.72(m)–1.91(m) | |
| 2.03(m) 8H | the CH2's of the cyclopentyl |
| 2.18(m) | |
| 2.07(m) 4H | equatorial H's of the cyclohexyl |
| 3.04(bs) 1H | $H_4$ |
| 3.70(tt) 1H | $H_1$ |
| 4.81(m) 1H | CH of the cyclopentyl |
| 7.76–8.23 4H AA'BB' | HN-phenyl-CN |
| 8.03(bs) 3H–10.55(bs) H | the NH's |
| 8.60(s) 1H | C$\underline{H}$=N |

EXAMPLE 84 trans-N2-(4-aminocyclohexyl)-9-cyclopentyl-N6-(4-nitrophenyl)-9H-purin-2,6-diamine dihydrochloride Stage 1: 2-chloro-9-cyclopentyl-N-(4-nitrophenyl)-9H-purin-6-amine.

257 mg of the product obtained in Stage 1 of Example 1 in 4 ml of n-butanol and 166 mg of 4-nitroaniline are introduced at ambient temperature and the reaction medium is agitated for 5 hours and 30 minutes in a bath at 100° C. then left to return to ambient temperature, followed by separating, rinsing with ether then drying under reduced pressure at 50° C. In this way 275 mg of expected product is obtained.

Stage 2: trans-N2-(4-aminocyclohexyl)-9-cyclopentyl-N6-(4-nitrophenyl)-9H-purin-2,6-diamine dihydrochloride 740 mg of trans-1,4-diaminocyclohexane is taken to approximately 150° C. then 466 mg of the product obtained in Stage 1 above is added, the reaction medium is maintained under agitation at 140° C. for 6 hours then left to return to ambient temperature. Then 15 ml of water is added, followed by extracting with dichloromethane, drying and evaporating the solvent. The residue is chromatographed on silica (eluent: MeOH/NH$_4$OH 98/2), 270 mg of the product obtained is removed and taken up in 10 ml of ethanol, 6 ml of an ethanolic solution of hydrochloric acid is added, followed by separating, washing with ether, drying under reduced pressure at 60° C. and 79 mg of expected product is recovered.

| NMR in DMSO | |
| --- | --- |
| 1.42(m)–1.53(m) 1.73(m)–1.92(m) | axial H's of the cyclohexyl |
| 2.10(m) 8H 2.18(m) | the CH2's of the cyclopentyl |
| 2.10(m) 4H | equatorial H's of the cyclohexyl |
| 3.04(bs) 1H | H$_4$ |
| 3.72(tt) 1H | H$_1$ |
| 4.81(m) 1H | CH of the cyclopentyl |
| 8.04(bs) 3H–10.64(bs) 1H | NH and NH$_2$ |
| 8.20–8.30 AA'BB' | HN-phenyl-NO$_2$ |
| 8.54(s) 1H | CH=N |

EXAMPLE 85 trans-N2-(4-aminocyclohexyl)-9-cyclopentyl-N6-[4-(trifluoromethyl)-phenyl]-9H-purin-2,6-diamine dihydrochloride Stage 1: 2-chloro-9-cyclopentyl-N-[4-(trifluoromethyl)-phenyl]-9H-purin-6-amine.

257 mg of the product obtained in Stage 1 of Example 1 in 4 ml of n-butanol and 193 mg of 4-trifluoromethylaniline are introduced at ambient temperature and the reaction medium is agitated for 7 hours in a bath at 100° C., left at ambient temperature, heated again for 4 hours at 100° C. then left to return to ambient temperature. The solvents are evaporated off, followed by impasting in ether then drying under reduced pressure at 50° C. In this way 314 mg of expected product is obtained.

Stage 2: trans-N2-(4-aminocyclohexyl)-9-cyclopentyl-N6-[4-(trifluoromethyl)-phenyl]-9H-purin-2,6-diamine dihydrochloride 684 mg of trans-1,4-diaminocyclohexane is taken to approximately 150° C. then 229 mg of the product obtained in Stage 1 above is added, the reaction medium is maintained under agitation at 140° C. for 5 hours then left to return to ambient temperature. Then 15 ml of water is added, followed by extracting with dichloromethane, drying and evaporating the solvent. The residue is chromatographed on silica (eluent: MeOH/NH$_4$OH 98/2), taken up in 10 ml of ethanol, 6 ml of an ethanolic solution of hydrochloric acid is added, followed by separating, washing with ether, drying under reduced pressure at 60° C. and 159 mg of expected product is recovered.

| NMR in DMSO | |
| --- | --- |
| 1.42(m)–1.62(m) | axial H's of the cyclohexyl |
| 1.72(m)–1.91(m)–2.19(m) 8H | the CH2's of the cyclopentyl |
| 2.10(m) 4H | equatorial H's of the cyclohexyl |
| 3.03(bs) 1H | H$_4$ |
| 3.72(tt) 1H | H$_1$ |
| 4.82(m) 1H | CH of the cyclopentyl |
| 7.66–8.23 | HN-phenyl-CF$_3$ |
| 8.01(bs) 3H–10.38(bs) 1H | the NH and NH$_2$'s |
| 8.57(s) 1H | CH=N |

EXAMPLE 86 trans-N2-(4-aminocyclohexyl)-N6-(4-aminophenyl)-9-cyclopentyl-9H-purin-2,6-diamine dihydrochloride 455 mg of product obtained as in Example 84 in 10 ml of tetrahydrofuran is hydrogenated for 16 hours at ambient temperature, in the presence of 230 mg of palladium on activated carbon, followed by filtering, rinsing with tetrahydrofuran and evaporating the solvent. The residue is chromatographed on silica (eluent: MeOH/NH$_4$OH 98/2), taken up in 10 ml of ethanol, 4 ml of an ethanolic solution of hydrochloric acid is added, followed by separating, washing with ether, drying under reduced pressure at 60° C. and 338 mg of expected product is recovered.

| NMR in DMSO | |
| --- | --- |
| 1.40(m)–1.53(m) 1.72(m)–1.91(m) | axial H's of the cyclohexyl |
| 2.08 (masked) 8H 2.21(m) | the CH2's of the cyclopentyl |
| 2.07(b) 4H | equatorial H's of the cyclohexyl |
| 3.01(bs) 1H | H$_4$ |
| 3.68(tt) 1H | H$_1$ |
| 4.85(qt) 1H | CH of the cyclopentyl |
| 7.40 2H–7.99 2H AA'BB' | HN-phenyl-NH$_2$ |
| 8.15(bs) 3H | mobile H's + N=CH—N |
| 8.93–10.71 | mobile H's |

EXAMPLE 87 trans-9-cyclopentyl-N2-(4-hydroxycyclohexyl)-N6-phenyl-9H-purin-2,6-diamine hydrochloride Stage 1: 2-chloro-9-cyclopentyl-N-phenyl-9H-purin-6-amine.

2.57 g of the product obtained in Stage 1 of Example 1 in 25 ml of n-butanol and 1.1 ml of aniline are introduced at ambient temperature, and the reaction medium is heated at a temperature of approximately 90 to 100° C. then left to return to ambient temperature, followed by diluting with 20 ml of isopropanol, agitating for 15 minutes, separating and rinsing with isopropanol then drying under reduced pressure at 40° C. In this way 2.43 g of expected product is obtained.

Stage 2: trans-9-cyclopentyl-N2-(4-hydroxy-cyclohexyl)-N6-phenyl-9H-purin-2,6-diamine hydrochloride 575 mg of trans-1,4-aminocyclohexanol are mixed together and the reaction medium is taken to a temperature of 50 to 60° C. then 313 mg of the product obtained in Stage 1 above is added and agitation is carried out at a temperature of 150 to 160° C. for approximately 20 hours. The reaction medium is then left to return to ambient temperature, taken up in ethyl acetate and water and then taken to a temperature of approximately 60° C. and left to settle, followed by re-extracting with ethyl acetate, washing with a saturated aqueous solution of sodium chloride, drying and evaporating to dryness. The residue is chromatographed on silica (eluent: $CH_2Cl_2$/MeOH 95/5), taken up in an ethanolic solution of hydrochloric acid and left to crystallize, followed by separating, drying under reduced pressure and 266 mg of expected product is recovered.

| NMR in DMSO | |
|---|---|
| 1.29(m) 4H–1.90(m) 4H | the CH2's of the cyclohexyl |
| 1.70(m) 2H–from 2 to 2.30 6H | the CH2's of the cyclopentyl |
| 3.43(m) 1H | $N_4$ |
| 3.67(m) 1H | $N_1$ |
| 4.84(q) 1H | —CH of the cyclopentyl |
| 7.12(t) 1H | $H_c$ |
| 7.37(t) 2H | the $H_b$'s |
| 7.94(bd) 2H | the $H_a$'s |
| 9.10(s)–10.80(s) | C$\underline{H}$=N + mobile H's |

EXAMPLE 88 dihydrochloride of ethyl trans-9-cyclopentyl-4-[[2-[(4-hydroxycyclohexyl) amino]-9H-purin-6-yl]-amino]-benzoate Stage 1: ethyl 4-[(2-chloro-9-cyclopentyl-9H-purin-6-yl)-amino]-benzoate 514 mg of the product obtained in Stage 1 of Example 1 in 5 ml of n-butanol and 396 mg of ethyl 4-amino benzoate are introduced at ambient temperature, and the reaction medium is heated at a temperature of approximately 90 to 100° C. for 19 hours, then left to return to ambient temperature, followed by diluting with 3 ml of isopropanol, agitating for 30 minutes, separating and rinsing with isopropanol then drying under reduced pressure at 50° C. In this way 761 mg of expected product is obtained.

Stage 2: dihydrochloride of ethyl trans-9-cyclopentyl-4-[[2-[(4-hydroxycyclohexyl)-amino]-9H-purin-6-yl]-amino]-benzoate 575 mg of trans-1,4-aminocyclohexanol is mixed together and the reaction medium is taken to a temperature of 50 to 60° C. then 385 mg of the product obtained in Stage 1 above is added and agitation is carried out at a temperature of approximately 140° C. for 17 hours, then the reaction medium is left to return to ambient temperature, taken up with ethyl acetate and with water and then taken to a temperature of approximately 50° C. The reaction medium is left to settle, followed by re-extracting with ethyl acetate, washing with a saturated aqueous solution of sodium chloride, drying and evaporating to dryness. The residue is taken up in an ethanolic solution of hydrochloric acid, left to crystallize, followed by separating, drying under reduced pressure at 50° C. and 381 mg of expected crude product is recovered. 347 mg of this hydrochloride is dissolved in water, an aqueous solution of ammonium hydroxide (pH: 12) then ethyl acetate are added, followed by decanting, extracting with ethyl acetate, washing with a saturated aqueous solution of sodium chloride, drying and evaporating to dryness. The residue is chromatographed on silica (eluent: $CH_2Cl_2$/MeOH 95/5), followed by taking up in an ethanolic solution of hydrochloric acid, leaving to crystallize, separating, drying under reduced pressure and 300 mg of expected pure product is recovered.

| NMR in DMSO | |
|---|---|
| 1.33(m) 7H | $CH_3$ + axial H's of the cyclohexyl |
| 1.64 to 2.30(m) | $CH_2$'s of the cyclopentyl + equatorial H's of the cyclohexyl |
| 3.46(m) 1H–3.69 1H | the CH's of the cyclohexyl |
| 4.32(t) 2H | $OCH_2$ |
| 4.83(m) 1H | —CH of the cyclopentyl |
| 7.93 2H–8.14 2H AA'BB' | HN-phenyl-$CO_2$Et |
| 8.88(bs) 1H | N—C$\underline{H}$=N |
| 10.70(bs) | mobile H |

EXAMPLE 89 trans-N-[2-[[2-[(4-amino-cyclohexyl)-amino]-9-cyclopentyl-9H-purin-6-yl]amino]-ethyl]-4-(trifluoromethyl)-benzamide dihydrochloride.

Stage 1: N-[2-[(2-chloro-9-cyclopentyl-9H-purin-6-yl)-amino]-ethyl]-4-(trifluoromethyl)-benzamide.

280 mg of the product obtained in Stage 1 of Example 7, 4 ml of methylene chloride, 0.28 ml triethylamine and 0.18 ml of 4-trifluoro-methylbenzoyl chloride are mixed together then the reaction medium is agitated at ambient temperature for one hour whilst entraining with ether, followed by separating and drying under reduced pressure. In this way 353 mg of expected product is obtained.

Stage 2: trans-N-[2-[[2-[(4-amino-cyclohexyl)-amino]-9-cyclopentyl-9H-purin-6-yl]-amino]-ethyl]-4-(trifluoromethyl)-benzamide dihydrochloride 342 mg of the product obtained in Stage 1 above and 428 mg of trans-1,4-diaminocyclohexane are mixed together and the reaction medium is heated to approximately 140° C. for 4 hours and 30 minutes. After evaporating the solvent, chromatography on silica is carried out eluting with methylene chloride/methanol/ammonium hydroxide in a proportion of 85/15/1.5, followed by taking up in an ethanolic solution of hydrochloric acid, leaving to crystallize, separating, drying under reduced pressure and 281.6 mg of expected product is recovered.

| NMR in DMSO | |
|---|---|
| 1.38(m)–1.48(m) 4H | the axial H's of the cyclohexyl |
| 1.70(m)–1.90(m) | |
| 2.02(masked) 8H | the CH2's of the cyclopentyl |
| 2.16(m) | |
| 2.04(m) 4H | equatorial H's of the cyclohexyl |
| 3.04(bs) 1H | axial $H_4$ |
| 3.61(m)–3.85(bs) | the C$\underline{H}_2$—NH's |
| 3.69(tt) | axial $H_1$ |
| 4.73(q) 1H | CH of the cyclopentyl |
| 7.79–8.01 AA'BB' | -phenyl- |
| 7.94(bs) ≧ 2H–8.13(s) 1H | N=C$\underline{H}$ + mobile H's |
| 8.64(bt) 1H | CH$_2$—N$\underline{H}$ |

EXAMPLE 89 trans-N-[2-[[2-[(4-amino-cyclohexyl)-amino]-9-cyclopentyl-9H-purin-6-yl]-amino]-ethyl]-4-methoxy-benzamide dihydrochloride Stage 1: N-[2-[(2-chloro-9-cyclopentyl-9H-purin-6-yl)-amino]-ethyl]-4-methoxy-benzamide 280 mg of the product obtained in Stage 1 of Example 7, 4 ml of methylene chloride, 0.28 ml triethylamine and 0.18 ml of 4-anisoyl chloride are mixed together then the reaction medium is agitated at ambient temperature for 30 minutes. Then 2 ml of water is added, followed by extracting with methylene chloride, drying and evaporating the solvents. Chromatography on silica is carried out (eluent methylene chloride/methanol/ammonium hydroxide 85/15/1.5 then CH$_2$Cl$_2$/CH$_3$CN 8/2 then methylene chloride/methanol/ammonium hydroxide 85/15/1.5). 275 mg of expected product is collected.

Stage 2: trans-N-[2-[[2-[(4-amino-cyclohexyl)-amino]-9-cyclopentyl-9H-purin-6-yl]-amino]-ethyl]-4-methoxy-benzamide dihydrochloride 263 mg of the product obtained in Stage 1 above and 360 mg of trans-1,4-diaminocyclohexane are mixed together and the reaction medium is heated to approximately 140° C. for 19 hours. After evaporating the solvent, chromatography on silica is carried out eluting with methylene chloride/methanol/ammonium hydroxide in a proportion of 85/15/1.5 followed by taking up in an ethanolic solution of hydrochloric acid, leaving to crystallize, separating, drying under reduced pressure and 194 mg of expected product is recovered.

| NMR in DMSO | |
|---|---|
| 1.37(m)–1.49(m) | the axial H's of the cyclohexyl |
| 1.70(m)–1.89(m) | |
| 2.00(m) | the CH2's of the cyclopentyl |
| 2.18(m) | |
| 2.07(m) | equatorial H's of the cyclohexyl |
| 3.06(bs) | axial $H_4$ |
| 3.58(m)–3.80(masked) | the C$\underline{H}_2$—NH's |
| 3.70(tt) | axial $H_1$ |
| 3.82(s) | -phenyl-O—C$\underline{H}_3$ |
| 4.74(q) | CH of the cyclopentyl |
| 6.96–7.81 AA'BB' | -phenyl- |
| 7.98(bs)–8.16(s)–8.81(s) | N=C$\underline{H}$ + mobile H's |
| 8.27(bt) | CH$_2$—N$\underline{H}$ |

EXAMPLE 91 trans-N-[2-[[2-[(4-amino-cyclohexyl)-amino]-9-cyclopentyl-9H-purin-6-yl]-amino]-ethyl]-3,5-dichloro-benzamide dihydrochloride Stage 1: N-[2-[(2-chloro-9-cyclopentyl-9H-purin-6-yl)-amino]-ethyl]-3,5-dichloro-benzamide 280 mg of the product obtained in Stage 1 of Example 7, 4 ml of methylene chloride, 0.28 ml of triethylamine and 255 mg of 3,5-dichlorobenzoyl chloride are mixed together then agitation is carried out at ambient temperature for 30 minutes. Then 2 ml of water is added, followed by extracting with methylene chloride, drying and evaporating the solvents. In this way 454 mg of expected product is obtained.

Stage 2: trans-N-[2-[[2-[(4-amino-cyclohexyl)-amino]-9-cyclopentyl-9H-purin-6-yl]-amino]-ethyl]-3,5-dichloro-benzamide dihydrochloride.

360 mg of the product obtained in Stage 1 above and 450 mg of trans-1,4-diaminocyclohexane are mixed together and the reaction medium is heated to approximately 140° C. for 6 hours.

After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 280 mg of expected product is recovered.

| NMR in DMSO | |
|---|---|
| 1.37(m)–1.52(m) 4H | the axial H's of the cyclohexyl |
| 1.71(m)–1.89(m) | |
| 2.01(masked) 8H | the CH2's of the cyclopentyl |
| 2.17(m) | |
| 2.06(m) 4H | equatorial H's of the cyclohexyl |
| 3.05(bs) 1H | axial $H_4$ |
| 3.58(m)–3.87(bs) | the C$\underline{H}_2$—NH's |
| 3.70(tt) | axial $H_1$ |
| 4.75(q) 1H | CH of the cyclopentyl |
| 7.71(bt) 1H | $H_a$ |
| 7.82(bd) 2H | the $H_b$'s |
| 8.03(bs) 3H | |
| 8.21(bs) | HN=C$\underline{H}$ + mobile H's |
| 8.96(bs) ≦ 1H | |
| 8.70(bt) 1H | CH$_2$—N$\underline{H}$ |

EXAMPLE 92 trans-N-[2-[[2-[(4-amino-cyclohexyl)-amino]-9-cyclopentyl-9H-purin-6-yl]-amino]-ethyl]-4-chloro-benzamide dihydrochloride Stage 1: N-[2-[(2-chloro-9-cyclopentyl-9H-purin-6-yl)-amino-ethyl]-4-chloro-benzamide 280 mg of the product obtained in Stage 1 of Example 7, 4 ml of methylene chloride, 0.28 ml of triethylamine and 0.16 ml of 4-chlorobenzoyl chloride are mixed together then the reaction medium is agitated at ambient temperature for approximately 1 hour. Then 4 ml of water is added, followed by extracting with methylene chloride, drying and evaporating the solvents. In this way 230 mg of expected product is obtained.

Stage 2: trans-N-[2-[[2-[(4-amino-cyclohexyl)-amino]-9-cyclopentyl-9H-purin-6-yl]-amino]-ethyl]-4-chloro-benzamide dihydrochloride 222 mg of the product obtained in Stage 1 above and 302 mg of trans-1,4-diaminocyclohexane are mixed together and the reaction medium is heated to 140° C. for 6 hours. After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 208 mg of expected product is recovered.

| NMR in DMSO | |
|---|---|
| 1.35(m)–1.49(m) 4H | the axial H's of the cyclohexyl |
| 1.70(m)–1.88(m) | |
| 1.97(masked) 8H | the CH2's of the cyclopentyl |
| 2.15(m) | |
| 2.04(m) 4H | equatorial H's of the cyclohexyl |
| 3.05(bs) 1H | axial $H_4$ |
| 3.57(m)–3.82(bs) | the C$\underline{H}_2$—NH's |
| 3.68(bt) | axial $H_1$ |
| 4.74(q) 1H | C$\underline{H}$ of the cyclopentyl |
| 7.50(bt)–7.85 AA'BB' | -phenyl- |
| 8.01(bs) 3H | |
| 8.20(bs) ≦ 1 | HN=C$\underline{H}$ + mobile H's |
| 8.97(bs) ≦ 1H | |
| 8.58(bt) 1H | CH$_2$—N$\underline{H}$ |

EXAMPLE 93 trans-N-[2-[[2-[(4-amino-cyclohexyl)-amino]-9-cyclopentyl-9H-purin-6-yl]-amino]-ethyl]-3,4-dichloro-benzamide dihydrochloride Stage 1: N-[2-[(2-chloro-9-cyclopentyl-9H-purin-6-yl)-amino]-ethyl]-3,4-dichloro-benzamide 280 mg of the product obtained in Stage 1 of Example 7, 4 ml of methylene chloride, 0.28 ml triethylamine and 251 mg of 3,4-dichlorobenzoyl chloride are mixed together then the reaction medium is agitated at ambient temperature for 1 hour. Then 2 ml of water is added, followed by extracting with methylene chloride, drying and evaporating the solvents. In this way 237 mg of expected product is obtained.

Stage 2: trans-N-[2-[[2-[(4-amino-cyclohexyl)-amino]-9-cyclopentyl-9H-purin-6-yl]-amino]-ethyl]-3,4-dichloro-benzamide dihydrochloride 225 mg of the product obtained in Stage 1 above and 285 mg of trans-1,4-diaminocyclohexane are mixed together and the reaction medium is heated to approximately 140° C. for 6 hours. After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 168 mg of expected product is recovered.

| NMR in DMSO | |
|---|---|
| 1.35(m)–1.50(m) 4H | the axial H's of the cyclohexyl |
| 1.69(m)–1.88(m) | |
| 2.04(masked) 8H | the CH2's of the cyclopentyl |
| 2.16(m) | |
| 2.04(m) 4H | equatorial H's of the cyclohexyl |
| 3.04(bs) 1B | assumed axial $H_4$ |
| 3.58(m)–3.82(bs) | the C$\underline{H}_2$—NH's |
| 3.68(bt) 1H | axial $H_1$ |
| 4.74(q) 1H | C$\underline{H}$ of the cyclopentyl |
| 7.71(d) 1H | $H_c$ |
| 7.80(dd) 1H | $H_b$ |
| 8.03(d) 1H | $H_a$ |
| 8.06(bs) 3H | |
| 8.24(bs) | N=C$\underline{H}$ + mobile H's |
| 9.15(bs) ≦ 1H | |
| 8.72(bt) 1H | CH$_2$—N$\underline{H}$ |

EXAMPLE 94 trans-N-[2-[[2-[(4-amino-cyclohexyl)-amino]-9-cyclopentyl-9H-purin-6-yl]-amino]-ethyl]-3,4-dimethoxy-benzamide dihydrochloride Stage 1: N-[2-[(2-chloro-9-cyclopentyl-9H-purin-6-yl)-amino]-ethyl]-3,4-dimethoxy-benzamide.

280 mg of the product obtained in Stage 1 of Example 7, 4 ml of methylene chloride, 0.28 ml of triethylamine and 241 mg of 3,4-dimethoxybenzoyl chloride are mixed together then the reaction medium is agitated at ambient temperature for approximately 5 hours. Then 2 ml of water is added, followed by extracting with methylene chloride, drying and evaporating the solvents. In this way 230 mg of expected product is obtained.

Stage 2: trans-N-[2-[[2-[(4-amino-cyclohexyl)-amino]-9-cyclopentyl-9H-purin-6-yl]-amino]-ethyl]-3,4-dimethoxy-benzamide dihydrochloride 230 mg of the product obtained in Stage 1 above and 293 mg of trans-1,4-diaminocyclohexane are mixed together and the reaction medium is heated to 140° C. for 6 hours. After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 99 mg of expected product is recovered.

| NMR in DMSO | |
|---|---|
| 1.35(m)–1.48(m) 4H | the axial H's of the cyclohexyl |
| 1.69(m)–1.88(m) 2.03(masked) 2.15(m) 8H | the CH2's of the cyclopentyl |
| 2.02(m) 4H | equatorial H's of the cyclohexyl |
| 3.05(bs) 1H | axial H$_4$ |
| 3.46(m)–3.77(bs) | the C$\underline{H}_2$—NH's |
| 3.67(bt) | H$_1$ assumed axial |
| 3.80(s) 3Hx2 | the OCH$_3$'s |
| 4.74(qt) 1H | C$\underline{H}$ of the cyclopentyl |
| 6.99(d) 1H | H$_3$' |
| 7.40 to 7.48(m) 2H | H$_4$'–H$_6$' |
| 7.99(bd) > 2H | NH$_2$ + N=C$\underline{H}$—N |
| 8.22(bs)–8.32(bt)–9.04(bs) | the mobile H's |

EXAMPLE 95 trans-N-[2-[[2-[(4-amino-cyclohexyl)-amino]-9-cyclopentyl-9H-purin-6-yl]-amino]-ethyl]-2-chloro-4-nitro-benzamide dihydrochloride Stage 1: 2-chloro-N-[2-[(2-chloro-9-cyclopentyl-9H-purin-6-yl)-amino]-ethyl]-4-nitro-benzamide 280 mg of the product obtained in Stage 1 of Example 7, 4 ml of methylene chloride, 0.28 ml of triethylamine and 264 mg of 2-chloronitrobenzoyl chloride are mixed together then the reaction medium is agitated at ambient temperature for 3 hours. Then 2 ml of water is added, followed by extracting with methylene chloride, drying and evaporating the solvents. In this way 295 mg of expected product is obtained.

Stage 2: trans-N-[2-[[2-[(4-amino-cyclohexyl)-amino]-9-cyclopentyl-9H-purin-6-yl]-amino]-ethyl]-2-chloro-4-nitro-benzamide dihydrochloride 295 mg of the product obtained in Stage 1 above and 362 mg of trans-1,4-diaminocyclohexane are mixed together and the reaction medium is heated to approximately 140° C. for 6 hours. After evaporating the solvent, chromatography on silica is carried out (eluent methylene chloride/methanol/ammonium hydroxide 85/15/1.5) then taken up in an ethanolic solution of hydrochloric acid, followed by leaving to crystallize, separating, drying under reduced pressure and 105 mg of expected product is recovered.

| NMR in DMSO | |
|---|---|
| 1.35(m)–1.50(m) 4H | the axial H's of the cyclohexyl |
| 1.70(m)–1.90(m) 1.97(masked) 8H 2.17(m) | the CH2's of the cyclopentyl |
| 2.05(m) 4H | equatorial H's of the cyclohexyl |
| 3.04(bs) 1H | axial H$_4$ |
| 3.59(m)–3.83(masked) | the C$\underline{H}_2$—NH's |
| 3.71(m) 1H | axial H$_1$ |
| 4.76(q) 1H | C$\underline{H}$ of the cyclopentyl |
| 7.77(d) 1H | H$_c$ |
| 8.19(dd) 1H | H$_b$ |
| 8.28(d) 1H | H$_a$ |
| 8.02(bs) 3H–9.02(bs) ≦ 1H | N=C$\underline{H}$ + mobile H's |
| 8.71(bt) 1H | CH$_2$—N$\underline{H}$ |

EXAMPLE 96 trans-N-[2-[[2-[(4-amino-cyclohexyl)-amino]-9-cyclopentyl-9H-purin-6-yl]-amino]-ethyl]-3,5-bis(trifluoromethyl)-benzamide dihydrochloride Stage 1: N-[2-[(2-chloro-9-cyclopentyl-9H-purin-6-yl]-amino]-ethyl]-3,5-bis(trifluoromethyl)-benzamide 280 mg of the product obtained in Stage 1 of Example 7, 4 ml of methylene chloride, 0.28 ml triethylamine and 241 mg of 3,5-trifluoro-methylbenzoyl chloride are mixed together then the reaction medium is agitated at ambient temperature for approximately 5 hours. Then 2 ml of water is added, followed by extracting with methylene chloride, drying and evaporating the solvents. In this way 390 mg of expected product is obtained.

Stage 2: trans-N-[2-[[2-[(4-amino-cyclohexyl)-amino]-9-cyclopentyl-9H-purin-6-yl]-amino]-ethyl]-3,5-bis(trifluoromethyl)-benzamide dihydrochloride 368 mg of the product obtained in Stage 1 above and 402 mg of trans-1,4-diaminocyclohexane are mixed together and the reaction medium is heated to 140° C. for 6 hours. After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 210 mg of expected product is recovered.

| NMR in DMSO | |
|---|---|
| 1.33(m)–1.48(m) 4H | the axial H's of the cyclohexyl |
| 1.69(m)–1.90(m)–2.15(m) 8H | the CH2's of the cyclopentyl |
| 2.00(m) 4H | equatorial H's of the cyclohexyl |
| 3.02(bs) 1H | axial H$_4$ |
| 3.63(m) | the C$\underline{H}_2$—NH's |
| 3.67(masked) | assumed axial H$_1$ |
| 4.74(qt) 1H | C$\underline{H}$ of the cyclopentyl |
| 8.25(s) 1H | H$_a$ |
| 8.45(s) 2H | the H$_b$'s |
| 8.04(bs) 3H | C$\underline{H}$=N + mobile H's |
| 9.07(bt) 1H | CH$_2$—N$\underline{H}$ |

EXAMPLE 97 trans-N-[2-[[2-[(4-amino-cyclohexyl)-amino]-9-cyclopentyl-9H-purin-6-yl]-amino]-ethyl]-4-(methylthio)-benzamide dihydrochloride Stage 1: N-[2-[(2-chloro-9-cyclopentyl-9H-purin-6-yl)-amino]-ethyl]-4-(methylthio)-benzamide 200 mg of 4-(methylthio) benzoic acid, 205 mg of 1-hydroxybenzotriazole hydrate, 290 mg of 1-(3-dimethylaminopropyl)-3-ethylcarbodiimide hydrochloride in 4 ml of dichloromethane are mixed together, 280 mg of the product obtained in Stage 1 of Example 7 is added and the reaction medium is agitated for 4 hours and 30 minutes at ambient temperature. Water is added, followed by separating, washing with ether, drying and 336 mg of expected product is collected.

Stage 2: trans-N-[2-[[2-[(4-amino-cyclohexyl)-amino]-9-cyclopentyl-9H-purin-6-yl]-amino]-ethyl]-4-(methylthio)-benzamide dihydrochloride 296 mg of the product obtained in Stage 1 above and 393 mg of trans-1,4-diaminocyclohexane are mixed together and the reaction medium is heated to approximately 140° C. for 6 hours. After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 51 mg of expected product is recovered.

| NMR in DMSO | |
|---|---|
| 1.35(m)–1.50(m) 4H 1.69(m)–1.90(m) | the axial H's of the cyclohexyl |
| 1.95(m) 8H 2.15(m) | the CH2's of the cyclopentyl |
| 2.03(m) 4H | equatorial H's of the cyclohexyl |
| 2.50(masked) | C$\underline{H}_3$-S-phenyl |
| 3.05(bs) 1H | axial $H_4$ |
| 3.57(m)–3.80(masked) | the C$\underline{H}_2$—N's |
| 3.68(bt) | axial $H_1$ |
| 4.73(q) 1H | C$\underline{H}$ of the cyclopentyl |
| 7.29–7.77 AA'BB' 4H | -phenyl- |
| 8.02(bs) ≦ 3H | |
| 8.21(bs) 1H 9.06(bs) ≦ 1H | N=C$\underline{H}$ + mobile H's |
| 8.45(bt) 1H | CH$_2$—N$\underline{H}$ |

EXAMPLE 98 trans-N-[2-[[2-[(4-amino-cyclohexyl)-amino]-9-cyclopentyl-9H-purin-6-yl]-amino]-ethyl]-4-fluoro-benzamide dihydrochloride Stage 1: N-[2-[(2-chloro-9-cyclopentyl-9H-purin-6-yl)-amino]ethyl]-4-fluoro-benzamide 280 mg of the product obtained in Stage 1 of Example 7, 4 ml of methylene chloride, 0.28 ml of triethylamine and 0.14 ml of 4-fluorobenzoyl chloride are mixed together then the reaction medium is agitated at ambient temperature for 2 hours. Then ether is added, followed by separating, drying, taking up in water, extracting with methylene chloride, drying and evaporating the solvents. In this way 283 mg of expected product is obtained.

Stage 2: trans-N-[2-[[2-[(4-amino-cyclohexyl)-amino]-9-cyclopentyl-9H-purin-6-yl]-amino]-ethyl]-4-fluoro-benzamide dihydrochloride 247 mg of the product obtained in Stage 1 above and 350 mg of trans-1,4-diaminocyclohexane are mixed together and the reaction medium is heated to 140° C. for 6 hours. After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 130 mg of expected product is recovered.

| NMR in DMSO | |
|---|---|
| 1.37(m)–1.48(m) 4H 1.69(m)–1.89(m) | the axial H's of the cyclohexyl |
| 2.03(masked) 8H 2.15(m) | the CH2's of the cyclopentyl |
| 2.03(m) 4H | equatorial H's of the cyclohexyl |
| 3.06(bs) 1H | axial $H_4$ |
| 3.47 to 3.96(m) | the C$\underline{H}_2$—NH's + assumed axial H1 |
| 4.74(qt) 1H | C$\underline{H}$ of the cyclopentyl |
| 7.25(t) 2H–7.90(t) 2H | F-phenyl-CO |
| 8.04(bs) >2H | $NH_2$ + N=CH |
| 8.23(bs) <1H | |
| 8.53(bt) <1H 9.07(bs) <1H | the mobile H's |

EXAMPLE 99 trans-N-[2-[[2-[(4-amino-cyclohexyl)-amino]-9-cyclopentyl-9H-purin-6-yl]-amino]-ethyl]-3-(trifluoromethyl)-benzamide dihydrochloride Stage 1: N-[2-[(2-chloro-9-cyclopentyl-9H-purin-6-yl)-amino]-ethyl]-3-(trifluoromethyl)-benzamide 280 mg of the product obtained in Stage 1 of Example 7, 203 mg of 1-hydroxybenzotriazole hydrate, 287 mg of 1-(3-dimethylaminopropyl)-3-ethylcarbodiimide hydrochloride in 4 ml of dichloromethane are mixed together, 230 mg of 3-trifluoromethyl benzoic acid is added and agitation is carried out for 6 hours and 30 minutes at ambient temperature. Water is added, followed by separating, washing with ether, drying and 307 mg of expected product is collected.

Stage 2: trans-N-[2-[[2-[(4-amino-cyclohexyl)-amino]-9-cyclopentyl-9H-purin-6-yl]-amino]-ethyl]-3-(trifluoromethyl)-benzamide dihydrochloride 290 mg of the product obtained in Stage 1 above and 365 mg of trans-1,4-diaminocyclohexane are mixed together and the reaction medium is heated to approximately 140° C. for 6 hours. After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 206 mg of expected product is recovered.

| NMR in DMSO | |
|---|---|
| 1.36(m)–1.51(m) 4H 1.70(m)–1.90(m) | the axial H's of the cyclohexyl |
| 1.96(m) 8H 2.16(m) | the CH2's of the cyclopentyl |
| 2.04(m) 4H | equatorial H's of the cyclohexyl |
| 3.05(bs) 1H | axial $H_4$ |
| 3.61(m)–3.88(bs) | the C$\underline{H}_2$—NH's |
| 3.70(bt) 1H | axial $H_1$ |
| 4.74(q) 1H | C$\underline{H}$ of the cyclopentyl |
| 7.70(t) 1H | $H_c$ |
| 7.86(bd) 1H | $H_b$ |
| 8.13(bs) 2H | $H_a$ and $H_d$ |

-continued

| NMR in DMSO | |
|---|---|
| 7.99(bs) ≧2H | |
| 8.17(s) 1H | N=C$\underline{H}$ + mobile H's |
| 8.88(bs) ≦1H | |
| 8.71(bt) 1H | CH$_2$—N$\underline{H}$ |

EXAMPLE 100 trans-N-[2-[[2-[(4-amino-cyclohexyl)-amino]-9-cyclopentyl-9H-purin-6-yl]-amino]-ethyl]-3-(trifluoromethoxy)-benzamide dihydrochloride Stage 1: N-[2-[(2-chloro-9-cyclopentyl-9H-purin-6-yl)-amino]-ethyl]-3-(trifluoromethoxy)-benzamide.

280 mg of the product obtained in Stage 1 of Example 7, 203 mg of 1-hydroxybenzotriazole hydrate, 287 mg of 1-(3-dimethylaminopropyl)-3-ethyl-carbodiimide hydrochloride in 4 ml of dichloromethane are mixed together, 230 mg of 3-trifluoromethoxy benzoic acid is added and agitation is carried out for 4 hours and 30 minutes at ambient temperature. Water is added, followed by extracting with methylene chloride, drying, evaporating the solvents, recrystallizing from ether, separating, drying and 326 mg of expected product is collected.

Stage 2: trans-N-[2-[([2-[(4-amino-cyclohexyl)-amino]-9-cyclopentyl-9H-purin-6-yl]-amino]-ethyl]-3-(trifluoromethoxy)-benzamide dihydrochloride 300 mg of the product obtained in Stage 1 above and 365 mg of trans-1,4-diaminocyclohexane are mixed together and the reaction medium is heated to approximately 140° C. for 6 hours. After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 200 mg of expected product is recovered.

| NMR in DMSO | |
|---|---|
| 1.36(m)–1.50(m) 4H | the axial H's of the cyclohexyl |
| 1.70(m)–1.90(m) | |
| 1.96(m) 8H | the CH2's of the cyclopentyl |
| 2.15(m) | |
| 2.04(m) 4H | equatorial H's of the cyclohexyl |
| 3.05(bs) 1H | axial H$_4$ |
| 3.60(m)–3.84(bs) | the C$\underline{H}_2$—NH's |
| 3.70(tt) 1H | axial H$_1$ |
| 4.74(q) 1H | C$\underline{H}$ of the cyclopentyl |
| 7.49(bd) 1H | H$_b$ |
| 7.59(t) 1H | H$_c$ |
| 7.75(bt) 1H | H$_a$ |
| 7.87(bd) 1H | H$_d$ |
| 7.94(bs) ≦3H–8.10(bs) 1H | N=C$\underline{H}$ + mobile H's |
| 8.60(bt) 1H | CH$_2$—N$\underline{H}$ |

EXAMPLE 101 trans-N-[2-[[2-[(4-amino-cyclohexyl)-amino]-3-chloro-9-cyclopentyl-9H-purin-6-yl]-amino]-ethyl]-benzamide dihydrochloride Stage 1: 3-chloro-N-[2-[(2-chloro-9-cyclopentyl-9H-purin-6-yl)-amino]-ethyl]-benzamide 190 mg of 3-chlorobenzoic acid, 205 mg of 1-hydroxybenzotriazole hydrate, 287 mg of 1-(3dimethylaminopropyl)-3-ethylcarbodiimide hydrochloride in 4 ml of dichloromethane are mixed together, 280 mg of the product obtained in Stage 1 of Example 7 is added and the reaction medium is agitated for 5 hours and 30 minutes at ambient temperature. Water is added, followed by extracting with methylene chloride, drying, evaporating the solvents, recrystallizing from ether, separating, drying and 334 mg of expected product is collected.

Stage 2 trans-N-[2-[[2-[(4-amino-cyclohexyl)-amino]-3-chloro-9-cyclopentyl-9H-purin-6-yl]-amino]-ethyl]-benzamide: dihydrochloride 292 mg of the product obtained in Stage 1 above and 396 mg of trans-1,4-diaminocyclohexane are mixed together and the reaction medium is heated to approximately 140° C. for 6 hours. After evaporating the solvent, chromatography on silica is carried out (eluent methylene chloride/methanol/ammonium hydroxide 85/15/1.5) followed by taking up in an ethanolic solution of hydrochloric acid, leaving to crystallize, separating, drying under reduced pressure and 127.5 mg of expected product is recovered.

| NMR in DMSO | |
|---|---|
| 1.35(m)–1.50(m) 4H | the axial H's of the cyclohexyl |
| 1.69(m)–1.90(m) | |
| 1.97(m) 8H | the CH2's of the cyclopentyl |
| 2.15(m) | |
| 2.03(m) 4H | equatorial H's of the cyclohexyl |
| 3.05(bs) 1H | axial H$_4$ |
| 3.58(m)–3.81(masked) | the C$\underline{H}_2$—NH's |
| 3.68(bt) 1H | axial H$_1$ |
| 4.74(q) 1H | C$\underline{H}$ of the cyclopentyl |
| 7.47(t) 1H | H$_c$ |
| 7.57(ddd) 1H | H$_d$ |
| 7.78(bd) 1H | H$_b$ |
| 7.84(bs) 1H | H$_a$ |
| 8.03(bs) 3H | |
| 8.23(bs) 1H | N=C$\underline{H}$ + mobile H's |
| 9.06(bs) 1H | |
| 8.63(bt) 1H | CH$_2$—N$\underline{H}$ |

EXAMPLE 102 dihydrochloride of trans-4-[[2-[(4-amino-cyclohexyl)-amino]-9-cyclopentyl-9H-purin-6-yl]-amino]-benzeneethyl acetate Stage 1: 4-[(2-chloro-9-cyclopentyl-9H-purin-6-yl)-amino]-benzeneethyl acetate 257 mg of the product obtained in Stage 1 of Example 1 in 4 ml of ethanol and 215 mg of 4-amino-benzeneethyl acetate and 165 mg of potassium carbonate are mixed together at ambient temperature then the reaction medium is heated at a temperature of approximately 90° C. for 20 hours then left to return to ambient temperature, diluted with 15 ml of ethyl acetate and 10 ml of water, followed by extracting with ethyl acetate, washing with water, evaporating the solvents, taking up in isopropyl ether, separating and drying under reduced pressure at 50° C. In this way 222 mg of expected product is obtained.

Stage 2: dihydrochloride of trans-4-[[2-[(4-amino-cyclohexyl)-amino]-9-cyclopentyl-9H-purin-6-yl]-amino]-benzeneethyl acetate 180 mg of the product obtained in Stage 1 above and 360 mg of trans-1,4-diaminocyclohexane are mixed together and the reaction medium is heated to approximately 140° C. for 5 hours. After evaporating the solvent, chromatography on silica is carried out (eluent methanol/ammonium hydroxide 98/2) followed by taking up in an ethanolic solution of hydrochloric acid, evaporating the solvents, impasting in ether, separating, drying under reduced pressure at 50° C. and 142 mg of expected product is recovered.

| NMR in DMSO | |
|---|---|
| 1.20(t) | C$H_3$—C$H_2$—O |
| 1.40(m)–1.49(m) 4H | the axial H's of the cyclohexyl |
| 1.72(m)–1.91(m) | |
| 2.07(masked) 8H | the CH2's of the cyclopentyl |
| 2.20(m) | |
| 2.07(m) 4H | equatorial H's of the cyclohexyl |
| 3.02(bs) 1H | axial $H_4$ |
| 3.63(s) 2H | phenyl-C$H_2$—CO |
| 3.70(bt) 1H | axial $H_1$ |
| 4.10(q) | C$H_3$—C$H_2$—O |
| 4.84(q) 1H | C$H$ of the cyclopentyl |
| 7.27–7.90 AA'BB' | -phenyl- |
| 8.07(bs) ≧3H | |
| 8.93(bs) 1H | N═C$H$ + mobile H's |
| 10.56(bs) 1H | |

EXAMPLE 103 trans-4-[[2-[(4-amino-cyclohexyl)-amino]-9-cyclopentyl-9H-purin-6-yl)]-amino]-N-(2-thiazolyl)-benzenesulphonamide dihydrochloride Stage 1: 4-[(2-chloro-9-cyclopentyl-9H-purin-6-yl)-amino]-N-(2-thiazolyl)-benzenesulphonamide 257 mg of the product obtained in Stage 1 of Example 1 in 4 ml of n-butanol and 306 mg of 4-amino-N-(2-thiazolyl) benzenesulphonamide are introduced at ambient temperature and the reaction medium is immersed in a bath at a temperature of approximately 100° C. for 14 hours under agitation then left to return to ambient temperature, followed by separating, rinsing with ether then drying under reduced pressure at 50° C. In this way 74 mg of expected product is obtained.

Stage 2: trans-4-[[2-[(4-amino-cyclohexyl)-amino]-9-cyclopentyl-9H-purin-6-yl]-amino]-N-(2-thiazolyl)-benzenesulphonamide dihydrochloride 400 mg of trans-1,4-diaminocyclohexane is taken to approximately 150° C. then 333 mg of the product obtained in Stage 1 above is added, the reaction medium is left under agitation for 3 hours then left to return to ambient temperature and diluted with 30 ml of dichloromethane. 10 ml of methanol is added, followed by washing with 10 ml of water, drying and evaporating the solvents. Chromatography on silica is carried out (eluent: MeOH/NH$_4$OH 98/2), the residue is taken up in an ethanolic solution of hydrochloric acid, followed by evaporating the solvents, impasting in ether, separating, drying under reduced pressure at ambient temperature and 66 mg of expected product is recovered.

| NMR in DMSO | |
|---|---|
| 1.38(m)–1.51(m) 4H | the axial H's of the cyclohexyl |
| 1.71(m)–1.91(m) | |
| 2.05(m) 8H | the CH2's of the cyclopentyl |
| 2.18(m) | |
| 2.09(m) 4H | equatorial H's of the cyclohexyl |
| 3.02(bs) 1H | axial $H_4$ |
| 3.69(masked) 1H | axial $H_1$ |
| 4.82(q) 1H | C$H$ of the cyclopentyl |
| 6.81(d)–7.20(d) 2H | $H_a$ and $H_b$ |
| 7.77–8.15 AA'BB' 4H | -phenyl- |
| 8.06(bs) ≦3H | |
| 8.81(s) 1H | N═C$H$ + mobile H's |
| 10.64(bs) ≦1H | |

EXAMPLE 104 trans-4-[[2-[(4-amino-cyclohexyl)-amino]-9-cyclopentyl-9H-purin-6-yl]-amino]-benzenesulphonamide dihydrochloride Stage 1: 4-[(2-chloro-9-cyclopentyl-9H-purin-6-yl)-amino]-benzenesulphonamide.

257 mg of the product obtained in Stage 1 of Example 1 in 4 ml of n-butanol and 207 mg of sulphanilamide are introduced at ambient temperature and the reaction medium is immersed in a bath at a temperature of approximately 100° C. for 16 hours under agitation then left to return to ambient temperature, followed by separating, rinsing with ether then drying under reduced pressure at 50° C. In this way 339 mg of expected product is obtained.

Stage 2: trans-4-[[2-[(4-amino-cyclohexyl)-amino]-9-cyclopentyl-9H-purin-6-yl]-amino]-benzene-sulphonamide dihydrochloride 400 mg of trans-1,4-diaminocyclohexane is taken to approximately 150° C. then 275 mg of the product obtained in Stage 1 above is added, the reaction medium is left under agitation for 3 hours then left to return to ambient temperature, followed by evaporating the solvents, and chromatography on silica (eluent: MeOH/NH$_4$OH 98/2). The residue is taken up in an ethanolic solution of hydrochloric acid, followed by evaporating the solvents, impasting in ether, separating, drying under reduced pressure at ambient temperature and 205 mg of expected product is recovered.

| NMR in DMSO | |
|---|---|
| 1.40(m)–1.55(m) 4H | the axial H's of the cyclohexyl |
| 1.72(m)–1.91(m) | |
| 2.08(masked) 8H | the CH2's of the cyclopentyl |
| 2.19(m) | |
| 2.08(d) 4H | equatorial H's of the cyclohexyl |
| 3.03(bs) 1H | axial $H_4$ |
| 3.71(tt) 1H | axial $H_1$ |
| 4.84(qt) 1H | C$\underline{H}$ of the cyclopentyl |
| 7.83–8.16 AA'BB' 4H | -phenyl- |
| 8.08(bs) >2H | $NH_2$-cyclohexyl + N=C$\underline{H}$—N |
| 7.17(bs) | |
| 2H-8.88(bs) 1H | mobile H's |
| 10.75(bs) 1H | |

EXAMPLE 105 trans-N2-(4-aminocyclohexyl)-9-cyclopentyl-N6-(4-methoxyphenyl)-9H-purine-2,6-diamine dihydrochloride

Stage 1: 2-chloro-9-cyclopentyl-N-(4-methoxyphenyl)-9H-purin-6-amine 257 mg of the product obtained in Stage 1 of Example 1 in 4 ml of n-butanol and 148 mg of p-anisidine are introduced at ambient temperature and the reaction medium is immersed in a bath at a temperature of approximately 100° C. for 17 hours under agitation then left to return to ambient temperature, followed by separating, rinsing with ether then drying under reduced pressure at 50° C. In this way 239 mg of expected product is obtained.

Stage 2: trans-N2-(4-aminocyclohexyl)-9-cyclopentyl-N6-(4-methoxyphenyl)-9H-purine-2,6-diamine dihydrochloride 400 mg of trans-1,4-diaminocyclohexane is taken to approximately 150° C. then 172 mg of the product obtained in Stage 1 above is added, the reaction medium is left under agitation for 2 hours and 30 minutes then left to return to ambient temperature. After evaporating the solvents, the residue is chromatographed on silica (eluent: MeOH/$NH_4OH$ 98/2). The residue is taken up in an ethanolic solution of hydrochloric acid, followed by evaporating the solvents, impasting in ether, separating, drying under reduced pressure at ambient temperature and 188 mg of expected product is recovered.

| NMR in DMSO | |
|---|---|
| 1.36(m)–1.51(m) 4H | the axial H's of the cyclohexyl |
| 1.71(m)–1.91(m) | |
| 2.05(masked) 8H | the CH2's of the cyclopentyl |
| 2.20(m) | |
| 2.06(d) 4H | equatorial H's of the cyclohexyl |
| 3.02(bs) 1H | axial $H_4$ |
| 3.68(tt) 1H | axial $H_1$ |
| 3.78(s) 3H | OC$\underline{H}_3$ |
| 4.82(qt) 1H | C$\underline{H}$ of the cyclopentyl |
| 6.98 2H–7.78 2H AA'BB' | -phenyl-O |
| 8.06(bs) <3H | $NH_2$-cyclohexyl + N=C$\underline{H}$—N |
| 8.83(bs) <2H–10.53(bs) <1H | mobile H's |

EXAMPLE 106 dihydrochloride of butyl trans-4-[[2-[(4-amino-cyclohexyl)-amino]-9-cyclopentyl-9H-purin-6-yl]-amino]-benzeneacetate

Stage 1: butyl 4-[(2-chloro-9-cyclopentyl-9H-purin-6-yl)amino]-benzeneacetate.

257 mg of the product obtained in Stage 1 of Example 1 in 4 ml of ethanol, 215 mg of ethyl 4-amino phenyl methyl carboxylate and 165 mg of potassium carbonate are mixed together at ambient temperature then the reaction medium is heated at a temperature of approximately 100° C. for 24 hours then left to return to ambient temperature. After evaporating the solvents, dilution is carried out with 10 ml of water, followed by extracting with ethyl acetate, evaporating the solvents and chromatography on silica (eluent: $CH_2Cl_2$/AcOEt 8/2).

Stage 2: dihydrochloride of butyl trans-4-[[2-[(4-amino-cyclohexyl)-amino]-9-cyclopentyl-9H-purin-6-yl]-amino]-benzene-acetate 400 mg of trans-1,4-diaminocyclohexane and 200 mg of the product obtained in Stage 1 above are taken to approximately 150° C., the reaction medium is left under agitation for 5 hours and 30 minutes then left to return to ambient temperature. The solvents are evaporated off and the residue is chromatographed on silica (eluent: MeOH/$NH_4OH$ 98/2). The residue is taken up in an ethanolic solution of hydrochloric acid, followed by evaporating the solvents, impasting in ether, separating, drying under reduced pressure at ambient temperature and 165 mg of expected product is recovered.

| NMR in DMSO | |
|---|---|
| 0.88(t) | C$\underline{H}_3$—$CH_2$—$CH_2$—$CH_2O$ |
| 1.32(m) | $CH_3$—C$\underline{H}_2$—$CH_2$—$CH_2O$ |
| 1.56(m) | $CH_3$—$CH_2$—C$\underline{H}_2$—$CH_2O$ |
| 4.06(t) | $CH_3$—$CH_2$—$CH_2$—C$\underline{H}_2O$ |
| 1.37(m)–1.52(m) 4H | the axial H's of the cyclohexyl |
| 1.72(m)–1.92(m) | |
| 2.08(m) 8H | the CH2's of the cyclopentyl |
| 2.21(m) | |
| 2.08(d) 4H | equatorial H's of the cyclohexyl |
| 3.02(bs) 1H | axial $H_4$ |
| 3.64(s) 2H | -phenyl-C$\underline{H}_2$—CO |
| 3.70(tt) 1H | axial $H_1$ |
| 4.85(qt) 1H | C$\underline{H}$ of the cyclopentyl |
| 7.28 2H–7.90 2H AA'BB' | -phenyl-O |
| 8.10(bs) <3H | $NH_2$-cyclohexyl + N=C$\underline{H}$—N |
| 9.02(bs) <1H–10.67(bs) <1H | mobile H's |

EXAMPLE 107 trans-N2-(4-aminocyclohexyl)-9-cyclopentyl-N6-[4-(1H-tetrazol-5-yl) phenyl]-9H-purin-2,6-diamine dihydrochloride 296 mg of the product obtained in Example 83 in 3 ml of toluene and 0.26 ml of azido tributyltin are mixed together at ambient temperature then the reaction medium is heated at a temperature of approximately 120° C. for 22 hours then left to return to ambient temperature. 7 ml of tetrahydrofuran is added to the suspension obtained, gaseous hydrochloric acid is bubbled through for 1 minute then nitrogen is bubbled through for 10 minutes, the product obtained is separated, followed by rinsing with ether and drying under reduced pressure at 50° C. In this way 374 mg of expected product is obtained.

NMR in DMSO

| | |
|---|---|
| 1.43(m)–1.55(m) 4H | the axial H's of the cyclohexyl |
| 1.72(m)–1.91(m) | |
| 2.09(m) 8H | the CH2's of the cyclopentyl |
| 2.20(m) | |
| 2.09(m) 4H | equatorial H's of the cyclohexyl |
| 3.06(bs) 1H | axial $H_4$ |
| 3.75(tt) 1H | axial $H_1$ |
| 4.83(m) 1H | C$\underline{H}$ of the cyclopentyl |
| 8.12–8.23 AA'BB' | -phenyl-O |
| 8.03(bs) ≧3H | |
| 8.84(bs) 1H | N=C$\underline{H}$—N + mobile H's |
| 10.69(bs) 1H | |

EXAMPLE 108 trans-3-[[2-[(4-amino-cyclohexyl)-amino]-9-cyclopentyl-9H-purin-6-yl]-amino]-benzamide dihydrochloride Stage 1: 3-[(2-chloro-9-cyclopentyl-9H-purin-6-yl)-amino]-benzamide 257 mg of the product obtained in Stage 1 of Example 1 in 4 ml of n-butanol and 163 mg of 3-amino benzamide are introduced at ambient temperature and the reaction medium is immersed in a bath at a temperature of approximately 100° C. for 16 hours under agitation then left to return to ambient temperature, followed by separating, rinsing with ether then drying under reduced pressure at ambient temperature. In this way 334 mg of expected product is obtained.

Stage 2: trans-3-[[2-[(4-amino-cyclohexyl)-amino]-9-cyclopentyl-9H-purin-6-yl]-amino]-benzamide dihydrochloride 400 mg of trans-1,4-diaminocyclohexane and 250 mg of the product obtained in Stage 1 above are taken to approximately 150° C., the reaction medium is left under agitation for 5 hours then left to return to ambient temperature for 16 hours. 8 ml of methanol is added, chromatography on silica is carried out (eluent: MeOH/NH$_4$OH 98/2). The residue is taken up in an ethanolic solution of hydrochloric acid, followed by evaporating the solvents, impasting in ether, separating, drying under reduced pressure at ambient temperature and 101 mg of expected product is recovered.

NMR in DMSO

| | |
|---|---|
| 1.38(m)–1.52(m) 4H | the axial H's of the cyclohexyl |
| 1.71(m)–1.92(m) | |
| 2.03(masked) | the CH2's of the cyclopentyl |
| 2.21(m) 8H | |
| 2.05(d) 4H | equatorial H's of the cyclohexyl |
| 2.99(bs) 1H | axial $H_4$ |
| 3.76(t) 1H | axial $H_1$ |
| 4.85(qt) 1H | C$\underline{H}$ of the cyclopentyl |
| 7.46(t) 1H | $H_5'$ |
| 7.60(d) 1H | $H_6'$ |
| 8.09(bs) 2H | $H_4'$ |
| 8.11(bs) 3H | NH$_2$-cyclohexyl + N=C$\underline{H}$—N |
| 8.29(bs) 1H | $H_2'$ |
| 7.29(bs) | |
| 9.04(s) 1H | mobile H's |
| 10.79(bs) <1H | |

EXAMPLE 109 dihydrochloride of diethyl trans-5-[[2-[(4-amino-cyclohexyl)-amino]-9-cyclopentyl-9H-purin-6-yl]-amino]-1,3-benzenedicarboxylate Stage 1: diethyl 5-[(2-chloro-9-cyclopentyl-9H-purin-6-yl)-amino]-1,3-benzenedicarboxylate.

514 mg of the product obtained in Stage 1 of Example 1 in 8 ml of butanol, 570 mg of diethyl 5-amino-1,3-benzene-diacetate and 331 mg of potassium carbonate are mixed together at ambient temperature then the reaction medium is heated at a temperature of approximately 100° C. for 5 hours and 30 minutes then left to return to ambient temperature and diluted with 15 ml of water, followed by extracting with ethyl acetate, washing with water, drying, evaporating the solvents, impasting in ether, drying under reduced pressure and in this way 723 mg of expected product is obtained.

Stage 2: dihydrochloride of diethyl trans-5-[[2-[(4-aminocyclohexyl)-amino]-9-cyclopentyl-9H-purin-6-yl]-amino]-1,3-benzene-dicarboxylate 1.12 g of trans-1,4-diaminocyclohexane and 641 mg of the product obtained in Stage 1 above are taken to approximately 150° C., the reaction medium is left under agitation for 6 hours and 30 minutes then left to return to ambient temperature for 16 hours. 8 ml of methanol is added, chromatography on silica is carried out (eluent: MeOH/NH$_4$OH 98/2). 116 mg of product is taken up in an ethanolic solution of hydrochloric acid, followed by evaporating the solvents, impasting in ether, separating, drying under reduced pressure at ambient temperature and 144 mg of expected product is recovered.

NMR in DMSO

| | |
|---|---|
| 1.37(m) 10H | the axial H's of the cyclohexyl |
| 1.72(m)–1.92(m) | |
| 2.05(masked) 8H | the CH2's of the cyclopentyl |

-continued

NMR in DMSO

| | |
|---|---|
| 2.21(m) | |
| 2.03(m) 4H | the CH₃'s + equatorial H's of the cyclohexyl |
| 2.97(bs) 1H | axial H₄ |
| 3.73(t) 1H | axial H₁ |
| 4.40(q) 4H | the CH₂O's |
| 4.84(qt) 1H | C$\underline{H}$ of the cyclopentyl |
| 8.02(bs) <3H | NH₂-cyclohexyl + N=C$\underline{H}$—N |
| 8.20(t) 1H | H₄' |
| 8.66(d) 2H | H₂'-H₆' |
| 8.85(bs)–10.90(bs) <1H | mobile H's |

EXAMPLE 110 trans-5-[[2-[(4-aminocyclohexyl)-amino]-9-cyclopentyl-9H-purin-6-yl]-amino]-1,3-benzenedicarboxylic acid (disodium salt)

370 mg of product prepared as in Example 109 is introduced into 5 ml of ethanol, 1.5 ml of 1N soda is added and the reaction medium is agitated for 21 hours at ambient temperature. 2 ml of concentrated hydrochloric acid then 10 ml of water are added to the reaction medium, the precipitate separated, followed by drying under reduced pressure at 50° C. The residue is taken up in 50 ml of methanol, 3 ml of 1N soda is added, followed by evaporating to dryness, impasting in ether and 475 mg of expected product is collected.

NMR in DMSO

| | |
|---|---|
| 1.12(m)–1.27(m) 4H | axial H's of the cyclohexyl |
| 1.67(m)–1.95(m) 4H | equatorial H's of the cyclohexyl |
| 1.68(m)–1.90(m) | |
| 2.05(m) 8H | the CH2's of the cyclopentyl |
| 2.51(masked) | |
| 2.51(masked) | axial H₄ |
| 3.75(tt) 1H | axial H₁ |
| 4.61(m) 1H | C$\underline{H}$ of the cyclopentyl |
| 7.40(s) 1H | N=C$\underline{H}$ |
| 7.87(s) 1H | H$_a$ |
| 7.99(s) 2H | the H$_b$'s |

EXAMPLE 111 dihydrochloride of ethyl trans-3-[[[2-[(4-aminocyclohexyl)-amino]-9-cyclopentyl-9H-purin-6-yl]-amino]-methyl]-benzoate Stage 1: ethyl 3-[[(2-chloro-9-cyclopentyl-9H-purin-6-yl)-amino]-methyl]-benzoate 1.03 g of the product obtained in Stage 1 of Example 1 in 18 ml of n-butanol and 872 mg of 3-(aminomethyl)-benzeneethyl acetate are introduced at ambient temperature and the reaction medium is agitated for 5 hours and 30 minutes in a bath at 100° C. then left to return to ambient temperature. After evaporating the solvents, the residue is taken up with methylene chloride, followed by washing with water, drying and evaporating the solvents. The residue is chromatographed on silica (eluent: CH₂Cl₂/AcOEt 9/1) and 482 mg of expected product is collected.

Stage 2: dihydrochloride of ethyl trans-3-[[[2-[(4-amino-cyclohexyl)-amino]-9-cyclopentyl-9H-purin-6-yl]-amino]-methyl]-benzoate 750 mg of trans-1,4-diaminocyclohexane is taken to approximately 150° C. then 375 mg of the product obtained in Stage 1 above is added, the reaction medium is maintained under agitation at 140° C. for 5 hours 30 minutes then left to return to ambient temperature. Then 5 ml of methanol is added, chromatography on silica is carried out (eluent: MeOH/NH₄OH 98/2, 314 mg of product is collected, 67 mg of which is taken up in 4 ml of an ethanolic solution of hydrochloric acid, after evaporating the solvents 84 mg of expected product is recovered.

NMR in DMSO

| | |
|---|---|
| 1.32(t) 3H | C$\underline{H}_3$—CH₂O |
| 4.32(q) 2H | CH₃—C$\underline{H}_2$O |
| 1.35(m)–1.48(m) | axial H's of the cyclohexyl |
| 1.69(m)–1.88(m) | |
| 2.03(masked) 8H | the CH2's of the cyclopentyl |
| 2.17(m) | |
| 3.02(bs) 1H | axial H₄ |
| 3.69(bt) 1H | axial H₁ |
| 4.76(qt) 1H | C$\underline{H}$ of the cyclopentyl |
| 4.91(bs) | HN—C$\underline{H}_2$-phenyl |
| 7.50(t) 1H | H₅' |
| 7.70(d) 1H–7.87(d) 1H | H₄'-H₆' |
| 8.01(s) 1H | H₂' |
| 8.08(bs) <3H | NH₂-cyclohexyl + N=C$\underline{H}$—N |
| 8.42(bs) <1H–9.53(bs) <1H | mobile H's |

EXAMPLE 112 trans-3-[[[2-[(4-aminocyclohexyl)-amino]-9-cyclopentyl-9H-purin-6-yl]amino]-methyl]-benzoic acid 250 mg of the product obtained in Example 111 is introduced at ambient temperature into 5 ml of ethanol and 0.6 ml of N soda is added. Agitation is carried out for 12 hours at ambient temperature, followed by evaporating the solvents, impasting in ether, drying under reduced pressure at ambient temperature and 227 mg of expected product is collected.

NMR in DMSO

| | |
|---|---|
| from 1.00 to 1.30(m) 5H | the axial H's of the cyclohexyl |
| 1.66(m)–1.90(m)–2.03(m) 8H | the CH2's of the cyclopentyl |
| 1.75(m)–1.90(m) 5H | the equatorial H's of the cyclohexyl |
| 3.60(m) 1H | axial H₁ |
| 4.65(m) 1H | C$\underline{H}$ of the cyclopentyl |
| 4.68(masked) 2H | HN—C$\underline{H}_2$-phenyl |
| 5.73(bd) 1H | N=C(N$\underline{H}$)—N= |
| 7.15(t) 1H | H$_c$ |
| 7.25(bd)–7.69(masked) 2H | H$_b$–H$_d$ |

-continued

NMR in DMSO

| | |
|---|---|
| 7.40(bt) 1H | H̲N—CH$_2$-phenyl |
| 7.68(s) 1H | N=CH̲ |
| 7.86(bs) 1H | H$_a$ |

EXAMPLE 113

Pharmaceutical Composition

Tablets were prepared corresponding to the following formula:

| | |
|---|---|
| Product of Example 6 | 0.2 g |
| Excipient for a tablet completed at | 1 g |
| (detail of the excipient: lactose, talc, starch, magnesium stearate). | |

EXAMPLE 114

Pharmaceutical Composition

Tablets were prepared corresponding to the following formula:

| | |
|---|---|
| Product of Example 59 | 0.2 g |
| Excipient for a tablet completed at | 1 g |
| (detail of the excipient: lactose, talc, starch, magnesium stearate). | |

The invention claimed is:

1. A compound which is n-butyl trans 4-[{[2-(4-aminocyclohexyl)amino}-9-cyclopentyl-9H-purin-yl]-amino]-benzoate or its dihydrochloride.

2. A compound which is ethyl trans-4-[[2-[(4-aminocyclohexyl)-amino]-9-cyclopentyl-9H-purin-6-yl]amino]-benzoate or its dihydrochloride.

3. A compound which is ethyl trans-3-[[2-[(4amino-cyclohexyl)-amino]-9-cyclopentyl-9H-purin-6-yl]amino]-benzoate or its dihychloride.

* * * * *